US009746426B2

(12) United States Patent
Amanullah

(10) Patent No.: US 9,746,426 B2
(45) Date of Patent: Aug. 29, 2017

(54) SYSTEM AND METHOD FOR CAPTURING ILLUMINATION REFLECTED IN MULTIPLE DIRECTIONS

(76) Inventor: Ajharali Amanullah, Singapore (SG)

(*) Notice: Subject to any disclaimer, the term of this patent is extended or adjusted under 35 U.S.C. 154(b) by 644 days.

(21) Appl. No.: 13/181,590

(22) Filed: Jul. 13, 2011

(65) Prior Publication Data

US 2012/0013899 A1  Jan. 19, 2012

(51) Int. Cl.
*G01N 21/00* (2006.01)
*G01N 21/95* (2006.01)
*G01N 21/88* (2006.01)

(52) U.S. Cl.
CPC . *G01N 21/9501* (2013.01); *G01N 2021/8825* (2013.01)

(58) Field of Classification Search
CPC ............... G01N 21/9501; G01N 2021/8825
USPC ................... 356/612, 625, 634–637
See application file for complete search history.

(56) References Cited

U.S. PATENT DOCUMENTS

2007/0273874 A1* 11/2007 Xu et al. ............... 356/237.2

OTHER PUBLICATIONS

Hara, Yasuhiko, Satoru Fushimi, Yoshimasa Ooshima, and Hitoshi Kubota, "Automating Inspection of ALuminium Circuit Pattern of LSI Wafers," Electronics and Communications in Japan, Part 2, vol. 70, No. 3, 1987, pp. 46-58.*

* cited by examiner

*Primary Examiner* — Rebecca C Bryant
(74) *Attorney, Agent, or Firm* — Leif R. Sloan; Sonya C. Harris

(57) ABSTRACT

An optical inspection system in accordance with the disclosure can be configured to simultaneously capture illumination reflected in multiple directions from the surface of a substrate, thereby overcoming inaccurate or incomplete characterization of substrate surface aspects as a result of reflected intensity variations that can arise when illumination is captured only from a single direction. Such a system includes a set of illuminators and an image capture device configured to simultaneously capture at least two beams of illumination that are reflected off the surface. The at least two beams of illumination that are simultaneously captured by the image capture device have different angular separations between their reflected paths of travel. The set of illuminators can include a set of thin line illuminators positioned and configured to supply one or more beams of thin line illumination incident to the surface. For instance, two beams of thin line illumination can be directed to the surface at different angles of incidence to a normal axis of the surface.

22 Claims, 31 Drawing Sheets

Table of Illumination Configurations Selectable by Illumination Configurator

| Configuration | First Illumination Supplied | Second Illumination Supplied |
|---|---|---|
| 1 | Brightfield | High Angle Darkfield |
| 2 | Brightfield | Low Angle Darkfield |
| 3 | Brightfield + High Angle Darkfield | High Angle Darkfield |
| 4 | Brightfield + High Angle Darkfield | Low Angle Darkfield |
| 5 | Brightfield | High Angle Darkfield + Low Angle Darkfield |
| 6 (with same illumination but varying intensity level) | Brightfield with intensity level (e.g. 50%) | Brightfield with intensity level (e.g. 25%) |
| 7 | High Angle Darkfield | Brightfield |
| 8 | Brightfield + High Angle Darkfield | Brightfield + Low Angle Darkfield |
| 9 | High Angle Darkfield with intensity level (e.g. 60%) | High Angle Darkfield with intensity level (e.g. 50%) |

FIG. 20

Timing chart of 2D image acquisition from first and second image capture devices FIG. 22a First Image
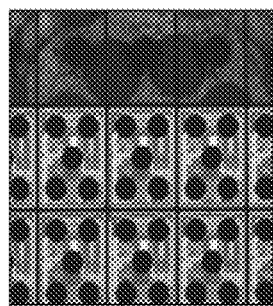
FIG. 22b Second Image
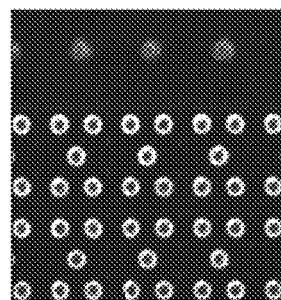
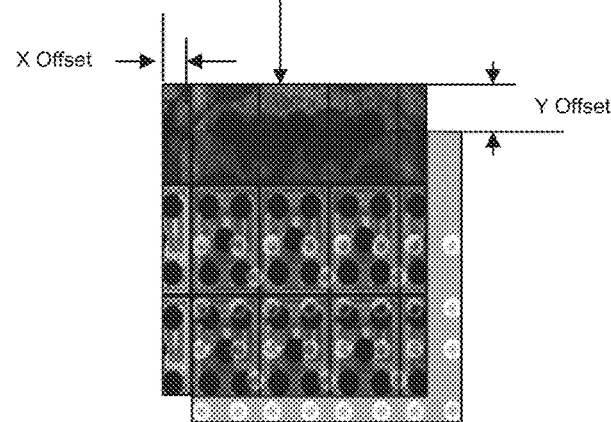
FIG. 22c Combined first Image and second image demonstrating image offset due to image capture while wafer is moving

SYSTEM AND METHOD FOR CAPTURING ILLUMINATION REFLECTED IN MULTIPLE DIRECTIONS

CROSS-REFERENCE TO RELATED APPLICATIONS

This application claims priority to and the benefit of the following Singapore Application, which is hereby incorporated by reference: Singapore Patent Application No. 201005085-4, filed 13 Jul. 2010. The applicant claims the benefit of the prior application under the relevant section(s) of 35 USC 119 and claims priority under rule 37 CFR 1.55.

TECHNICAL FIELD

The present disclosure relates generally to a wafer inspection process. More specifically, the present disclosure relates to an automated system and method for inspecting semiconductor components.

BACKGROUND

The ability to ensure a consistently high quality of manufactured semiconductor components, for example semiconductor wafers and dies, is increasingly crucial in the semiconductor industry. Semiconductor wafer fabrication techniques have been consistently improved to incorporate an increasing number of features into a smaller surface area of the semiconductor wafer. Accordingly, the photolithographic processes used for semiconductor wafer fabrication has become more sophisticated to allow the incorporation of increasing features to the smaller surface area of the semiconductor wafer (i.e. higher performance of the semiconductor wafer). Consequently, sizes of potential defects on semiconductor wafers are typically in the micron to submicron range.

It is evident that manufacturers of semiconductor wafers have an increasingly pressing need to improve semiconductor wafer quality control and inspection procedures to ensure a consistently high quality of manufactured semiconductor wafers. Semiconductor wafers are typically inspected for detecting defects thereon, such as presence of surface particulates, imperfections, undulations and other irregularities. Such defects could affect eventual performance of the semiconductor wafer. Therefore, it is critical to eliminate or extract defective semiconductor wafers during the manufacture thereof.

There have been advances in semiconductor inspection systems and processes. For example, higher resolution imaging systems, faster computers, and enhanced precision mechanical handling systems have been commissioned. In addition, semiconductor wafer inspection systems, methods and techniques have historically utilized at least one of brightfield illumination, darkfield illumination and spatial filtering techniques.

With brightfield imaging, small particles on the semiconductor wafer scatter light away from a collecting aperture of an image capture device, thereby resulting in a reduction of returned energy to the image capture device. When the particle is small in comparison with the optical point spread function of a lens or digitalizing pixel, brightfield energy from the immediate areas surrounding the particle generally contribute a large amount of energy relative to the particle, thereby making the particle difficult to detect. In addition, the very small reduction in energy due to the small particle size is often masked by reflectivity variations from the immediate areas around the particle thereby resulting in increased occurrences of false defect detection. To overcome the above phenomena, semiconductor inspection systems have been equipped with high-end cameras with larger resolutions, which capture images of smaller surface areas of the semiconductor wafer. However, brightfield images generally have a better pixel contrast and this is advantageous for estimating size of defects and when inspecting dark defects.

Darkfield illumination and its advantages are generally well-known in the art. Darkfield imaging has been employed with several existing semiconductor wafer inspection systems. Darkfield imaging typically depends on the angle at which light rays are incident on the object to be inspected. At a low angle to a horizontal plane of the object to be inspected (for example 3 to 30 degrees), darkfield imaging typically produces a dark image except at locations where defects, such as surface particulates, imperfections and other irregularities exist. A particular use of darkfield imaging is to light up defects which sizes are smaller than the resolving power of lens used to produce a brightfield image. At a higher angle to the horizontal plane (for example 30 to 85 degrees), darkfield imaging typically produces better contrast images compared to brightfield images. A particular use of such high angle darkfield imaging enhances contrast of surface irregularities on a mirror finish or transparent object. In addition, high angle darkfield imaging enhances imaging of tilted objects.

Light reflectivity of the semiconductor wafer typically has a significant effect on quality of image obtained with each of brightfield and darkfield imaging. Both micro and macro structures present on the semiconductor wafer affect the light reflectivity of the semiconductor wafer. Generally, amount of light reflected by the semiconductor wafer is a function of the direction or angle of incident light, the viewing direction and the light reflectivity of the surface of the semiconductor wafer. The light reflectivity is in turn dependent on wavelength of the incident light and material composition of the semiconductor wafer.

It is generally difficult to control the light reflectivity of semiconductor wafers presented for inspection. This is because the semiconductor wafer may consist of several layers of material. Each layer of material may transmit different wavelengths of light differently, for example at different speeds. In addition, layers may have different light permeabilities, or even reflectivity. Accordingly, it will be apparent to a person skilled in the art that the use of light or illumination of a single wavelength or a narrow band of wavelengths typically adversely affects quality of captured images. Need for frequent modification of the single wavelength or narrow band of wavelengths requires use of multiple spatial filters or wavelength tuners, which can be generally inconvenient. To alleviate such problems, it is important to use a broadband illumination (i.e. illumination of a wide range of wavelengths), for example broadband illumination of a range of wavelengths between 300 nm and 1000 nm.

Currently available wafer inspection systems or equipments typically use one of the following methods for achieving or capturing multiple responses during wafer inspection:
(1) Multiple Image Capture Devices with Multiple Illuminations (MICD)

The MICD uses a plurality of image capture devices and a plurality of illuminations. The MICD is based on the principle of segmenting the wavelength spectrum into narrow bands, and allocating each segmented wavelength spectrum to individual illuminations. During design of systems employing the MICD method, each image capture device is paired with a corresponding illumination (i.e. illumination source), together with corresponding optical accessories such as a spatial filter or a specially coated beam splitter. For example, wavelength of the brightfield illumination is limited between 400 to 600 nm using mercury arc lamp and spatial filter and the darkfield illumination is limited between 650 to 700 nm using lasers. The MICD method experiences disadvantages, for example inferior image quality and design inflexibility. Inferior image quality is due to varying surface reflectivities of inspected wafers, combined with the use of illuminations with narrow wavelengths. Design inflexibility occurs because the modification of the wavelength of a single illumination typically requires reconfiguration of the entire optical setup of the wafer inspection system. In addition, the MICD method typically does not allow capture of illuminations with varying wavelengths by a single image capture device without compromising the quality of captured images.

(2) Single Image Capture Device with Multiple Illuminations (SICD)

The SICD method uses a single image capture device for capturing multiple illuminations, either with segmented wavelengths or broadband wavelengths. However, it is not possible to obtain multiple illumination responses simultaneously while the wafer is in motion. In other words, the SICD method only allows one illumination response when the wafer is in motion. To achieve multiple illumination responses, the SICD method requires image captures while the wafer is stationary, which affects throughput of the wafer inspection system.

Semiconductor wafer inspection systems employing simultaneous, independent, on-the-fly image capture using broadband brightfield and darkfield or in general multiple illuminations and using multiple image capture devices are not presently available due to a relative lack of understanding as to actual implementation and operating advantages thereof. Existing semiconductor wafer inspection systems are employing either MICD or SICD as explained earlier. Equipments employing MICD do not use broadband illumination and suffer from inferior image quality and inflexible system setup. On the other hand equipments using SICD experience diminished system throughput and are typically incapable of obtaining on-the-fly simultaneous multiple illumination responses.

An exemplary existing semiconductor wafer optical inspection system that utilizes both brightfield illumination and darkfield illumination is disclosed in U.S. Pat. No. 5,822,055 (KLA1). An embodiment of the optical inspection system disclosed in KLA1 utilizes MICD as explained earlier. It uses multiple cameras to capture separate brightfield and darkfield images of semiconductor wafers. Captured brightfield and darkfield images are then processed separately or together for detecting defects on the semiconductor wafer. In addition, the optical inspection system of KLA1 captures brightfield and darkfield images simultaneously using separate sources of brightfield and darkfield illumination. KLA1 achieves simultaneous image capture using segmentation of illumination wavelength spectrum, narrow band illumination sources and spatial filters for enabling capture of the brightfield and darkfield images. In the KLA1-optical system, one of the cameras is configured to receive darkfield imaging using narrow band laser and spatial filter. The other camera is configured to receive rest of the wavelength spectrum using brightfield illumination and a beam splitter with special coating. Disadvantages of the optical inspection system disclosed by KLA1 include unsuitability thereof for imaging different semiconductor wafers comprising a large variation of surface reflectivities due to segmentation of the wavelength spectrum. The cameras are tightly coupled with respective illumination and there is no flexibility of combining of more than one available illumination to enhance certain wafer types. One such type is having carbon coated layer on its front side and they exhibit poor reflection characteristics at certain illumination angle, for example using brightfield alone. It requires combination of brightfield and high angle darkfield illumination to view certain defects. Accordingly, the optical inspection system of KLA1 requires a plurality of light or illumination sources and filters for performing multiple inspection passes (multiple scan which in turn affects the throughput of the system) to thereby capture multiple brightfield and darkfield images.

Additional exemplary exiting optical inspection systems utilizing both brightfield and darkfield imaging are disclosed in U.S. Pat. No. 6,826,298 (AUGTECH1) and U.S. Pat. No. 6,937,753 (AUGTECH2). Darkfield imaging of the optical inspection systems of AUGTECH1 and AUGTECH2 utilizes a plurality of lasers for low-angle darkfield imaging, and a fiber optic ring light for high-angle darkfield imaging. In addition, the optical inspection system of AUGTECH1 and AUGTECH2 uses a single camera sensor and belongs to SICD method explained earlier. Accordingly, inspection of semiconductor wafers in AUGTECH1 and AUGTECH2 is performed either by brightfield imaging or by darkfield imaging or via a combination of both brightfield imaging and darkfield imaging wherein each of the brightfield imaging and darkfield imaging is performed when the other is completed. The inspection system of AUGTECH1 and AUGTECH2 is not capable of simultaneous, on-the-fly or while wafer is in motion and independent brightfield and darkfield imaging. Accordingly, multiple passes of each semiconductor wafer is required for completing inspection thereof, resulting in lowered manufacturing throughput and undue increase in utilization of resources.

In addition, several existing optical inspection systems utilize a golden image or a reference image for comparison with newly acquired images of semiconductor wafers. Derivation of the reference image typically requires capturing several images of known or manually selected "good" semiconductor wafers and then applying a statistical formula or technique to thereby derive the reference image. A disadvantage with the above derivation is presence of inaccuracies or inconsistencies in manual selection of the "good" semiconductor wafers. Optical inspection systems using such reference images typically suffer from false rejects of semiconductor wafers due to inaccurate or inconsistent reference images. With increasingly complex circuit geometry of semiconductor wafers, reliance on manual selection of "good" semiconductor wafers for deriving reference images is increasingly incompatible with increasingly high quality standards set by the semiconductor inspection industry.

Deriving a golden reference image involves many statistical techniques and calculations. Most of the statistical techniques are very general and have their own merits. State of the art of the currently available equipments uses either average or mean together with standard deviation to calculate a golden reference pixel. This method works well with known good pixels; otherwise any defect or noise pixel would interfere and affect a final average or mean value of the reference pixel. Another method is to use median and it has reduced interference due to noise pixel but is not possible to eliminate the effect of noise substantially. All of the available equipments try to reduce the error by applying different kinds of statistical techniques such as mean, median among others, but they do not have any special or user friendly sequence to eliminate the error. Such special sequence certainly helps to eliminate pixels which would affect the final reference pixel value.

U.S. Pat. No. 6,324,298 (AUGTECH3) discloses a training method for creating a golden reference or reference image for use in semiconductor wafer inspection. The method disclosed in AUGTECH3 requires "Known Good Quality" or "Defect Free" wafers. Selection of such wafers is manually or user performed. Statistical formulas or techniques are then applied for deriving the reference image. As such, accurate and consistent selection of "good quality" wafers is crucial for accurate and consistent quality of semiconductor inspection. Further, AUGTECH3 uses mean and standard deviation to calculate individual pixels of the reference image and presence of any defective pixel will lead to inaccurate reference pixel. The defective pixel occurs due to foreign matter or other defects, which would confuse the statistical calculation and lead to incorrect reference pixel. It will be apparent to a person skilled in the art that the method of AUGTECH3 is open to inaccuracies, inconsistencies and errors in inspection of the semiconductor wafers.

In addition, optical inspection system disclosed in AUGTECH3 uses a flash or strobe lamp for illuminating the semiconductor wafers. It will be appreciated by a person skilled in the art that inconsistencies between different flashes or strobes may occur due to numerous factors including, but not limited to, temperature differentials, electronic inconsistencies and differential flash or strobe intensities. Such differentials and inconsistencies are inherent even with "good" semiconductor wafers. Presence of such differentials would affect the quality of golden reference image if the system had not taken care of such differentials due to flash lamp. In addition, illumination intensity and uniformity varies across the surface of the semiconductor wafer due to factors including, but not limited to planarity of the wafer, mounting and light reflectivity at different positions of the surface. Without taking into account the variations in the flash intensity and the strobing characteristics of the lamp, any reference images generated in the above-described manner may be unreliable and inaccurate when used for comparing with captured images of different positions of the semiconductor wafers.

Variations in product specifications, for example semiconductor wafer size, complexity, surface reflectivity and criteria for quality inspection, are common in the semiconductor industry. Accordingly, semiconductor wafer inspection systems and methods need to be capable of inspecting such variations in product specifications. However, existing semiconductor wafer inspection systems and methods are generally incapable of satisfactorily inspecting such variations in product specifications, especially given the increasing quality standards set by the semiconductor industry.

For example, a typical existing semiconductor wafer inspection system uses a conventional optical assembly comprising components, for example cameras, illuminators, filters, polarizers, mirrors and lens, which have fixed spatial positions. Introduction or removal of components of the optical assembly generally requires rearrangement and redesign of the entire optical assembly. Accordingly, such semiconductor wafer inspection systems have inflexible designs or configurations, and require a relatively long lead-time for modification thereof. In addition, distance between objective lens of the convention optical assembly and semiconductor wafer presented for inspection is typically too short to allow ease of introduction of fiber optics illumination with differing angles for darkfield illumination.

There are numerous other existing semiconductor wafer inspection systems and methods. However, because of current lack of technical expertise and operational know-how, existing semiconductor wafer inspection systems cannot employ simultaneous brightfield and darkfield imaging for an inspection while the wafer is in motion, while still maintaining flexibility in design. There is also a need for semiconductor wafer inspection systems and methods for enabling resource-efficient, flexible, accurate and fast inspection of semiconductor wafers. This is especially given the increasing complexity of electrical circuitry of semiconductor wafers and the increasing quality standards of the semiconductor industry.

SUMMARY

There is currently a lack of semiconductor wafer inspection systems and methods capable of employing both brightfield and darkfield imaging simultaneously and independently for performing inspection while the semiconductor wafer is in motion, while providing flexibility in design and configuration. In addition, there is need for a semiconductor wafer inspection system wherein components thereof, for example illuminators, camera, objective lens, filters and mirrors, have flexible and adjustable spatial positions relative to each other. Given the increasing complexity of electrical circuitry of semiconductor wafers, and the increasing quality standards set by the semiconductor industry, accuracy and consistency of semiconductor wafer inspection is increasingly critical.

The present disclosure provides an inspection apparatus, device, system, method, and/or process for inspecting semiconductor components, including, but not limited to semiconductor wafers, dies, LED chips and solar wafers.

In accordance with a first aspect of the present disclosure, there is disclosed an apparatus including a set of illuminators configured to supply illumination, the illumination supplied by the set of illuminators directed towards an inspection position corresponding to a surface under inspection. The illumination reflects off the surface in at least a first direction and a second direction. The apparatus also includes a first set of reflectors positioned and configured to receive illumination reflected off the surface in the first direction and direct received illumination along a first reflected illumination travel path and a second set of reflectors positioned and configured to receive illumination reflected off the surface in the second direction and direct received illumination along a second reflected illumination travel path. In addition, the apparatus includes an image capture device configured to simultaneously receive illumination traveling along each of the first and second reflected illumination travel paths to thereby provide a first response and a second response respectively.

In accordance with a second aspect of the present disclosure, there is disclosed a method for inspecting a surface. The method includes directing illumination towards an inspection position corresponding to a surface under inspection and reflecting illumination off the surface in at least a first direction and a second direction. In addition, the method includes directing the illumination reflected off the surface in the first direction and the second direction along a first reflected illumination travel path and a second reflected illumination travel path respectively. Furthermore, the method includes simultaneously receiving illumination traveling along each of the first and second reflected illumination travel paths by an image capture device to produce a first and second response corresponding to the first and second reflected illumination travel paths respectively.

In accordance with a third aspect of the present disclosure, there is disclosed an optical system that includes a set of illuminators configured to supply illumination to a surface corresponding to an inspection position, the illumination comprising a first beam of illumination that is incident to the surface at a first angle to the surface and a second beam of illumination that is incident to the surface at a second angle to the surface that is different from the first angle. The optical system also includes an image capture device configured to simultaneously receive the first and second beams of illumination reflected off the surface along an optical axis of the image capture device.

In accordance with a fourth aspect of the present disclosure, there is disclosed a method including supplying a first beam of illumination to an inspection position corresponding to a surface, the first beam of illumination being incident to the surface at a first angle and supplying a second beam of illumination to the surface, the second beam of illumination being incident to the surface at a second angle different than the first angle. In addition, the method includes reflecting the first and second beams of illumination off the surface and simultaneously receiving the reflected first and second beams of illumination by an image capture device.

BRIEF DESCRIPTION OF THE DRAWINGS

Particular embodiments of the present disclosure are described hereinafter with reference to the following drawings, in which:

FIG. 20 shows a table of illumination configurations selectable by an illumination configurator of the system of FIG. 1;

FIG. 22a shows the first image captured by the first image capture device of FIG. 1;

FIG. 22b shows the second image captured by the second image capture device of FIG. 1;

FIG. 22c shows a combined first image of FIG. 22a and second image of FIG. 22b for demonstrating image offset due to the capture of the first image and the second image when the wafer is moving;

DETAILED DESCRIPTION

The inspection of semiconductor components, for example semiconductor wafers and dies, is an increasingly critical step in the manufacture or fabrication of semiconductor components. Increasing complexity of circuitry of semiconductor wafers, coupled with increasing quality standards for semiconductor wafers, has led to an increasing need for improved semiconductor wafer inspection systems and methods. Given the increasing complexity of electrical circuitry of semiconductor wafers and the increasing quality standards set by the semiconductor industry, accuracy and consistency of semiconductor wafer inspection is increasingly critical. In particular, accuracy and consistency of identifying defects that may be present on semiconductors wafers is increasingly important.

The present disclosure relates to systems, apparatuses, devices, methods, processes, and techniques for inspecting devices, for example semiconductor components, for addressing at least one of the above-identified issues.

For purposes of brevity and clarity, the description of embodiments of the present disclosure is limited hereinafter to systems, apparatuses, devices, methods, processes, and techniques for inspecting semiconductor wafers. It will however be understood by a person skilled in the art that this does not preclude the present disclosure from other applications where fundamental principles prevalent among the various embodiments of the present disclosure such as operational, functional, or performance characteristics are required. For example, the systems, apparatuses, devices, methods, processes, and techniques provided by various embodiments of the present disclosure can be used for inspecting other semiconductor components, including but not limited to, semiconductor dies, LED chips, and solar wafers or devices.

Figure 1:
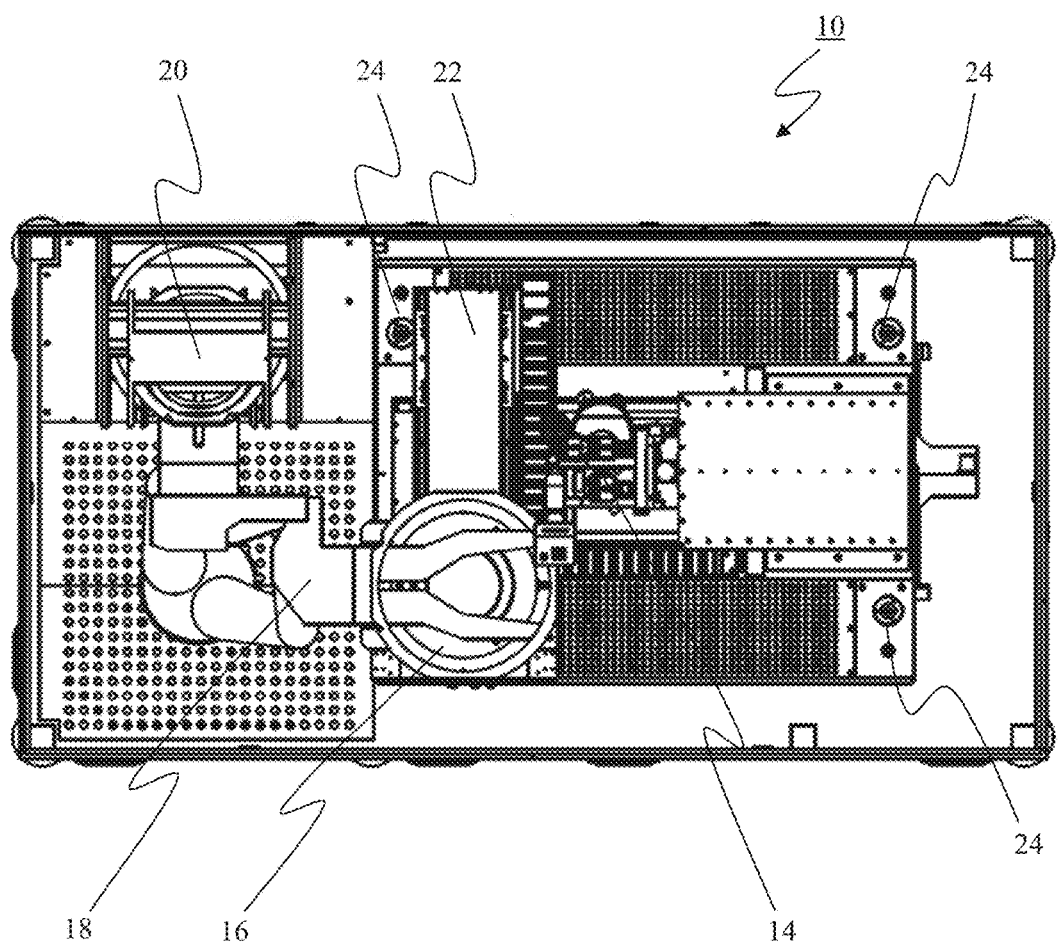
FIG. 1 shows a partial plan view of an exemplary system for inspecting wafers according to an exemplary embodiment of the present disclosure.
Figure 2:
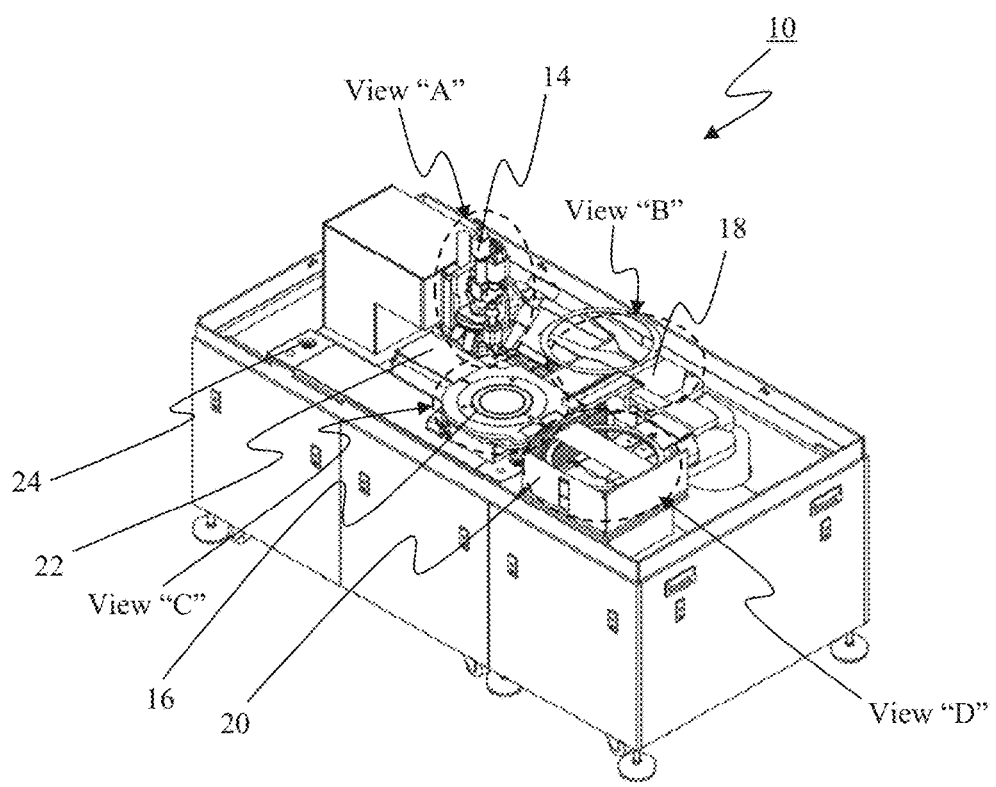
FIG. 2 shows a partial isometric view of the system of FIG. 1.

FIG. 1 and FIG. 2 show an exemplary system 10 for inspecting semiconductor wafers 12 provided by particular embodiments of the present disclosure. FIG. 3 to FIG. 8 show various aspects or components of the system 10 as according to various embodiments of the present disclosure.

Figure 3:
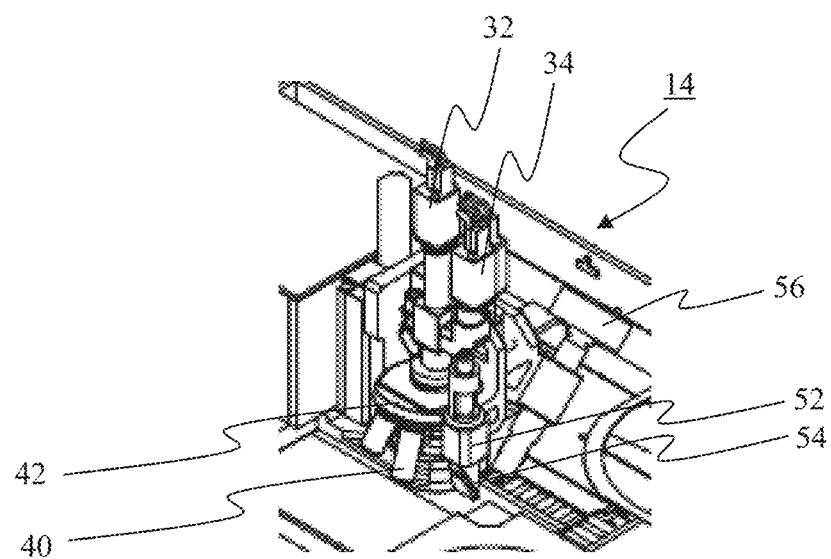
FIG. 3 shows an exploded partial isometric view of an optical inspection head of the system of FIG. 1 according to view "A" highlighted in FIG. 2.
Figure 4:
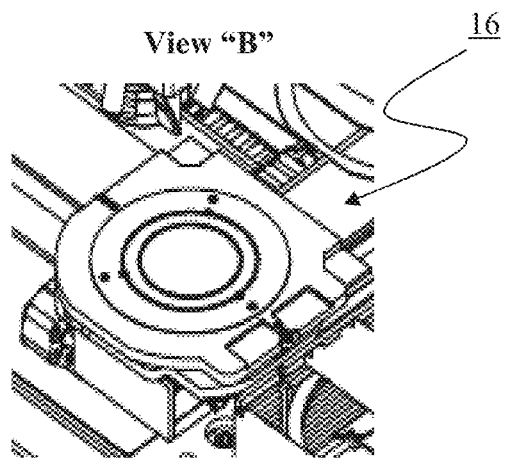
FIG. 4 shows an exploded partial isometric view of a robotic wafer table of the system of FIG. 1 according to view "B" highlighted in FIG. 2.
Figure 5:
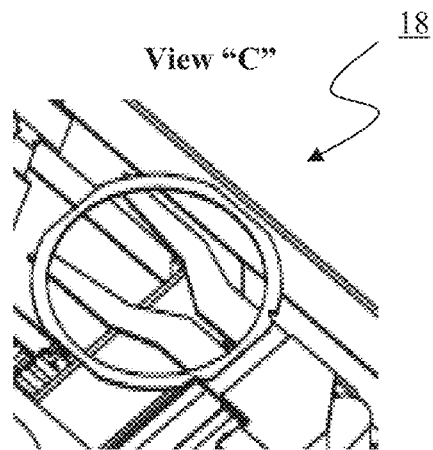
FIG. 5 shows an exploded partial isometric view of a robotic wafer loader/unloader of the system of FIG. 1 according to view "C" highlighted in FIG. 2.
Figure 6:
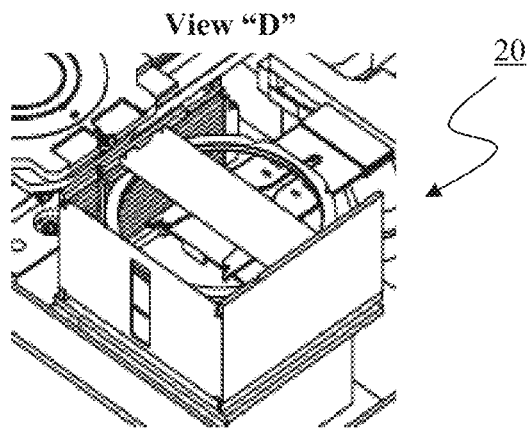
FIG. 6 shows an exploded partial isometric view of a wafer stack module of the system of FIG. 1 according to view "D" highlighted in FIG. 2.

The system 10 can also be used for inspecting other types of devices or components (e.g., semiconductor devices or components). In many embodiments, the system 10 includes an optical inspection head 14 (as shown in FIG. 3), a wafer transportation table or wafer chuck 16 (as shown in FIG. 4), a robotic wafer handler 18 (as shown in FIG. 5), a wafer stack module 20 (as shown in FIG. 6) or film frame cassette holder, an X-Y displacement table 22, and at least one set of quad vibration isolators 24 (as shown in FIG. 1 and FIG. 2).

Figure 7:
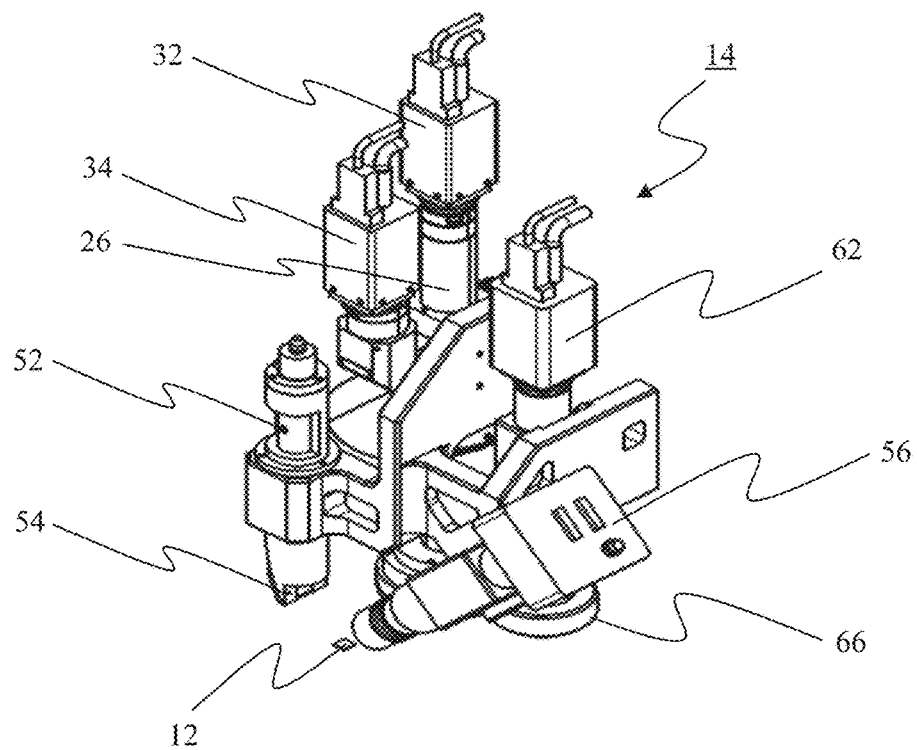
FIG. 7 shows a partial isometric view of the optical inspection head of the system of FIG. 1.
Figure 8:
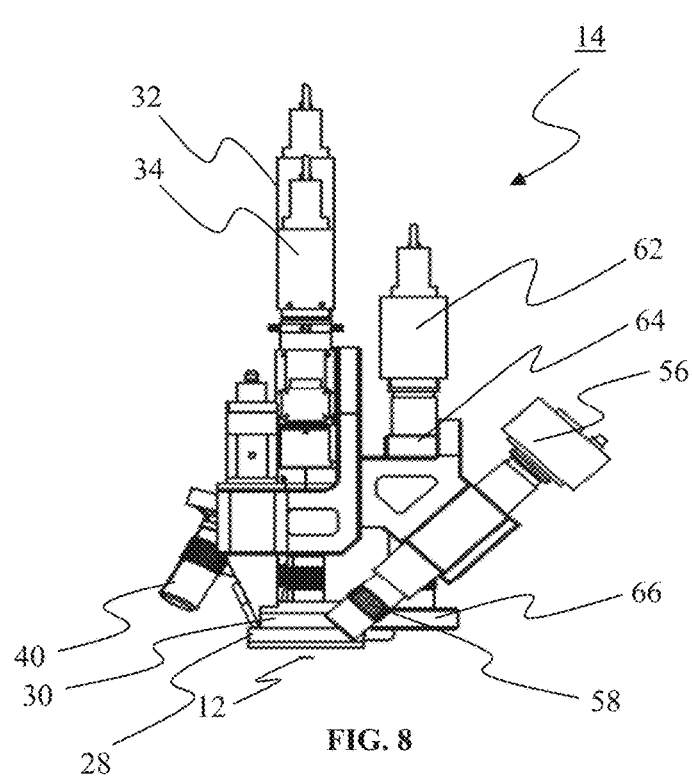
FIG. 8 shows a partial front view of the optical inspection head of the system of FIG. 1.
Figure 9:
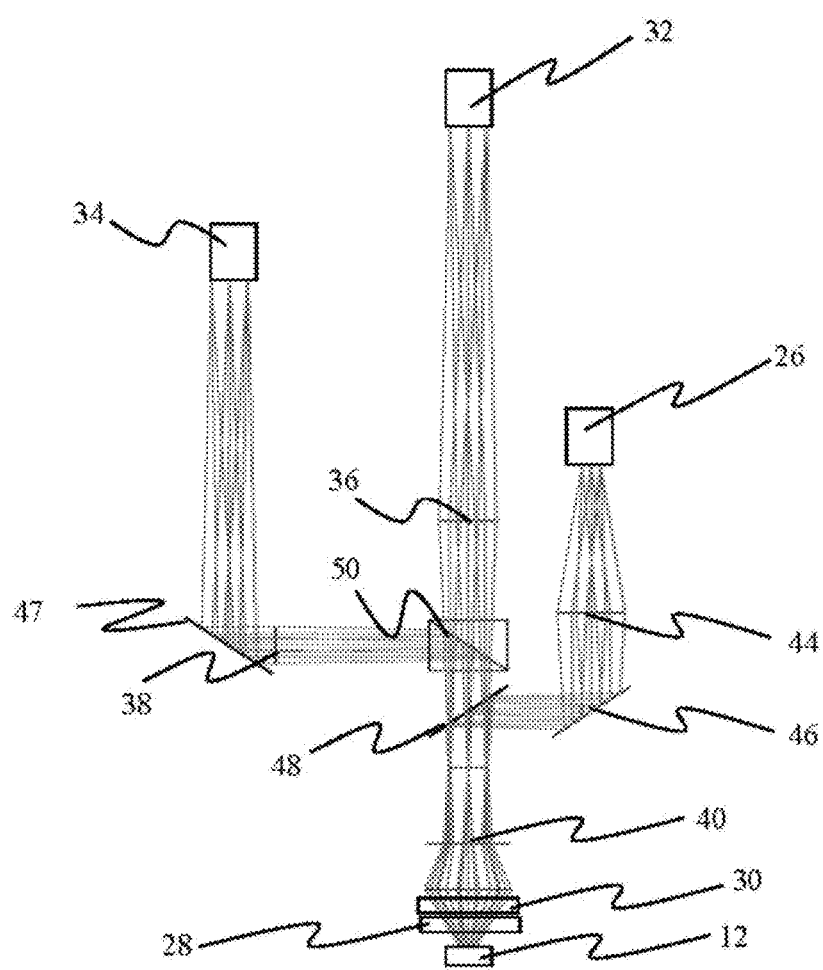
FIG. 9 shows optical ray paths of illumination between a brightfield illuminator, a low angle darkfield illuminator, a high angle darkfield illuminator, a first image capture device and a second image capture device of the system of FIG. 1.

As shown in FIG. 7 and FIG. 8, in various embodiments, the optical inspection head 14 includes a number of illuminators, for example two, three, four, or more, illuminators, a number of image capture devices, for example two, three, four, or more image capture devices.

An inspection process typically involves the captures of responses by one or more of the system's image capture devices. In various embodiments, a response can be defined as captured illumination (e.g., captured optical signals or a captured image) having properties or carrying information content that corresponds to or is indicative of two dimensional (2D) or three dimensional (3D) aspects of a particular portion or region of a wafer or substrate surface. Additionally or alternatively, a response can be defined as illumination having properties or information content that corresponds to or indicates 2D or 3D aspects of a portion of a surface under consideration as a result of the illumination's interaction with the portion of the surface. In general, a response is includes or corresponds to illumination or image data having properties or information content that can be used to determine or estimate particular 2D or 3D characteristics of a portion of a wafer.

In many embodiments, the optical inspection head 14 includes a brightfield illuminator 26 (also known as a brightfield illumination emitter), a low angle darkfield illuminator 28 (also known as a darkfield low angle illumination emitter) and a high angle darkfield illuminator 30 (also known as a darkfield high angle illumination emitter). Additional darkfield illuminators may be incorporated into the system 10, for instance depending upon particular functions of the system 10. In various embodiments, the low angle darkfield illuminator 28 and the high angle darkfield illuminator 30 can be integrated as a single darkfield illuminator, which may be flexibly positioned.

The brightfield illuminator 26, also known as a brightfield illumination source or brightfield illumination emitter, emits or supplies brightfield illumination or light. The brightfield illuminator 26 is for example, a flash lamp or a white light emitting diode. In several embodiments of the present disclosure, the brightfield illuminator 26 supplies broadband brightfield illumination having wavelengths of substantially between and including 300 nm and 1000 nm. It will however be understood by a person skilled in the art that the brightfield illumination may be of alternative wavelengths and optical properties.

In several embodiments of the present disclosure, the brightfield illuminator 26 includes a first optical fiber (not shown) through which the brightfield illumination travels before being emitted from the brightfield illuminator 26. The first optical fiber acts as a waveguide for guiding direction of travel of brightfield illumination. In numerous embodiments of the present disclosure, the first optical fiber facilitates directing of the brightfield illumination emitted from the brightfield illuminator 26.

The low angle darkfield illuminator 28 and the high angle darkfield illuminator 30 can also be known as darkfield illumination emitters or darkfield illumination sources, and emit or supply darkfield illumination. Generally, darkfield illuminators are carefully aligned or disposed illumination or light sources that enable minimization of the quantity of directly transmitted (or un-scattered) light entering their corresponding image capture devices. Typically, image capture devices for capturing darkfield images receive only illumination or light that has been scattered by a sample or object (e.g., reflected at angle(s) off a surface of the sample). Darkfield images generally have an enhanced image contrast as compared to brightfield images. Brightfield illumination and darkfield illumination are examples of contrast illuminations.

The low angle darkfield illuminator 28 and the high angle darkfield illuminator 30 are for example flash lamps or white light emitting diodes. In many embodiments of the present disclosure, the darkfield illumination supplied by each of the low angle darkfield illuminator 28 and the high angle darkfield illuminator 30 is of substantially similar optical properties as the brightfield illumination. In some embodiments, the darkfield illumination supplied by each of the low angle darkfield illuminator 28 and the high angle darkfield illuminator 30 is a broadband darkfield illumination having a wavelength of substantially between and including 300 nm to 1000 nm. This is to say that both the brightfield illumination and the darkfield illumination of the system 10 are broadband illuminations in several embodiments of the present disclosure. Alternatively, the low angle darkfield illuminator 28 and the high angle darkfield illuminator 30 supply darkfield illumination of different wavelengths or other optical properties.

In many embodiments, the low angle darkfield illuminator 28 is positioned at a lower angle, as compared to the high angle darkfield illuminator 30, to a horizontal plane of the semiconductor wafer 12 placed on the wafer table 16 (or to a horizontal plane of the wafer table 16).

In some embodiments, the low angle darkfield illuminator 28 is positioned at an angle of between approximately three and thirty degrees to the horizontal plane of the semiconductor wafer 12 placed on the wafer table 16 and the high angle darkfield illuminator 30 is positioned at an angle of between approximately thirty and eighty-five degrees to a horizontal plane of the semiconductor wafer 12 placed on the wafer table 16. The above-stated angles can be determined and altered as desired, for instance depending upon function or characteristics of the system 10, by adjusting the position of each of the low angle darkfield illuminator 28 and the high angle darkfield illuminator 30.

In several embodiments, the low angle darkfield illuminator 28 and the high angle darkfield illuminator 30 include a second and a third optical fiber respectively (not shown) through which darkfield illumination travels before being emitted therefrom. The second and third optical fibers act as a waveguide for guiding direction of travel of the darkfield illumination through each of the low angle darkfield illuminator 28 and the high angle darkfield illuminator 30. In addition, the second optical fiber facilitates directing of the darkfield illumination emitted from the low angle darkfield illuminator 28 and the third optical fiber facilitates directing of the darkfield illumination emitted from the high angle darkfield illuminator 30. Illumination supplied by each of the brightfield illuminator 26, the low angle darkfield illuminator 28 and the high angle darkfield illuminator 30 can be controlled, and can be either continuously supplied or pulsed.

In various embodiments, the wavelength spectrums of both the brightfield illumination and darkfield illuminations enhance accuracy of inspection and defect detection of the wafers 12. Broadband illumination enables identification of a wide range of wafer defect types with varying surface reflectivities. In addition, in particular embodiments, the similar broadband wavelengths of both the brightfield illumination and the darkfield illuminations (e.g., the low angle darkfield illumination and high angle darkfield illumination) enable the inspection of the wafer 12 to be performed independent of reflective characteristics of the wafer 12. Accordingly, in particular embodiments, the detection of defects on the wafer 12 may not be undesirably influenced due to different sensitivities, reflectiveness, or polarization of the wafer 12 due to different illumination wavelengths.

In many embodiments of the present disclosure, the intensities of the brightfield illumination and the darkfield illumination supplied by the brightfield illuminator 26 and the darkfield illuminators 28, 30 respectively can be selected and varied as required depending on wafer 12 characteristics, for example material of the wafer 12. In addition, the intensities of each of the brightfield illumination and darkfield illuminations can be selected and varied as required for enhancing quality of images captured of the wafer 12, and for enhancing inspection of the wafer 12.

As shown in FIG. 7 to FIG. 8, in various embodiments, the system 10 further includes a first image capture device 32 (i.e. a first camera) and a second image capture device 34 (i.e. a second camera).

In numerous embodiments, each of the first image capture device 32 and the second image capture device 34 is capable of receiving brightfield illumination supplied by the brightfield illuminator 26 and the darkfield illuminations supplied by each of the low angle darkfield illuminator 28 and high angle darkfield illuminator 30. Brightfield and darkfield illuminations received by or entering the first image capture device 32 is focused onto a first image capture plane for capture of corresponding images. Brightfield and darkfield illuminations received by or entering the second image capture device 34 is focused on a second image capture plane for capture of corresponding images.

The first image capture device 32 and the second image capture device 34 capture either monochromatic or color images. In many embodiments, the ability to capture color images of the wafer 12 using either a single or a three-chip color sensor carried by the image capture devices 32 and 34 enhances at least one of accuracy and speed of defect detection. For example, the ability to capture color images of the wafer 12 can help to reduce false detection of defects on the wafer 12, and correspondingly false rejection thereof.

In many embodiments, the optical inspection head 14 includes a first tube lens or tube lens assembly 36 for use with the first image capture device 32. In addition, in numerous embodiments, the optical inspection head 14 includes a second tube lens or tube lens assembly 38 for use with the second image capture device 34. In numerous embodiments, the first tube lens 36 and the second tube lens 38 share common optical characteristics and functions. Accordingly, the tube lenses 36 and 38 have been labeled the first tube lens 36 and the second tube lens 38 solely for purposes of clarity.

In many embodiments, the optical inspection head 14 also includes a number of objective lenses 40 (or objective lens assemblies 40), for example four objective lenses 40. In various embodiments, the objective lenses 40 are collectively mounted on a rotatable mount 42 (as shown in FIG. 3), which is rotatable for positioning each of the number of objective lens 40 above an inspection position (not shown), at which the wafer 12 can be positioned for inspection.

In numerous embodiments, each of the number objective lenses 40 can be shaped and configured to achieve a different magnification. In addition, in many embodiments, the objective lens 40 are parfocal. In several embodiments, each of the number of objective lens 40 is of a different predetermined magnification factor, for example five times, ten times, twenty times, and fifty times. In some embodiments, each of the number of objective lenses 40 has a corrected aberration in infinity. It will however be understood by a person skilled in the art that each of the number of objective lenses 40 can be changed, redesigned, or reconfigured to achieve a different magnification and performance.

In many embodiments of the present disclosure, each of the low angle darkfield illuminator 28 and the high angle darkfield illuminator 30 includes focusing means or mechanisms for directing or focusing the darkfield illumination therefrom towards the wafer 12 positioned at the inspection position. In particular embodiments, the angle between the low angle darkfield illuminator 28 and the horizontal plane of the wafer 12 and the angle between the high angle darkfield illuminator 30 and the horizontal plane of the wafer 12 can be determined and adjusted for enhancing accuracy of defect detection.

In several embodiments of the present disclosure, each of the low angle darkfield illuminator 28 and the high angle darkfield illuminator 30 has a fixed spatial position with reference to the inspection position. In other embodiments of the present disclosure, the position of each of the low angle darkfield illuminator 28 and the high angle darkfield illuminator 30 is variable with reference to the inspection position during normal operation of the system 10.

As described above, in many embodiments, both the brightfield illumination and the darkfield illuminations can be focused, or directed, at the inspection position, and accordingly a wafer 12 positioned at the inspection position. The brightfield illumination and the darkfield illuminations focused, or directed, at the inspection position enable illumination of a wafer 12, or a portion thereof, positioned at the inspection position.

As shown in FIG. 6, in various embodiments, the system 10 includes a wafer stack 20 or filmframe cassette holder. In several embodiments, the wafer stack 20 includes slots to hold a number of wafers 12. In some embodiments, each wafer 12 is sequentially loaded or transferred onto the wafer table 16 (shown in FIG. 4) or wafer chuck by the robotic wafer handler 18 (shown in FIG. 5). A suction or vacuum can be applied through the wafer table 16 for securing the wafer 12 thereonto. In some embodiments, the wafer table 16 includes a predetermined number of small holes or apertures through which vacuum is applied to enable a reliable and flat positioning of a flex frame tape and a frame (both not shown) onto the wafer table 16. In numerous embodiments, the wafer table 16 is shaped, dimensioned, and designed to handle wafers 12 of a size range of between and including approximately six and twelve inches in diameter. In particular embodiments, the wafer table 16 can be shaped, dimensioned, and designed to handle wafers 12 of different sizes, for instance less than approximately six inches, and more than approximately twelve inches.

In many embodiments, the wafer table 16 is coupled to the XY-displacement table 22, which facilitates or enables the displacement of the wafer table 16 in a X- and a Y-direction. Displacement of the wafer table 16 correspondingly displaces the wafer 12 placed thereon. In many embodiments, the displacement of the wafer table 16, and hence displacement of the wafer 12 placed thereon, is controlled for controlling the positioning of the wafer 12 at the inspection position. The XY-displacement table 22 is alternatively known as an air-gap linear positioner. The XY-displacement table 22 or air-gap linear positioner facilitates high precision displacement of the wafer table 16 in the X- and Y-directions with minimal effect of vibration transmitted from the rest of the system 10 to the wafer table 16 and ensures smooth and accurate positioning of the wafer 12, or a portion thereof, at the inspection position.

In numerous embodiments, the XY-displacement table 22 and/or the wafer table 16 are mounted on the dampeners or vibration isolators 24 (as shown in FIG. 2) to absorb shocks or vibrations, applied to the XY-displacement table 22 and/or the wafer table 16, and to ensure flatness of the XY-displacement table 22 and/or the wafer table 16 as well as other modules or accessories mounted thereon.

It will be appreciated by a person skilled in the art that alternative mechanisms or devices may be coupled to or used with the wafer table 16 controlling the displacement thereof, and for facilitating high precision fine positioning of the wafer 12 at the inspection position.

In many embodiments of the present disclosure, the inspection of the wafer 12 for detecting possible defects thereon is performed while the wafer 12 is in motion. This is to say, the capture of images, for example brightfield images and darkfield images, of the wafer 12 occurs as the wafer 12 is being displaced across the inspection position. In some embodiments of the present disclosure, every new wafer 12 can be stopped under the imaging means to capture high-resolution images, if the user so chooses by programming the configuration table.

As previously mentioned, the system 10 includes the first tube lens 36 and the second tube lens 38. In several embodiments of the present disclosure, the first tube lens 36 is positioned or disposed between the objective lenses and the first image capture device 32. Illumination passes through the first tube lens 36 before entering the first image capture device 32. In several embodiments of the present disclosure, the second tube lens 38 is positioned between the objective lenses 40 and the second image capture device 34. Illumination passes through the second tube lens 38 and deflected by a mirror or prism 47 before entering the second image capture device 34.

In many embodiments, each of the number of objective lenses 40 has a corrected aberration in infinity. Accordingly, illumination or light received by the objective lens 40 is collimated thereby. Therefore, in many embodiments, illumination traveling between the objective lens 40 and each of the first tube lens 36 and second tube lens 38 is collimated. The collimation of illumination traveling between the objective lens 40 and each of the first tube lens 36 and the second tube lens 38 enhances ease and flexibility of positioning of each of the first image capture device 32 and the second image capture device 34 respectively. The implementation, or use, of the tube lenses 36, 38 also eliminates the need to refocus illuminations entering each of the first image capture device 32 and the second image capture device 34 when different objective lenses 40 are used. In addition, the collimation of illumination increases ease of introduction and positioning of additional optical components or accessories into the system 10, particularly between the objective lens 40 and each of the first tube lens 36 and the second tube lens 38. In most embodiments of the present disclosure, the collimation of illumination enables in-situ introduction and positioning of additional optical components or accessories into the system 10, particularly between the objective lens 40 and each of the first tube lens 36 and the second tube lens 38, without a need for reconfiguring the rest of the system 10. In addition, in several embodiments, the above arrangement helps to achieve longer working distance between objective lens 40 and the wafer 12 as compared to that used in existing equipment. Longer working distances between the objective lens 40 and the wafer 12 is typically necessary to use darkfield illuminations effectively.

It will therefore be appreciated by a person skilled in the art that the system 10 of the present disclosure allows for flexible and in-situ design and reconfiguration of components of the system 10. The system 10 of the present disclosure enhances ease of introduction and removal of optical components or accessories into and out of the system 10.

In many embodiments, the first tube lens 36 facilitates focusing of collimated illumination onto the first image capture plane. Similarly, in many embodiments, the second tube lens 38 facilitates focusing of collimated illumination onto the second image capture plane. In various embodiments, the first tube lens 36 is positioned such that the first image capture plane corresponds to a first focal length or distance associated with the first tube lens 36; and the second tube lens 38 is positioned such that the second image capture plane corresponds to a second focal length or distance associated with the second tube lens 38. Although, tube lenses 36, 38 are described for use with the system 10 of several embodiments of the present description, it will be appreciated by a person skilled in the art that alternative optical devices or mechanisms may be used for enabling collimation of illumination, more specifically the brightfield and darkfield illuminations, and the subsequent focusing thereof onto either of the first image capture plane and the second image capture plane respectively in other embodiments of the present disclosure.

In some embodiments of the present disclosure, the first image capture device 32 and the second image capture device 34 are positioned along adjacent parallel axes. The spatial positions of the first image capture device 32 and the second image capture device 34 are determined for reducing space occupied by the first image capture device 32 and the second image capture device 34 such that the system 10 occupies a smaller total area (i.e. is space-efficient).

In several embodiments of the present disclosure, the system 10 further includes a number of beam splitters and mirrors or reflective surfaces. The beam splitters and mirrors or reflective surfaces are positioned for directing and redirecting the brightfield illumination and the darkfield illuminations from each of the low angle darkfield illuminator 28 and high angle darkfield illuminator 30.

In most embodiments of the present disclosure, the system 10 further includes a central processing unit (CPU) (also known as a processing unit) with a storage memory or database (also known as a post processor) (not shown). The CPU is electrically communicatable with or coupled to the other components of the system 10, for example the first image capture device 32 and the second image capture device 34. In many embodiments of the present disclosure, images, or responses, captured by the first image capture device 32 and the second image capture device 34 are converted into image signals and transmitted to the CPU.

In many embodiments, the CPU is programmable for processing information, more specifically the image signals, transmitted thereto to thereby detect defects present on the wafer 12. In several embodiments of the present disclosure, the detection of defects on the wafer 12 is performed automatically by the system 10, and more specifically by the CPU. In some embodiments of the present disclosure, the inspection of wafers 12 by the system 10 is automatic, and controlled by the CPU. Alternatively, the inspection of wafers 12 for the detection of defects is facilitated by at least one manual input.

In many embodiments, the CPU is programmable for storing information transmitted thereto in a database. In addition, the CPU is programmable for classifying detected defects. In addition, the CPU is preferably programmed for storing processed information, more specifically the processed images and defects detected, in the database. Further details regarding capture of images, processing of captured images, and detection of defects on the wafers 12 are provided below.

It will be appreciated by a person skilled in the art, using the description provided above, that the brightfield illumination emitted from or supplied by the brightfield illuminator 26 and the darkfield illuminations emitted from each of the low angle darkfield illuminator 28 and the high angle darkfield illuminator 30 (hereinafter referred to as darkfield low angle or DLA illumination and darkfield high angle or DHA illumination respectively) each follows a different ray path or optical path.

Figure 10:
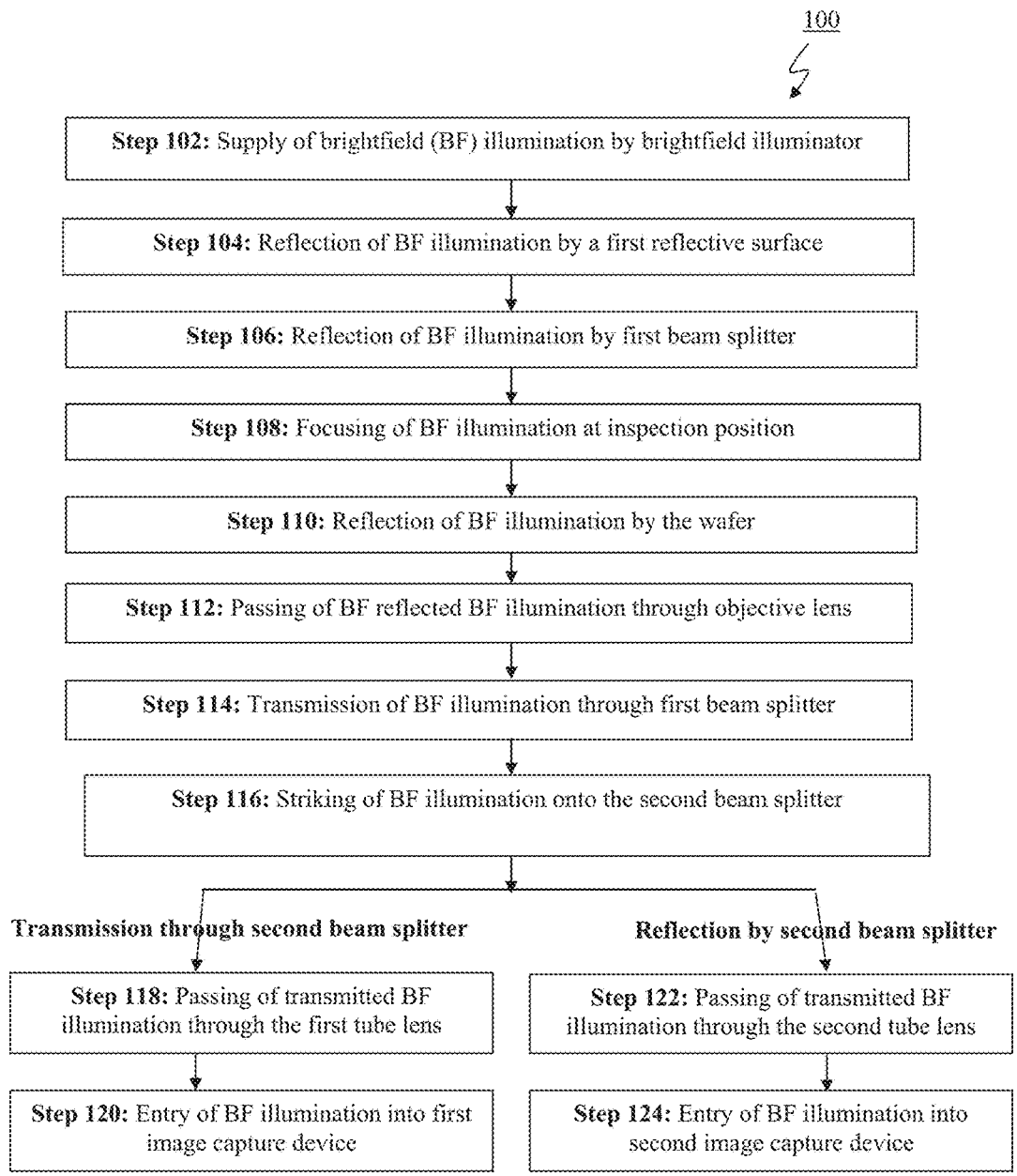
FIG. 10 is a flowchart of an exemplary first ray path followed by the brightfield illumination supplied by the brightfield illuminator of FIG. 9.

FIG. 10 shows a flowchart of an exemplary first ray path 100 followed by the brightfield illumination according to an embodiment of the present disclosure.

In a step 102 of the first ray path 100, brightfield illumination or light is supplied by the brightfield illuminator 26. As previously mentioned, the brightfield illumination can be emitted from the first optical fiber of the brightfield illuminator 26. The first optical fiber directs the brightfield illumination emitted from the brightfield illuminator 26. In several embodiments of the present disclosure, the brightfield illumination passes through a condenser 44. The condenser 44 concentrates the brightfield illumination.

In a step 104, the brightfield illumination is reflected by a first reflecting surface or a first mirror. Brightfield illumination reflected by the first reflecting surface is directed towards a first beam splitter 48.

The first beam splitter 48 reflects at least a portion of the brightfield illumination striking thereonto in a step 106. In several embodiments of the present disclosure, the first beam splitter 48 has a reflection/transmission (R/T) ratio of 30:70. It will however be understood by a person skilled in the art that the R/T ratio of the first beam splitter 48 can be adjusted as required for controlling the intensity or amount of brightfield illumination reflected or transmitted thereby.

The brightfield illumination reflected by the first beam splitter 48 is directed towards the inspection position. More specifically, the brightfield illumination reflected by the first beam splitter 48 is directed towards the objective lens 40 positioned directly above the inspection position. In a step 108, the brightfield illuminator 26 is focused by the objective lens 40, at the inspection position or the wafer 12 positioned at the inspection position.

Brightfield illumination supplied by the brightfield illuminator 26, and focused at the inspection position, illuminates the wafer 12, more specifically the portion of the wafer 12, positioned at the inspection position. In a step 110, the brightfield illumination is reflected by the wafer 12 positioned at the inspection position.

Brightfield illumination reflected by the wafer 12 passes through the objective lens 40 in a step 112. As previously mentioned, the objective lens 40 has a corrected aberration in infinity in most embodiments of the present invention. Brightfield illumination passing through the objective lens 40 is collimated by the objective lens 40. The degree of magnification of the brightfield illumination by the magnifying lens is dependent on the magnification factor of the objective lens 40.

Brightfield illumination passing through the objective lens 40 is directed towards the first beam splitter 48. In a step 114, the brightfield illumination strikes the first beam splitter 48 and a portion thereof is transmitted through the first beam splitter 48. Extent of the brightfield illumination transmitted through the first beam splitter 48 in the step 114 depends on the R/T ratio of the first beam splitter 48. Brightfield illumination transmitted through the first beam splitter 48 travels towards a second beam splitter 50.

In several embodiments of the present disclosure, the second beam splitter 50 of the system 10 is a cubic beam splitter 50 having a predetermined R/T ratio. In some embodiments of the present disclosure, the R/T ratio is 50/50. The R/T ratio may be varied as required. Use of the cubic beam splitter 50 is preferred because the cubic beam splitter 50 splits illumination received thereby into two optical paths. It will be appreciated by a person skilled in the art that the configuration and shape of the cubic beam splitter 50 will provide better performance and alignment for this purpose. Extent of illumination reflected or transmitted by the second beam splitter 50 is dependent on the R/T ratio of the second beam splitter 50. In a step 116, the brightfield illumination strikes the second beam splitter 50. The brightfield illumination striking the beam splitter is either transmitted therethrough or reflected thereby.

Brightfield illumination transmitted through the second beam splitter 50 travels towards the first image capture device 32. The brightfield illumination passes through the first tube lens 36 in a step 118 before entering the first image capture device 32 in a step 120. The first tube lens 36 helps to focus the collimated brightfield illumination onto the first image capture plane of the first image capture device 32. Brightfield illumination focused onto the first image capture plane enables capture of a brightfield image by the first image capture device 32.

The brightfield image captured by the first image capture plane is converted into image signals. The image signals are subsequently transmitted or downloaded to the CPU. The transmission of image signals to the CPU is also known as data transfer. Transferred brightfield images are then at least one of processed by and stored in the CPU.

Brightfield illumination reflected by the second beam splitter 50 travels towards the second image capture device 34. The brightfield illumination passes through the second tube lens 38 in a step 122 before entering the second image capture device 34 in a step 124. The second tube lens 38 helps to focus the collimated brightfield illumination onto the second image capture plane. Brightfield illumination focused onto the second image capture plane enables capture of a brightfield image by the second image capture device 34.

The brightfield image captured by the second image capture plane is converted into image signals. The image signals are subsequently transmitted or downloaded to the CPU. The transmission of image signals to the programmable controller is also known as data transfer. Transferred brightfield images are then at least one of processed by and stored in the CPU.

Figure 11:
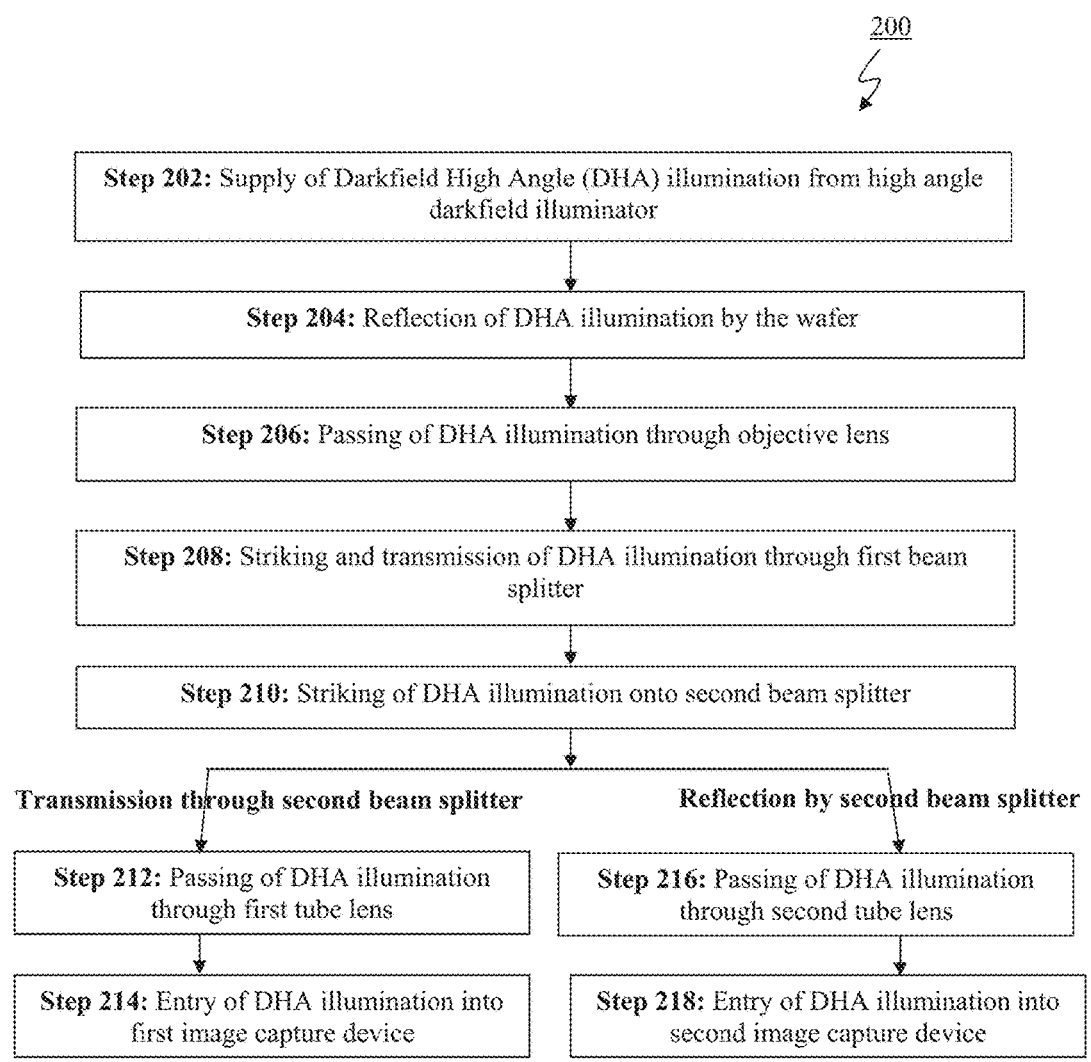
FIG. 11 is a flowchart of an exemplary second ray path followed by the darkfield high angle illumination supplied by the high angle darkfield illuminator of FIG. 9.

FIG. 11 shows a flowchart of an exemplary second ray path 200 followed by the darkfield high angle (DHA) illumination according to an embodiment of the present disclosure.

In a step 202 of the second ray path 200, DHA illumination is supplied by the high angle darkfield illuminator 30. As previously mentioned, the second optical fiber helps to direct the DHA illumination supplied from the high angle darkfield illuminator 30. In several embodiments of the present disclosure, the DHA illumination is directly focused at the inspection position without a need to pass through optical components or accessories, for example the objective lens 40.

In a step 204, DHA illumination directed at the inspection position is reflected by the wafer 12, or the portion thereof, positioned at the inspection position. Reflected DHA illumination from the wafer passes through the objective lens 40 in a step 206. The objective lens 40, which has a corrected aberration in infinity, collimates the DHA illumination passing therethrough in the step 206.

DHA illumination passing through the objective lens 40 is directed towards the first beam splitter 48. In a step 208, the DHA illumination strikes the first beam splitter 48 and a portion thereof is transmitted through the first beam splitter 48. The extent of transmission of the DHA illumination through the first beam splitter 48 is dependent on the UT ratio of the first beam splitter 48.

DHA illumination transmitted through the first beam splitter 48 is directed towards the second beam splitter 50. In a step 210, the DHA illumination strikes the second beam splitter 50. Transmission or reflection of the DHA illumination striking the second beam splitter 50 is dependent on the R/T ratio of the second beam splitter 50.

DHA illumination transmitted through the second beam splitter 50 passes through the first tube lens 36 in a step 212 before entering the first image capture device 32 in a step 214. The first tube lens 36 helps to focus the collimated DHA illumination onto the first image capture plane of the first image capture device 32. DHA illumination focused onto the first image capture plane enables capture of a darkfield image, more specifically a darkfield high angle (DHA) image by the first image capture device 32.

Alternatively, DHA illumination is reflected by the second beam splitter 50. Reflected DHA illumination, from the second beam splitter 50, passes through the second tube lens 38 in a step 216 before entering the second image capture device 34 in a step 218. The second tube lens 38 helps to focus the collimated DHA illumination onto the second image capture plane of the second image capture device 34. DHA illumination focused onto the second image capture place enables capture of a darkfield image, more specifically a darkfield high angle (DHA) image by the second image capture device 34.

Figure 12:
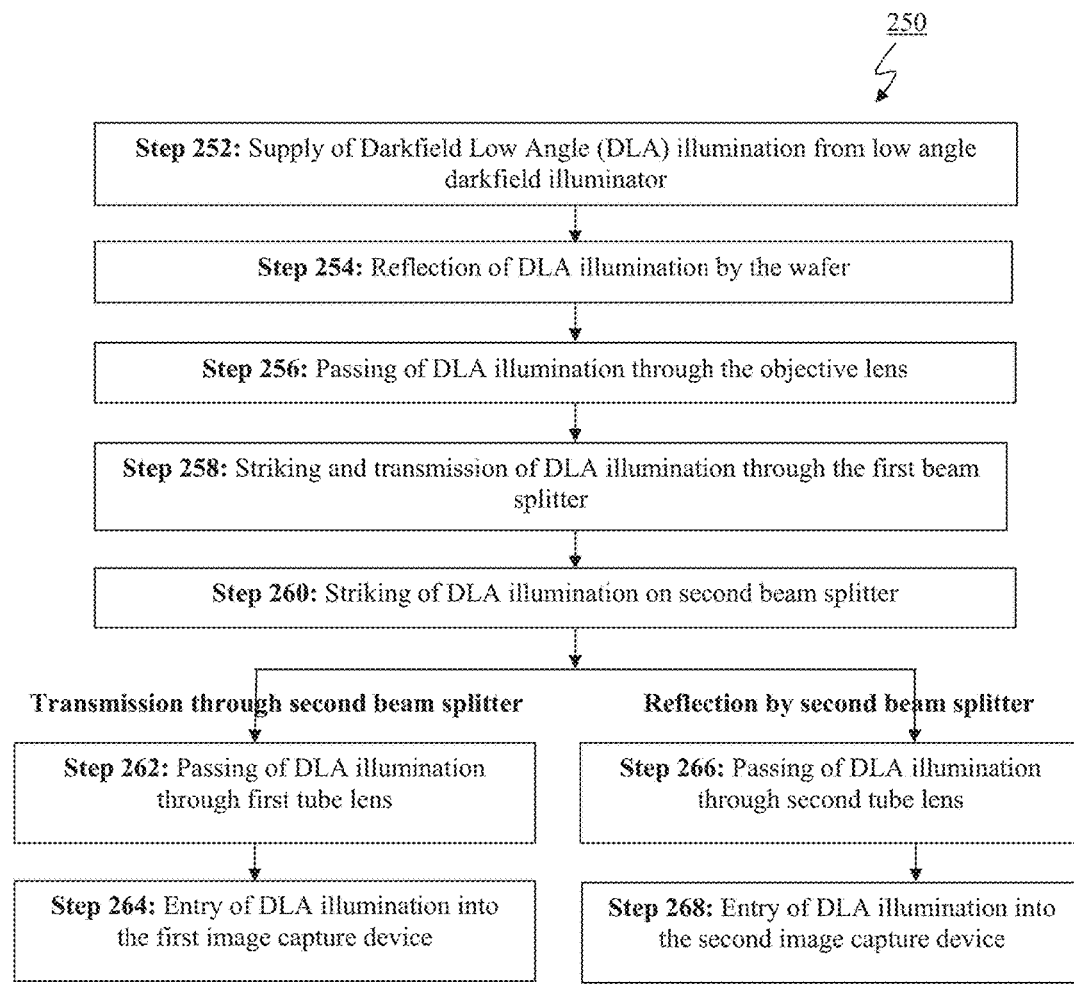
FIG. 12 is a flowchart of an exemplary third ray path followed by the darkfield low angle illumination supplied by the low angle darkfield illuminator of FIG. 9.

FIG. 12 shows a flowchart of an exemplary third ray path 250 followed by the darkfield low angle (DLA) illumination according to an embodiment of the present disclosure.

In a step 252 of the third ray path 200, DLA illumination is supplied by the low angle darkfield illuminator 28. The third optical fiber helps to direct the DLA illumination supplied by the low angle darkfield illuminator 28. In several embodiments of the present disclosure, the DLA illumination is directly focused at the inspection position without a need to pass through optical components or accessories, for example the objective lens 40.

In a step 254, DLA illumination directed at the inspection position is reflected by the wafer 12, or the portion thereof, positioned at the inspection position. Reflected DLA illumination from the wafer passes through the objective lens 40 in a step 256. The objective lens 40, which has a corrected aberration in infinity, collimates the DLA illumination passing therethrough in the step 256.

DLA illumination passing through the objective lens 40 is directed towards the first beam splitter 48. In a step 258, the DLA illumination strikes the first beam splitter 48 and a portion thereof is transmitted through the first beam splitter 48. The extent of transmission of the DLA illumination through the first beam splitter 48 is dependent on the R/T ratio of the first beam splitter 48.

DLA illumination transmitted through the first beam splitter 48 is directed towards the second beam splitter 50. In a step 260, the DLA illumination strikes the second beam splitter 50. Transmission or reflection of the DLA illumination striking the second beam splitter 50 is dependent on the R/T ratio of the second beam splitter 50.

DLA illumination transmitted through the second beam splitter 50 passes through the first tube lens 36 in a step 262 before entering the first image capture device 32 in a step 264. The first tube lens 36 helps to focus the collimated DLA illumination onto the first image capture plane of the first image capture device 32. DLA illumination focused onto the first image capture plane enables capture of a darkfield image, more specifically a darkfield low angle (DLA) image by the first image capture device 32.

Alternatively, DLA illumination is reflected by the second beam splitter 50. Reflected DLA illumination from the second beam splitter 50, passes through the second tube lens 38 in a step 266 before entering the second image capture device 34 in a step 268. The second tube lens 38 helps to focus the collimated DLA illumination onto the second image capture plane of the second image capture device 34. DLA illumination focused onto the second image capture plane enables capture of a darkfield image, more specifically a darkfield low angle (DLA) image by the second image capture device 34.

It will be appreciated by a person skilled in the art from the description provided above that the DHA illumination and DLA illumination follows a similar ray path after being reflected by the wafer 12 in several embodiments of the present disclosure. However, the second ray path 200 of the DHA illumination and the third ray path 250 of the DLA illumination can alternatively be individually altered as required using techniques known in the art. In addition, in some embodiments of the present disclosure, the angles at which the DHA illumination and the DLA illumination strike at wafer 12 positioned at the inspection position can be adjusted as required for enhancing accuracy of defect detection. For example, in some embodiments of the present disclosure, the angles at which the DHA illumination and the DLA illumination strike at wafer 12 positioned at the inspection position may be adjusted depending on type of wafer 12 positioned at the inspection position or type of wafer defect that a user of the system 10 wishes to detect.

The DHA images and the DLA images capture by each of the first image capture device 32 and the second image capture device 34 is preferably converted into image signals, which are subsequently transmitted or downloaded to the CPU. The transmission of image signals to CPU is also known as data transfer. Transferred DHA images and DLA images can then be at least one of processed by and stored in the CPU as required.

In many embodiments of the present disclosure, the first image capture device 32 and the second image capture device 34 have predetermined spatial positions relative to each other. The use of the objective lens 40 together with the first tube lens 36 and the second tube lens 38 facilitates the spatial positioning of the first image capture device 32 and the second image capture device 34. It will further be appreciated by a person skilled in the art that other optical components or accessories, for example mirrors, may be used for directing the brightfield illumination, DHA illumination and DLA illumination, and for facilitating the spatial positioning of the first image capture device 32 and the second image capture device 34. In most embodiments of the present disclosure, the spatial positions of the first image capture device 32 and the second image capture device 34 are fixed with reference to the inspection position. The fixed spatial positions of the first image capture device 32 and the second image capture device 34 helps to enhance at least one of the accuracy and the efficiency of wafer inspection by the system 10. For example, the fixed spatial positions of the first image capture device 32 and the second image capture device 34 with respect to the inspection position preferably reduces calibration losses and adjustment feedback losses typically associated with the use of mobile image capture devices or cameras.

In many embodiments of the present disclosure, the system 10 includes a number of third illuminators 52, hereinafter referred to as thin line illuminators 52.

Figure 13:
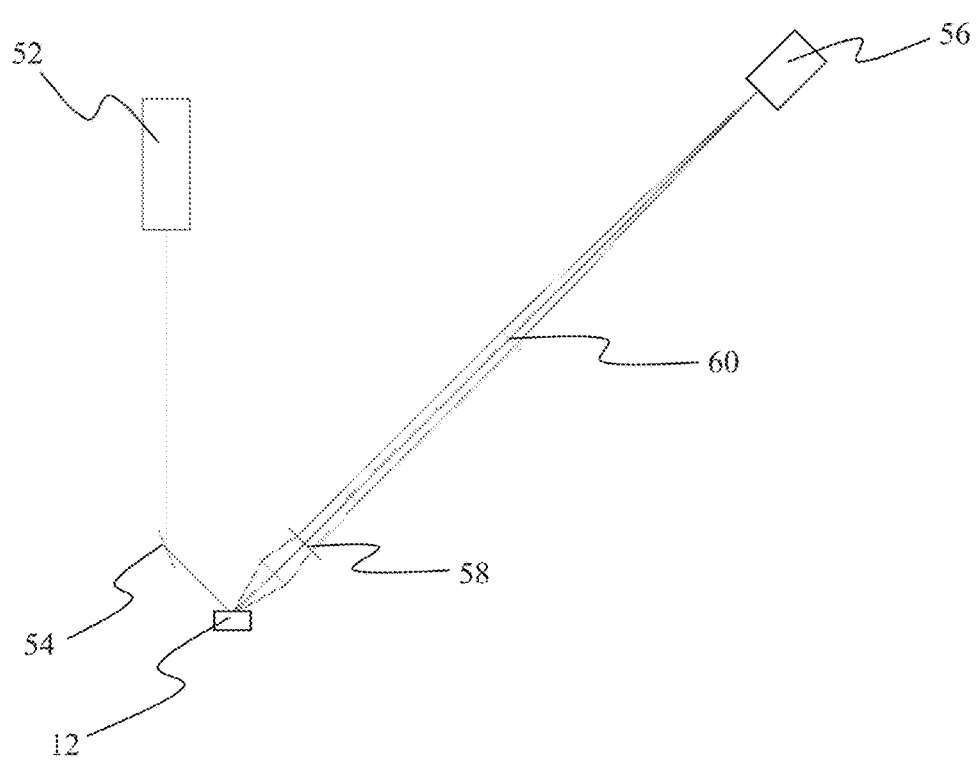
FIG. 13 shows ray path of illumination between a thin line illuminator and a 3D image capture device or camera of a system in accordance with an embodiment of the present disclosure.
Figure 27A:
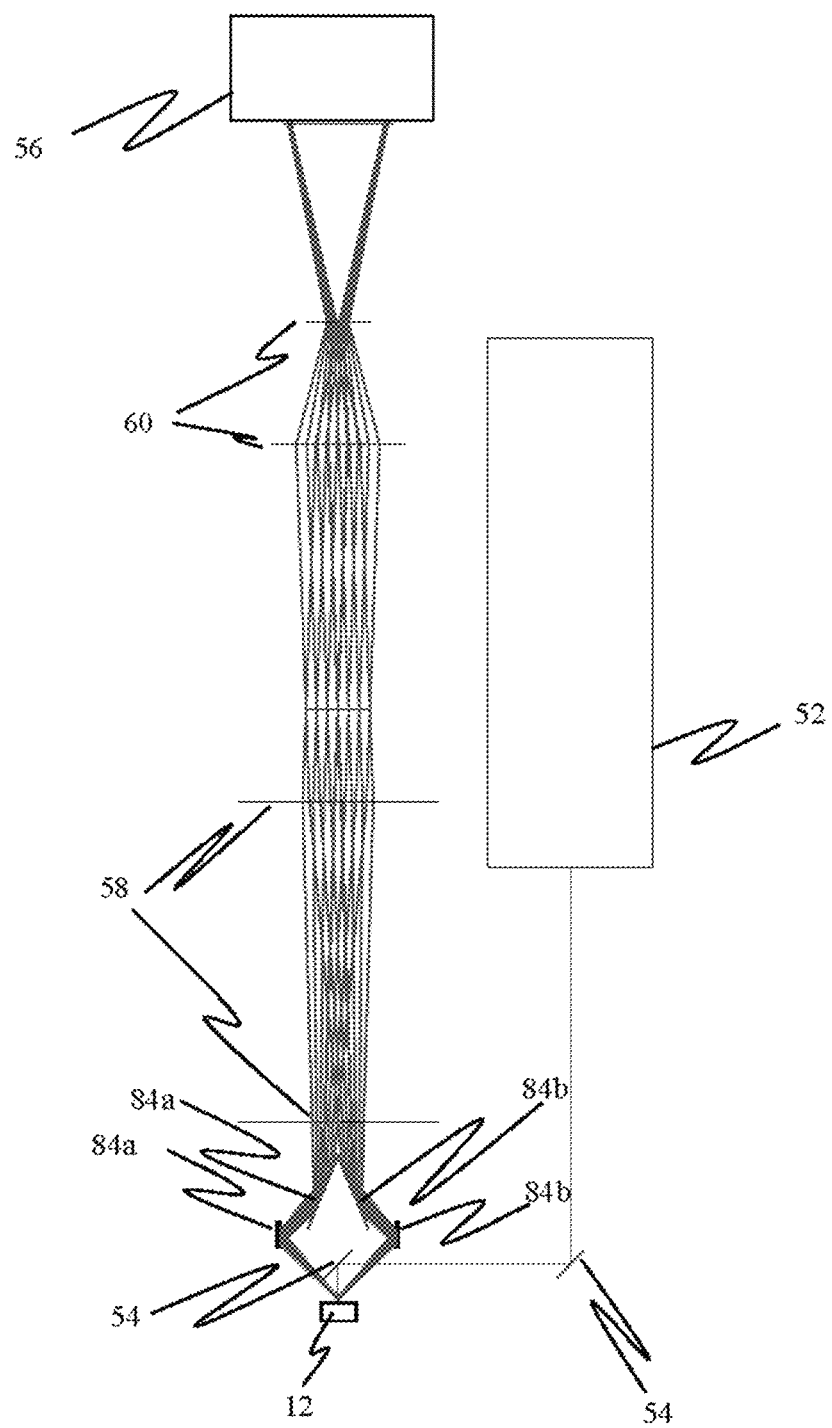
FIG. 27a shows an exemplary optical ray path of illumination between a thin line illuminator and a 3D image capture device or camera according to an embodiment of the present disclosure.
Figure 27B:
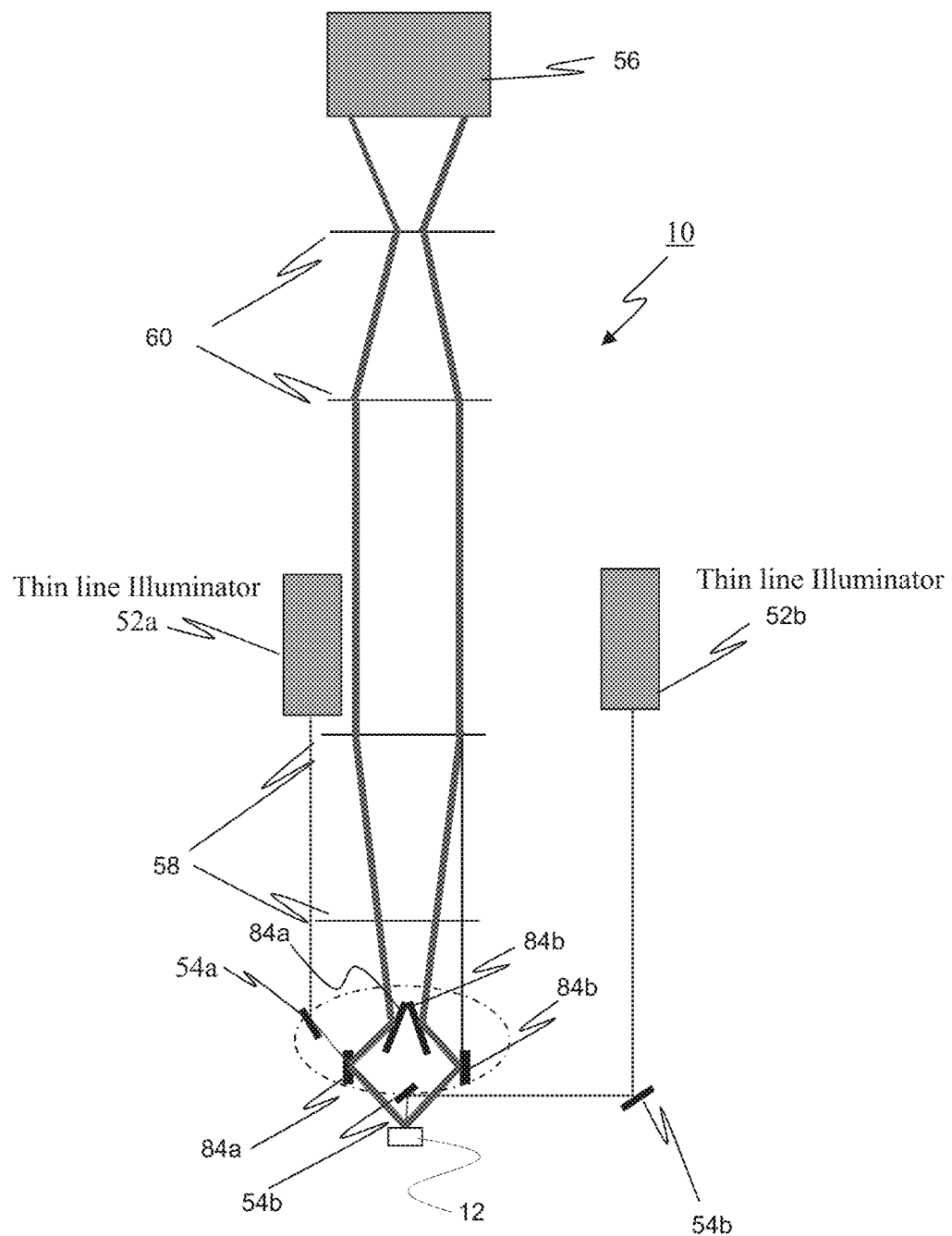
FIG. 27b shows another optical ray path of illumination between two thin line illuminators and a 3D image capture device or camera according to another embodiment of the present disclosure.
Figure 27C:
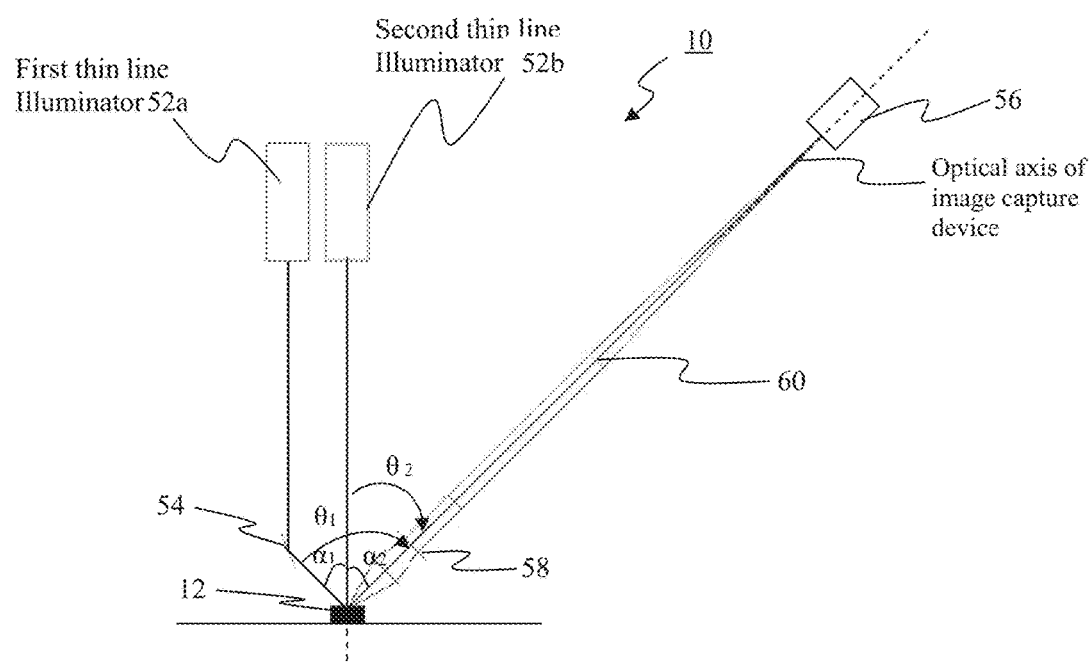
FIG. 27c shows another optical ray path of illumination between two thin line illuminators and a 3D image capture device or camera according to another embodiment of the present disclosure.

In some embodiments, for example as shown in FIGS. 13 and 27a, the system 10 includes one thin line illuminator 52. In other embodiments, for example as shown in FIGS. 27b and 27c, the system includes two thin line illuminators 52, namely a first thin line illuminator 52a and a second thin line illuminator 52b. It will be understood by a person of ordinary skill in the art that the system 10 can include alternative numbers of thin line illuminators 52, for example three, four, five, or more thin line illuminators 52 within the scope of the present disclosure.

The thin line illuminator(s) 52 supplies thin line illumination. In several embodiments of the present disclosure, the thin line illuminator(s) 52 can be a laser source for supplying thin line laser illumination. In other embodiments of the present disclosure, the thin line illuminator(s) 52 can be a broadband illuminator supplying a broadband thin line illumination.

The wavelengths of the thin line illumination supplied or emitted by the thin line illuminator(s) 52 can be controlled (e.g., selected and/or varied), for example depending upon characteristics, properties, and/or topographical features of the wafer 12 to be inspected.

In some embodiments wherein the system 10 includes two or more thin line illuminators 52 (e.g., the first thin line illuminator 52a and the second thin line illuminator 52b), the wavelengths of the thin line illumination supplied by the thin line illuminators 52 can be similar, or substantially similar. However, in other embodiments wherein the system 10 includes two or more thin line illuminators 52 (e.g., the first thin line illuminator 52a and the second thin line illuminator 52b), the wavelengths of the thin line illumination supplied by the thin line illuminators 52 are different, or substantially different, from each other.

In addition, in particular embodiments wherein the system 10 includes two or more thin line illuminators 52 (e.g., the first thin line illuminator 52a and the second thin line illuminator 52b), the relative intensities of the thin line illumination supplied by each of the thin line illuminators 52 can be either similar or different from each other. In various embodiments, the relative intensities of the thin line illumination supplied by each of the thin line illuminators can be controlled (e.g., selected and/or varied), for example depending upon characteristics, properties, and/or topographical features of the wafer 12 to be inspected.

In many embodiments of the present disclosure, thin line illumination supplied or emitted by the thin line illuminator(s) is directed to or toward an inspection position.

In accordance with various embodiments of the disclosure, an inspection position can be defined as a wafer, substrate, or object surface position or location, and/or a wafer table position, that is currently under consideration for the capture of reflected or redirected illumination signals during an inspection process. An inspection position can correspond to a current X-Y (and possibly θ) location on a wafer, substrate, or object surface; and/or a current X-Y (and possibly θ) position established by the wafer table 16 that carries a wafer, substrate, or other object. An inspection position can additionally or alternatively be defined as a discrete location or particular set of spatial coordinates (e.g., X-Y-θ) currently under consideration for inspection along a wafer scan motion path, where the wafer scan motion path establishes a sequence of spatial positions through which the wafer 12 is moved or translated (e.g., by way of continuous motion in the case of "on-the-fly" inspection) during an inspection process. Thus, an inspection position can be defined as a spatial position (e.g., given by a set of X-Y-θ coordinates) along a wafer scan motion path at which illumination that interacts with a wafer's surface is captured (e.g., by an image capture device 56).

The thin line illumination is directed at the inspection position at a predetermined angle, which can be determined and varied, for instance depending on function(s) of the system 10.

In several embodiments of the present disclosure, the system 10 includes at least one set of mirrors 54 (also known as a mirror setup 54 or a mirror assembly 54) that is disposed and configured to direct the thin line illumination at the inspection position. In many embodiments, where the system 10 includes one thin line illuminator 52, the system 10 correspondingly includes one set of mirrors 54 that is disposed and configured to direct the thin line illumination supplied by the thin line illuminator 52 at the inspection position. Likewise, in many embodiments wherein a system 10 includes multiple thin line illuminators 52, for instance the first thin line illuminator 52a and the second thin line illuminator 52b as shown in FIG. 27b, the system 10 includes multiple sets of mirrors 54, for instance a first set of mirrors 54a and a second set of mirrors 54b, disposed and configured to direct the thin line illumination supplied by both thin line illuminators 52a, 52b at the inspection position.

In numerous embodiments, each set of mirrors 54 includes a number of reflective surfaces, or mirrors, that are configured, arranged, and/or disposed to direct thin line illumination towards the inspection position. The configuration of each mirror relative each other can be determined and varied, for instance depending upon function(s) or characteristic(s) of the system 10.

In various embodiments, the sets of mirrors 54, for instance the first set of mirrors 54a and the second set of mirrors 54b, are disposed or arranged in substantially symmetrical configuration. Alternatively, the sets of mirrors 54 can be positioned or arranged in other configurations, for instance depending upon function(s) of the system 10 or size of available space for placement of the system 10.

In many embodiments, the optical inspection head 14 of the system 10 includes a third image capture device (hereinafter referred to as a three-dimensional (3D) profile camera 56). In numerous embodiments, the 3D profile camera 56 receives thin line illumination that is reflected by the wafer 12, more specifically a surface of the wafer 12 positioned at the inspection position.

In some embodiments, for example as shown in FIG. 27a and FIG. 27b, the system 10 includes a number of sets of reflectors 84 (also known as reflector assemblies or reflector setups), for example one, two, three, four, or more sets of reflectors 84, for directing thin line illumination reflected off the surface of the wafer 12 towards the 3D profile camera 56.

In most embodiments, each set of reflectors 84 is shaped, configured, and/or disposed for directing thin line illumination reflected off the surface of the wafer 12 towards the 3D profile camera 56.

In several embodiments, the number of sets of reflectors 84 of a system 10 corresponds to the number of thin line illuminators 52 of the system 10. Accordingly, where a system 10 includes two thin line illuminators 52, for instance the first and second thin line illuminators 52a, 52b, the system 10 also includes two sets of reflectors 84, for instance a first set of reflectors 84a and a second set of reflectors 84b. In other embodiments, the number of sets of reflectors 84 of a system 10 is not dependent on the number of thin line illuminators 52 of the system 10.

In many embodiments, each set of reflectors 84 includes a number of reflective surfaces or mirrors, for example two, three, four, or more reflective surfaces, that are shaped, configured, and/or disposed for directing thin line illumination towards the 3D profile camera 56. In various embodiments, the set of reflectors 84 can include a prism assembly (not shown) that is shaped, configured, and/or disposed for directing thin line illumination towards the 3D profile camera 56. A prism assembly can include at least one optical prism configured to receive illumination, and (re)direct such received illumination along one or more intended optical travel paths or direction by way of optical refraction and/or dispersion.

In numerous embodiments, each set of reflectors 84 is disposed to receive thin line illumination reflected off the surface of the wafer 12 in a specific direction. For example, the first set of reflectors 84a can be disposed to receive thin line illumination reflected off the surface of the wafer 12 in a first direction and the second set of reflectors 84b can be disposed to receive thin line illumination reflected off the surface of the wafer 12 in a second direction, wherein the first direction is different from the second direction. In embodiments where the system 10 includes other numbers of sets reflectors 84, said sets of reflectors 84 can be disposed to receive illumination reflected off the surface of the wafer in a corresponding number of directions.

In various embodiments, for example as shown in FIG. 27c, the system 10 does not include the set of reflectors 84 (or reflector assemblies) for directing thin line illumination reflected and/or scattered off the surface of the wafer 12 towards the 3D profile camera 56. Representative manners in which such illumination can be reflected or scattered by the wafer's surface are described in detail below. Thin line illumination reflected and/or scattered off the surface of the wafer 12 is directly captured by the 3D profile camera 56, which can be positioned and/or configured for capturing said thin line illumination.

In several embodiments of the present disclosure, the optical inspection head 14 further includes an objective lens or objective lens assembly (hereinafter referred to as a 3D profile objective lens 58) for use with the 3D profile camera 56 or 3D image capture device. In many embodiments, thin line illumination reflected off the surface of the wafer 12 passes through the 3D profile objective lens 58 before entering the 3D profile camera 56. In many embodiments, the 3D profile objective lens 58 has a corrected aberration in infinity. Accordingly, thin line illumination passing through the 3D profile objective lens 58 is collimated thereby.

In some embodiments, the optical inspection head 14 further includes a tube lens 60 for use with the 3D profile objective lens 58 and the 3D profile camera 56. The tube lens 60 is shaped and configured to facilitate or enable focusing of the collimated thin line illumination onto the 3D image capture plane of the 3D profile camera 56.

In various embodiments, the use of the tube lens 60 with the 3D profile objective lens 58 and the 3D profile camera 56 facilitates flexible positioning and reconfiguration of the 3D profile camera 56. In addition, in particular embodiments, the use of the tube lens 60 with the 3D profile objective lens 58 and the 3D profile camera 56 enables ease of introducing additional optical components or accessories between the 3D profile objective lens 58 and the tube lens 60.

In many embodiments, the thin line illuminator(s) 52 and the 3D profile camera 56 operate cooperatively for facilitating 3D profile scanning and inspection of the wafer 12. This is also to say, the use of the thin line illuminator(s) 52 and the 3D profile camera 56 are used together for obtaining information on the 3D characteristics (or topology) of the surface of wafers 12.

In many embodiments of the present disclosure, the thin line illuminator(s) 52 and the 3D profile camera 56 are coupled to the CPU (or processing unit), which helps to coordinate or synchronize the operation of the thin line illuminator 52 and the 3D profile camera 56. In several embodiments, an automated 3D profile scanning and inspection of the wafer 12 is performed by the system 10. This automated 3D profile scanning and inspection of the wafer 12 can be controlled by the CPU.

In several embodiments of the present disclosure, the optical inspection head 14 includes a review image capture device 62. The review image capture device 62 is for example a color camera. In some embodiments, the review image capture device 62 captures color images. In other embodiments, the review image capture device 62 captures monochromatic images. In various embodiments, the review image capture device 62 captures review images of the wafer 12 for at least one of confirming, classifying, and reviewing defect(s) detected on the wafer 12.

Figure 14:
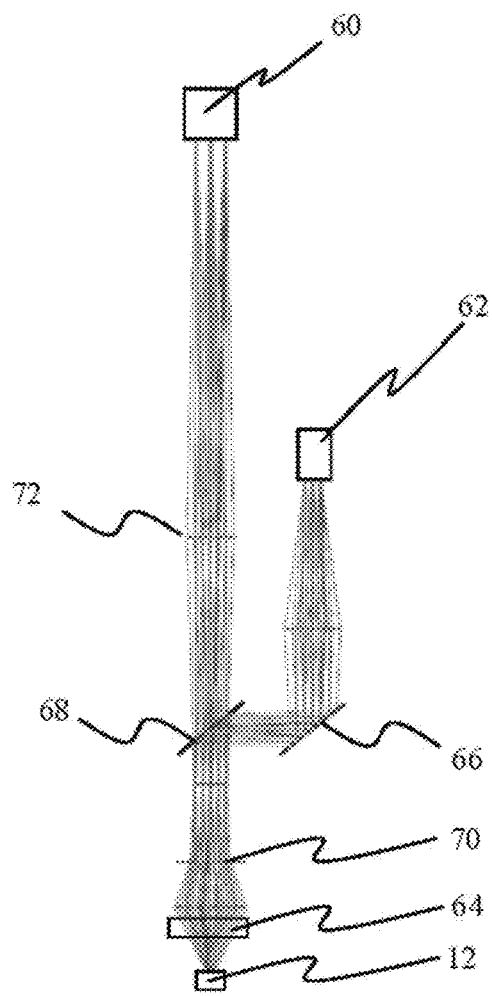
FIG. 14 shows optical ray path of illumination between a review brightfield illuminator, a review darkfield illuminator and a review image capture device of the system of FIG. 1.

FIG. 14 shows a review brightfield illuminator 64, a review darkfield illuminator 66, a review image capture device 62, and illumination patterns therebetween according to particular embodiments of the present disclosure.

In several embodiments of the present disclosure, the optical inspection head 14 further includes, or carries, the review brightfield illuminator 64 and the review darkfield illuminator 66 for supplying brightfield illumination and darkfield illumination respectively.

The review image capture device 62 receives the brightfield illumination and the darkfield illumination supplied by the review brightfield illuminator 64 and the review darkfield illuminator 66 respectively, and reflected by the wafer 12, for capturing review images of the wafer 12. In other embodiments of the present disclosure, the review image capture device 62 captures illumination supplied by alternative illuminators, for example one of that described above, for capturing review images of the wafer 12. The review image capture device 62 can capture high-resolution images of the wafer 12.

Figure 15:
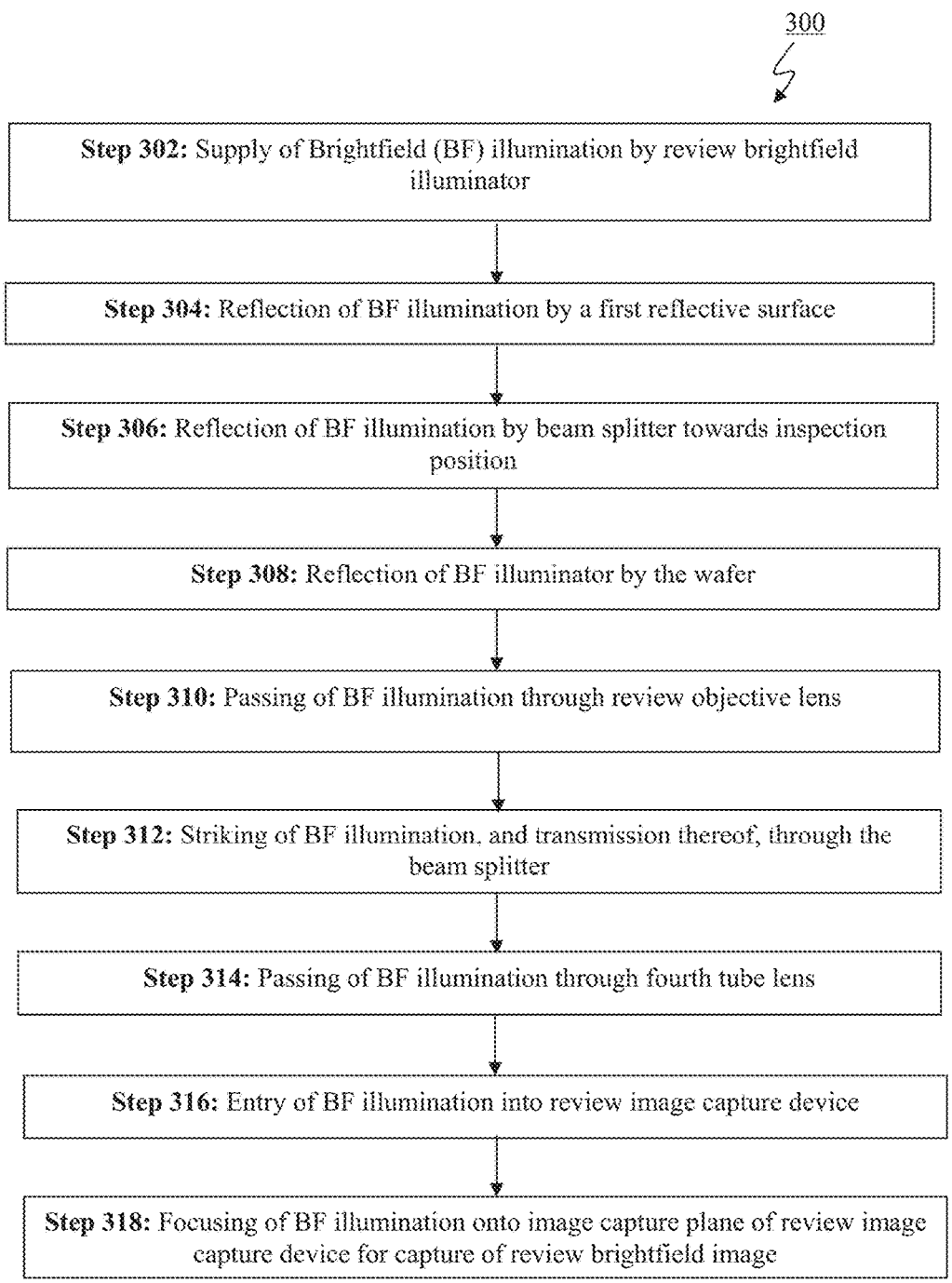
FIG. 15 is a flowchart of an exemplary fourth ray path followed by brightfield illumination between the review brightfield illuminator and the review image capture device of FIG. 14.

FIG. 15 shows a flowchart of an exemplary fourth ray path 300 followed by the brightfield illumination supplied by the review brightfield illuminator 64 as according to various embodiments of the present disclosure.

In a step 302 of the fourth ray path 300, brightfield illumination is supplied by the review brightfield illuminator 64. The brightfield illumination supplied by the review brightfield illuminator 64 is directed at a first reflective surface 74. In a step 304, the brightfield illumination is reflected by the first reflective surface 74 and directed towards a beam splitter 68. In a subsequent step 306, the brightfield illumination striking the beam splitter 68 is reflected thereby and directed towards the inspection position. Extent of brightfield illumination reflected by the beam splitter 68 depends on R/T ratio thereof.

In a step 308, the brightfield illumination is reflected by the wafer 12, or portion thereof, positioned at the inspection position. The reflected brightfield illumination passes through a review objective lens 70 in a step 310. In most embodiments of the present disclosure, the review objective lens 70 has a corrected aberration in infinity. Accordingly, the brightfield illumination passing through the review objective lens 70 in the step 310 is collimated by the review objective lens 70.

In a step 312, the brightfield illumination strikes the beam splitter 68 and a portion thereof is transmitted therethrough. Extent of the brightfield illumination passing through the beam splitter 68 is depending on the R/T ratio of the beam splitter 68. The brightfield illumination then passes through a review tube lens 72 in a step 314 before entering the review image capture device 62 in a step 316. The review tube lens 72 focuses the collimated brightfield illumination onto an image capture plane of the review image capture device 62. Brightfield illumination focused on the image capture plane of the review image capture device 62 facilitates capture of review brightfield images in a step 318.

The collimation of the brightfield illumination between the review objective lens 70 and the review tube lens 72 facilitates ease of introduction of optical components and accessories therebetween. In addition, the collimation of the brightfield illumination between the review objective lens 70 and the review tube lens 72 preferably enables flexible positioning and reconfiguration as required of the review image capture device 62.

Figure 16:
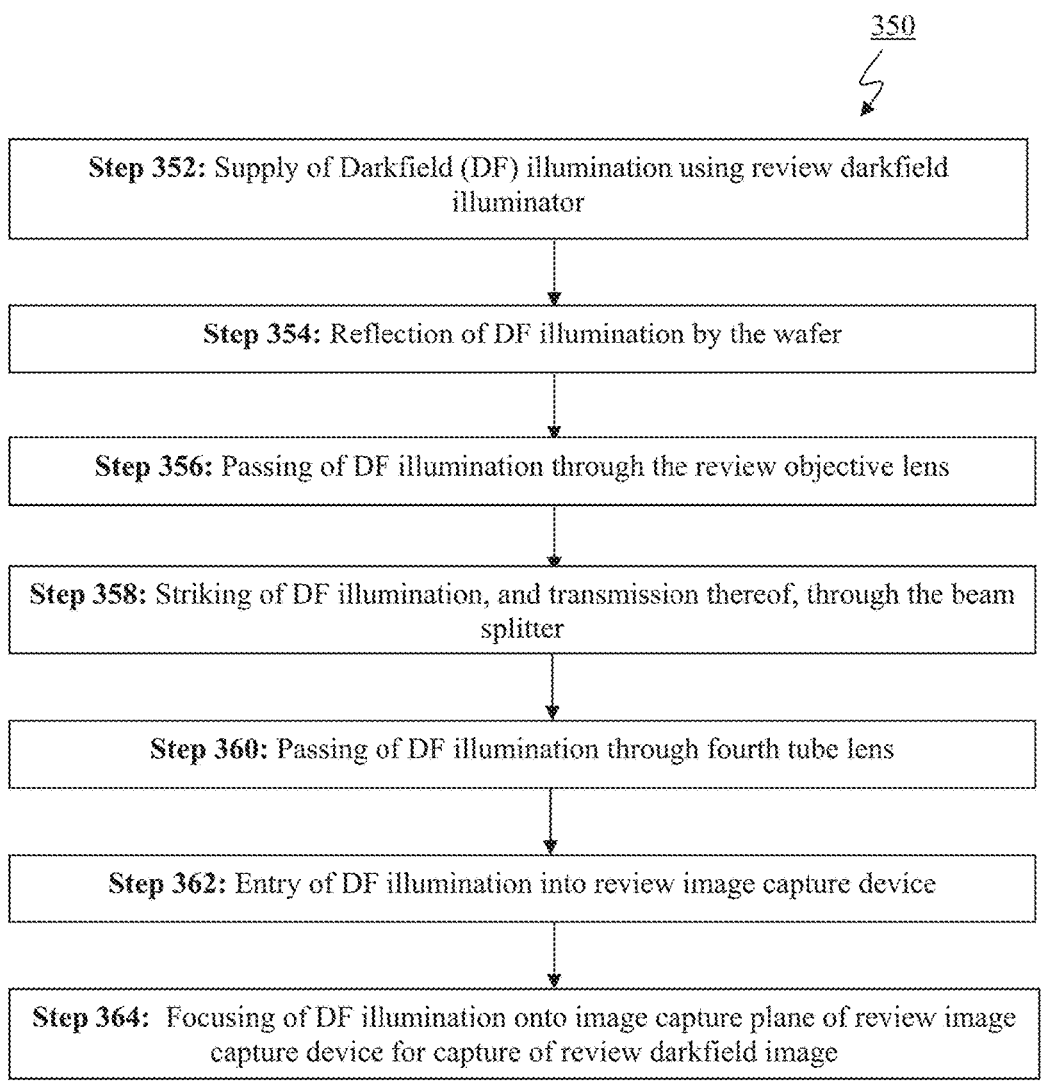
FIG. 16 is a flowchart of an exemplary fifth ray path followed by darkfield illumination between the review darkfield illuminator and the review image capture device of FIG. 14.

FIG. 16 shows a flowchart of an exemplary fifth ray path 350 followed by the darkfield illumination supplied by the review darkfield illuminator 66 according to an embodiment of the present disclosure.

In a step 352 of the fifth ray path 350, darkfield illumination is supplied by the review darkfield illuminator 66. In several embodiments of the present disclosure, the darkfield illumination supplied by the review darkfield illuminator 66 is directly focused at the inspection position. In some embodiments of the present disclosure, the darkfield illumination supplied by the review darkfield illuminator 66 is directed at the inspection position at a predetermined angle to a horizontal plane of the wafer 12. This predetermined angle is preferably a high angle, and can be adjusted as required using techniques known to a person skilled in the art.

In a step 354, the darkfield illumination is reflected by the wafer 12, or portion thereof, positioned at the inspection position. The reflected darkfield illumination then passes through the review objective lens 70 in a step 356. The darkfield illumination passing through the review objective lens 70 in the step 356 is collimated by the review objective lens 70.

In a step 358, the collimated darkfield illumination strikes the beam splitter and a portion thereof is transmitted therethrough. Extent of the darkfield illumination passing through the beam splitter 68 is depending on the R/T ratio of the beam splitter 68. The darkfield illumination then passes through the review tube lens 72 in a step 360 before entering the review image capture device 62 in a step 362. The fourth tube lens 72 focuses the collimated darkfield illumination onto an image capture plane of the review image capture device 62. Darkfield illumination focused on the image capture plane of the review image capture device 62 facilitates capture of review darkfield images in a step 364. The collimation of each of the brightfield illumination and darkfield illumination between the review objective lens 70 and the review tube lens 72 enhances ease of design and configuration of the system 10. More specifically, the collimation of each of the brightfield illumination and darkfield illumination between the review objective lens 70 and the review tube lens 72 enhances ease of positioning or configuration of the review image capture device 62 with the other components of the system 10, thereby facilitating capture, while the wafer 12 is in motion, of the review brightfield images and review darkfield images.

Captured review brightfield images and captured review darkfield images are converted into image signals and transmitted from the review image capture device 62 to the programmable controller where they can be processed, and stored or saved in the database.

The review image capture device 62 can have a fixed spatial position relative the inspection position. The fixed spatial position of the review image capture device 62 preferably reduces calibration losses and adjustment feedback losses typically associated with the use of mobile image capture devices or cameras, thereby enhancing quality of review brightfield images and review darkfield images captured.

In several embodiments of the present disclosure, the system 10 further includes a number of vibration isolators 24, which are collectively known as a stabilizer mechanism. The system 10 can be mounted on the vibration isolators 24 or stabilizer mechanism when the system is in normal operation. In several embodiments of the present disclosure, the system 10 includes four vibration isolators 24, each positioned at a different corner of the system 10. The vibration isolators 24 help to support and stabilize the system 10. In some embodiments of the present disclosure, each vibration isolator 24 is a compressible structure or canister, which absorbs ground vibrations to thereby serve as a buffer for preventing transmission of ground vibrations to the system 10. By preventing unwanted vibrations or physical movements to the system 10, the vibration isolators 24 help to enhance quality of images captured by each of the first image capture device 32, the second image capture device 34, the 3D profile camera 56, and the review camera 62, and to thereby improve quality of inspection of the wafer 12.

Figure 17A:
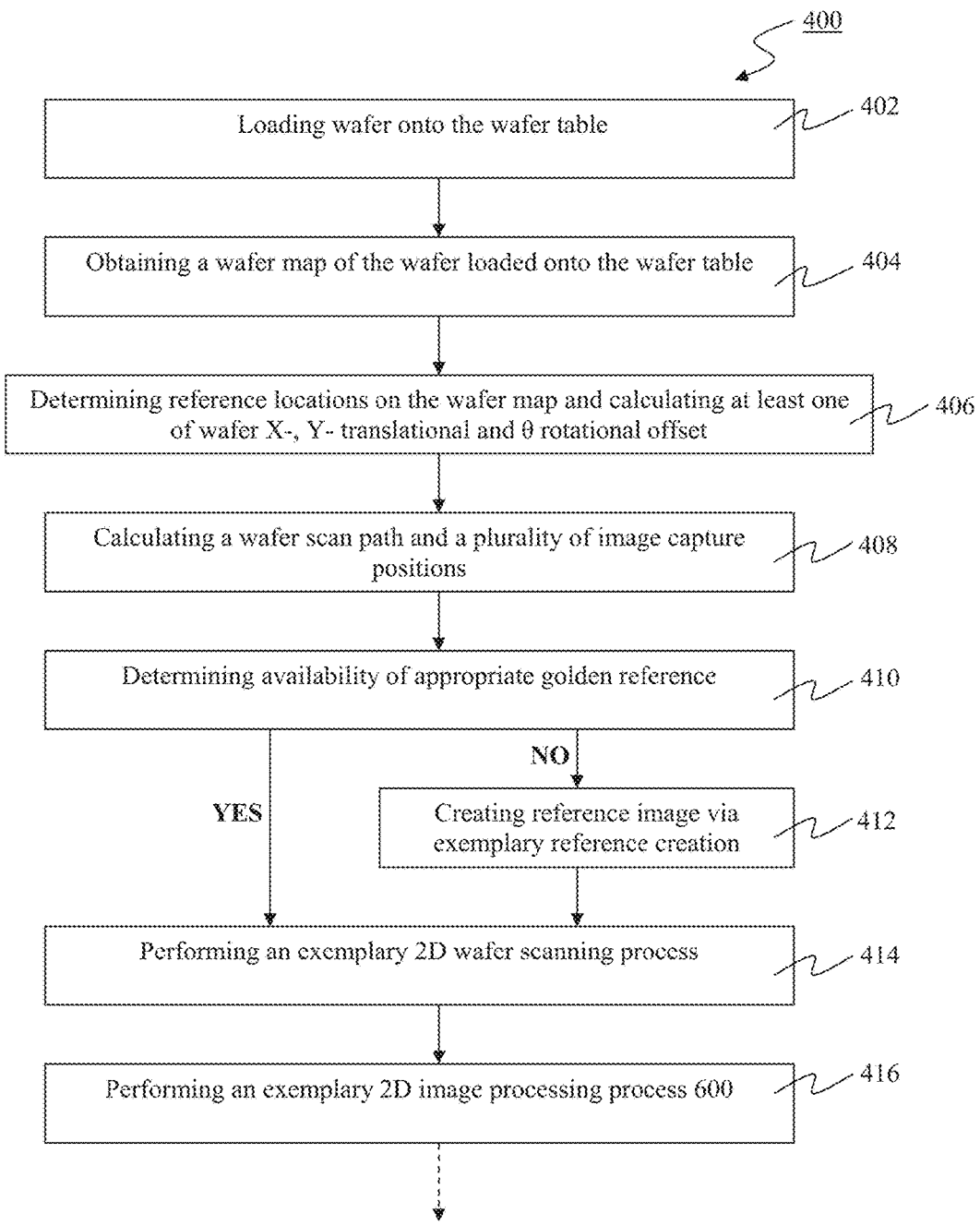
FIGS. 17A and 17B show a process flow diagram of process for inspecting wafers provided by an embodiment of the present disclosure.
Figure 17B:
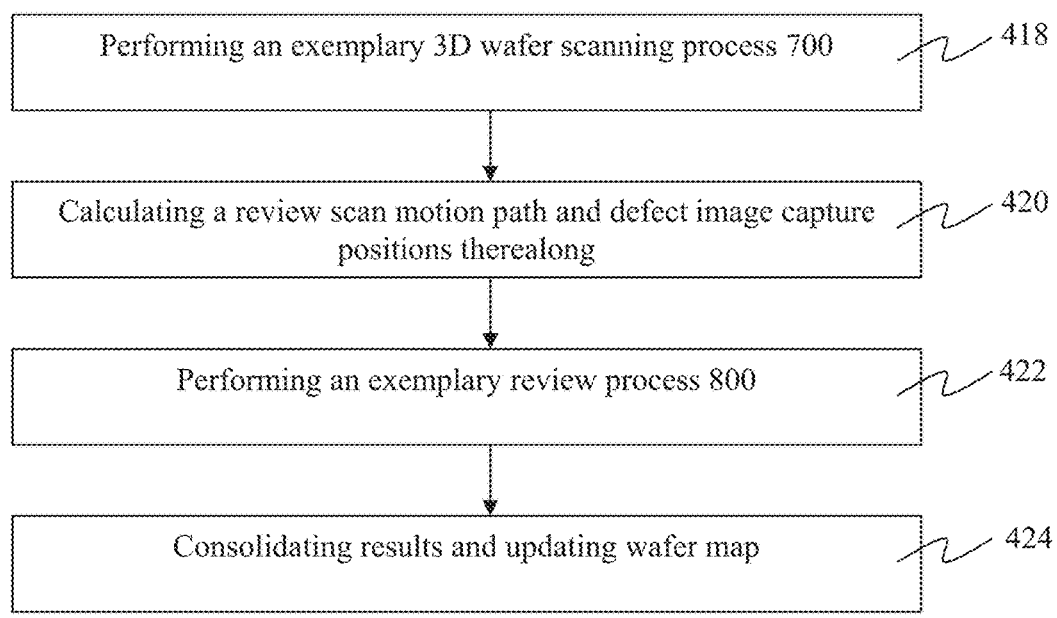

FIGS. 17A and 17B show a flowchart of an exemplary method or process 400 for inspecting a wafer 12 according to an embodiment of the present disclosure. In many embodiments, the process 400 for inspecting the wafer 12 enables at least one of detection, classification and review of defects on the wafer 12.

In most embodiments of the present disclosure, the process 400 for inspecting wafers 12 utilizes reference images (also known as golden references) to which captured images of the wafers 12 are compared for at least one of detecting, classifying and review of defects on the wafers 12. For purposes of clarity, description of an exemplary reference image creation process 900 is provided before the description of the exemplary process 400.

Exemplary Reference Image Creation Process 900

Figure 18A:
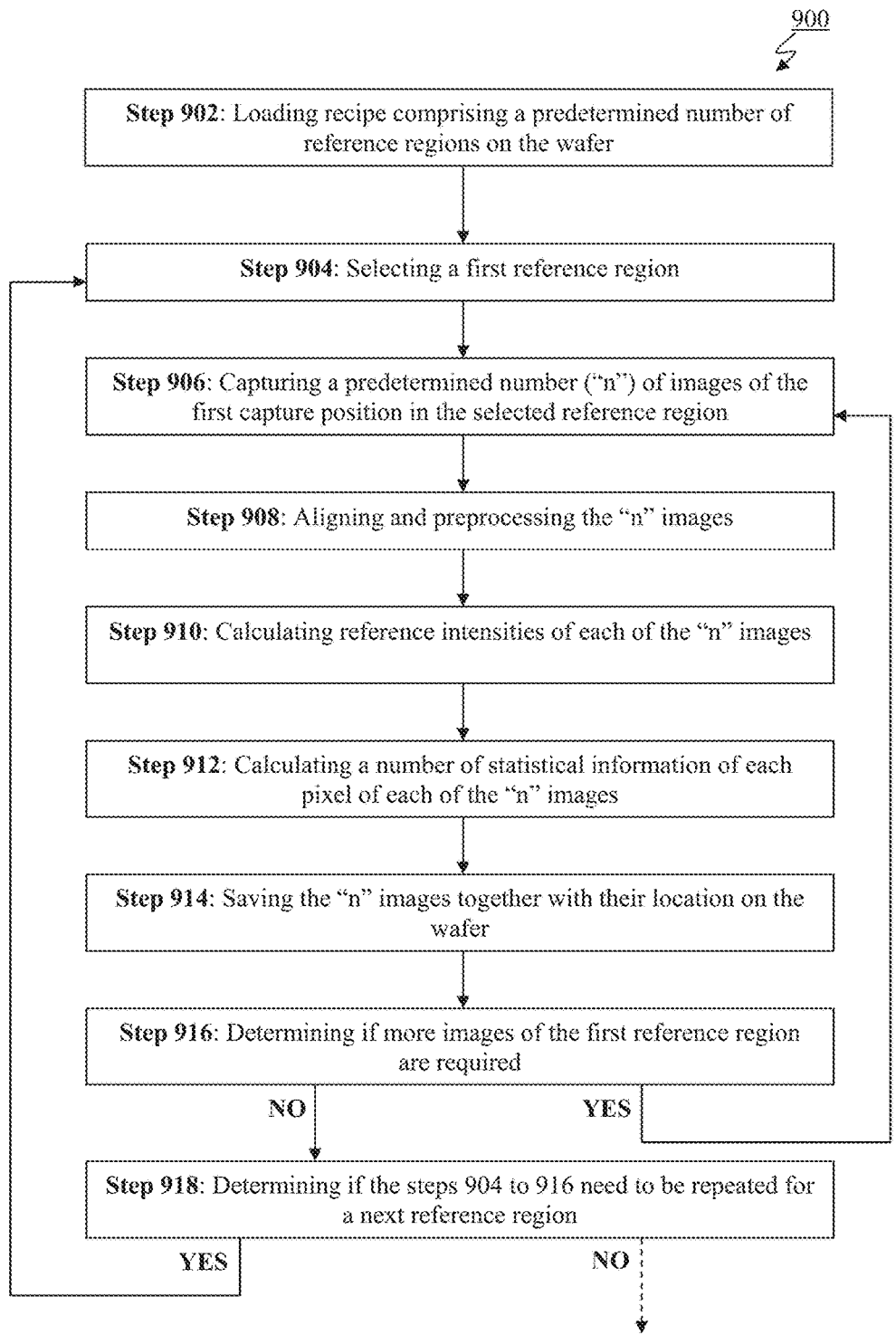
FIGS. 18A and 18B show a process flowchart of a reference image creation process for creating reference images used for comparing with images captured during performance of the process of FIGS. 17A and 17B in accordance with an embodiment of the present disclosure.
Figure 18B:
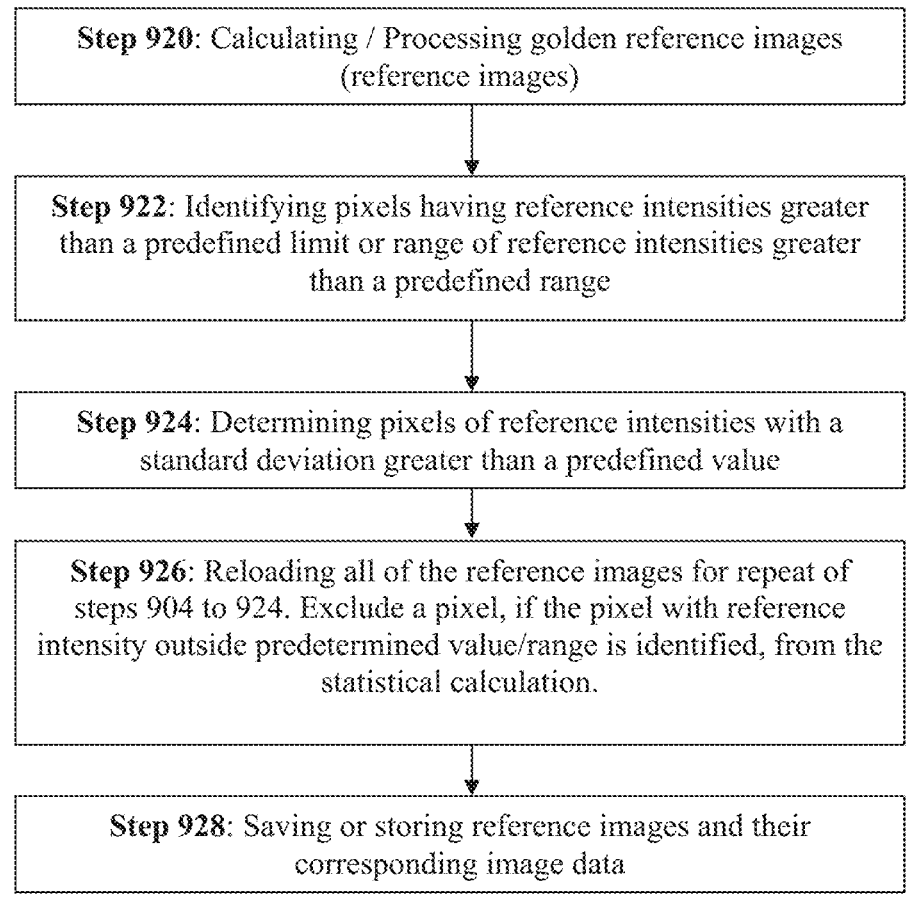

FIGS. 18A and 18B show a flowchart of the reference image creation process 900 provided by particular embodiments of the present disclosure.

In a step 902 of the reference image creation process 900, a recipe comprising a predetermined number of reference regions on the wafer 12 is loaded. In several embodiments of the present disclosure, the recipe is created or derived by a computer software program. Alternatively, the recipe is manually created. The recipe can be stored in the database of the CPU. Alternatively, the recipe can be stored in an external database or memory space.

Each of the predetermined reference regions represents locations on the wafer 12, which is of an unknown quality. The use of multiple reference regions helps to compensate for possibility of surface variations at different locations on the wafer 12, or between multiple wafers. Such surface variations include, but are not limited to, differential planarity and illumination reflectivity. It will be understood by a person skilled in the art that the predetermined number of reference regions may represent an entire surface area of the wafer 12. Alternatively, the predetermined number of reference regions may represent multiple predetermined locations on multiple wafers.

In a step 904, a first reference region is selected. In a subsequent step 906, a predetermined number ("n") of images are captured of the first capture position of the selected reference region. More specifically, the n images are captured at each predetermined locations of the selected reference region. Number and location of the predetermined locations of the selected reference region can be varied as required and facilitated by at least one of software program and manual input.

The n images can be captured using at least one of the first image capture device 32, the second image capture device 34 and the review image capture device 62 as required. Alternatively, the n images are captured using a different image capture device. Illuminations used for capture of the n images can be varied as required, and are for example one or combination of the brightfield illumination, the DHA illumination and the DLA illumination. Colors and intensities of the illuminations used for capture of the n images can be selected, and varied, as required.

Capture of multiple images at each position enables reference images to be created taking into account the variations in the illumination, optical setup and the imaging means used during capture of the reference images. This method of reference image creation minimizes unwanted influences or effects on defect detection, and classification, due to variations between the illumination conditions. In addition, a number of images of the selected reference region may be captured for each specified illumination condition. In most embodiments of the present disclosure, capture of multiple images at each specified illumination condition facilitates a normalizing or compensation of illumination variation from flash to flash or from strobe to strobe.

In several embodiments of the present disclosure, the n images are preferably stored in the database of the CPU. In other embodiments of the present disclosure, the "n" images are stored in an external database or memory space as required. In a step 908, the n images captured in the step 906 are aligned and preprocessed. In several embodiments of the present disclosure, subpixels of the n images captured in the step 906 are registered. Registration of the subpixels of the n images can be performed using known references including, but not limited to, traces, bumps or pads formed on the one or more wafer 12 using one or more of binary, gray scale or geometrical pattern matching.

In a step 910, reference intensities of each of the n images are calculated. More specifically, reference intensity of each image captured at each of the predetermined locations of the selected reference region is calculated. The calculation of reference intensities of each of the n images helps to normalize or compensate for color variation at different locations or regions on the wafer 12 (or the multiple wafers). In addition, the calculation of reference intensities of each of the n images can help to account, or compensate, for other surface variations at different locations or regions on the wafer 12 (or the multiple wafers 12).

The step 910 results in calculation of n reference intensities, each of the n reference intensities corresponding to one of the n images. In a step 912, a number of statistical information of intensities of each pixel of each of the n images is calculated. The number of statistical information includes; but is not limited to, an average, a range, a standard deviation, a maximum and a minimum intensity for each pixel of each of the n images.

In most embodiments of the present disclosure, the average is a geometric mean of the reference intensity for each pixel of each of the "n" images. Geometric mean is a type of mean or average, which indicates the central tendency or typical value of a set of numbers, or n numbers. The numbers of the set are multiplied and then the nth root of the resulting product is obtained. A formula for obtaining geometric mean is shown below:

$$\left(\prod_{i=1}^{n} a_i\right)^{1/n} = \sqrt[n]{a_1 \cdot a_2 \ldots a_n}$$

Calculation of the geometric mean instead of arithmetic mean or median prevents the average intensity calculated for each pixel of each of the n images from being unduly affected by extreme values in a data set.

In addition, range of absolute intensity (hereinafter referred to as Ri) for each pixel of the n images is calculated. Preferably, the Ri for each pixel of the "n" images is the value between a maximum and a minimum absolute intensity for each pixel of the n images.

As previously mentioned, the standard deviation of the intensity of each pixel for each of the n images of the first reference region captured in the step 906 is also calculated. In most embodiments of the present disclosure, the standard deviation is a geometric standard deviation, which describes how spread out are a set of numbers whose preferred average is the geometric mean. A formula for obtaining the standard deviation is shown below:

$$\sigma_g = \exp\left(\sqrt{\frac{\sum_{i=1}^{n}(\ln A_i - \ln \mu_g)^2}{n}}\right). \quad (1)$$

where $\mu_g$, is the geomtric mean of a set of numbers $\{A_1, A_2, \ldots, A_n\}$.

In a step 914, the "n" images captured are temporarily saved, together with their corresponding information such as location on the wafer 12 or first reference region. In most embodiments of the present disclosure, the statistical information calculated in the step 912 is also temporarily saved in the step 914. In several embodiments of the present disclosure, the above data is saved in the database of the CPU. In other embodiments of the present disclosure, the above data is saved in an alternative database or memory space as required.

In a step 916, it is determined if more images of the selected reference region are required. In several embodiments of the present disclosure, the step 916 is software controlled and preformed automatically. In several embodiments of the present disclosure, the step 916 is performed with a reliance on information obtained by the steps 910 and 912. In other embodiments of the present disclosure, the step 916 is manually facilitated or controlled using techniques known in the art.

If it is determined in the step 916 that more images of the selected reference region are required, the steps 904 to 916 are repeated. The steps 904 to 916 can be repeated any number of times as required. When it is determined in the step 916 that no more images of the first reference region is required, a step 918 is performed to determine if the steps 904 to 916 need to be repeated for a next reference region (for purposes of the present description, a second reference region) of the predetermined number of reference regions. In several embodiments of the present disclosure, the step 918 is software controlled and performed automatically. In addition, the step 918 is preferably performed using information obtained in at least one of steps 910, 912 and 916. In other embodiments of the present disclosure, the step 918 is manually facilitated or controlled using techniques known in the art.

If it is determined in the step 918 that images of the second reference region need to be captured, i.e. if the steps 904 to 916 need to be repeated for the second reference region, a signal is generated for repeating the steps 904 to 916. The steps 904 to 918 can be repeated any number of times as required. In several embodiments of the present disclosure, the repetition of the steps 904 to 918 is software controlled and automated.

When it is determined in the step 918 that the steps 904 to 918 do not need to be repeated, i.e. that images of the next reference region of the predetermined number of reference regions are not required, golden reference images (hereinafter referred to as reference images) are then calculated in a step 920.

In most embodiments of the present disclosure, the calculation of the reference images is software controlled, and is performed via a series of program instructions. The following steps are exemplary steps performed for calculating the reference images. It will however be understood by a person skilled in the art that additional steps or techniques complementary to the following steps may be performed in the calculation of the reference image.

In a step 922, pixels having reference intensities greater than a predefined limit is determined. In addition, pixels having range of pixel intensities greater than a predefined range is determined in the step 922. The predefined limit and range of the step 922 can be either software selected and determined or manually selected and determined. In a step 924, pixels of intensities with a standard deviation greater than a predefined value are identified. The predefined value of the step 924 can be either software selected and determined or manually selected and determined. In a step 926, the previously saved images, as in the step 914, are reloaded for repeat of any one or more of the steps 904 to 924 if a pixel with reference intensities outside predetermined value or range is identified during the steps 922 to 924.

The steps 922 to 926 facilitate identification of images comprising pixels of specific pixel intensities. In several embodiments of the present disclosure, the steps 922 to 926 enable identification of images containing pixels having reference intensities outside predefined limits or ranges, for example identification of "undesirable" images, to be identified. More specifically, the steps 922 to 926 eliminate "undesirable" pixels from the reference image calculation and help to prevent the "undesirable" pixels influence on the final reference pixel values of the reference image.

The "undesirable" images are discarded. This facilitates elimination of defective data or images, thereby preventing influence or presence of such defective data with generated reference images. In a step 928, images comprising pixels within predefined limits and ranges (i.e. images not discarded) are consolidated.

In most embodiments of the present disclosure, the reference image creation process 900 results in derivation of the following image data:

Normalized average of intensity of each pixel of each of the consolidated images Standard deviation of intensity of each pixel of each of the consolidated images Maximum and minimum intensities of each pixel of each of the consolidated images Average reference intensity of each of the predetermined number of reference regions determined in the step 702

The consolidated images of the step 928 represent reference images. In several embodiments of the present disclosure, the reference images, together with corresponding image data are further saved in the step 928. In several embodiments of the present disclosure, the reference images and their corresponding image data are saved in the database of the CPU. In other embodiments of the present disclosure, the reference images and their corresponding image data are saved in an alternative database or memory space. It will be appreciated by a person skilled in the art that the step 922 to 926 helps to reduce amount or size of memory space required for storing the reference images and their corresponding data, which may enable the method 400 to be performed at a higher speed or accuracy.

In several embodiments of the present disclosure, the average intensity of each pixel is normalized to 255 in order to display and visualize the reference images. It will however be understood by a person skilled in the art that the average intensity of each pixel can be normalized to an alternative value in order to display and visualize the reference images.

The steps 904 to 928 can be repeated a predetermined number of times for capturing a corresponding number of images with at least one of the first image capture device 32, the second image capture device 34 and the review camera 62. In addition, the steps 904 to 928 can be repeated for capturing images at different illuminations or illumination conditions, for example brightfield illumination, DHA illumination, DLA illumination and thin line illumination, as required. The repetition of the steps 904 to 928 enables creation of reference images for multiple illuminations or illumination conditions, and with multiple image capture devices as required.

As previously described, the derivation of reference images for multiple reference regions of the wafer 12 (or multiple wafer) and at multiple illumination conditions helps to ensure accountability, and compensation where required, for variations in quality of subsequently captured images due to variations in the lighting conditions. For example, the capture of reference images at different reference regions of the wafer 12 (i.e. different locations on the wafer 12) preferably ensures accountability and compensation for color variations at different locations on the wafer 12.

In several embodiments of the present disclosure, the steps 904 to 928 are preferably executed and controlled by the CPU. More specifically, the steps 904 to 928 are at least one of executed and controlled by a software program. In several embodiments of the present disclosure, at least one of the steps 904 to 928 may be manually assisted if required. The reference images created by the exemplary reference image creation process 900 are used for comparison with subsequently captured images of wafers 12 of unknown quality to thereby enable at least one of detection, classification and review of defects on the wafer 12.

As previously mentioned, various embodiments of the present disclosure provide the process or method 400 for inspection of wafers 12 to thereby at least one of detect, classify and review defects present on the wafers 12.

In a first process portion 402 of the process 400, the wafer 12 to be inspected by the system 10 is loaded onto the wafer table 16. In several embodiments of the present disclosure, the wafer 12 is extracted from the wafer stack 20 by the robotic wafer handler 18 and transferred onto the wafer table 16. Suction or vacuum is applied to the wafer table 16 to secure the wafer 12 thereonto.

In several embodiments of the present disclosure, the wafer 12 includes a wafer identification number (ID number) or barcode. The wafer ID number or barcode is engraved or tagged onto a surface of the wafer 12, more specifically at a periphery of the surface of the wafer 12. The wafer ID number or barcode helps to identify the wafer 12 and ensures that the wafer 12 is correctly or appropriately loaded onto the wafer table 16.

In a second process portion 404, a wafer map of the wafer 12 loaded onto the wafer table 16 is obtained. The wafer map may be loaded from the database of the programmable controller. Alternatively, the wafer map may be retrieved from an external database or processor. Further alternatively, the wafer map may be prepared or derived upon the loading of the wafer 12 onto the movable support platform using methods or techniques known to a person skilled in the art.

In a third process portion 406, one or more reference locations are captured or determined on the wafer map and at least one of wafer X, Y translational and θ rotational offset is calculated using techniques known to a person skilled in the art.

In a subsequent process portion 408, a wafer scan motion path and a plurality of image capture positions are calculated or determined. The wafer map obtained in the step 404 preferably facilitates the calculation of the wafer scan motion path and the plurality of image capture positions. In most embodiments of the present disclosure, the calculation of the wafer scan motion path is dependent on at least one of several known parameters. Such known parameters include, but are not limited to, rotation offset, wafer size, wafer die size, wafer pitch, inspection area, wafer scan velocity and encoder position. Each of the plurality of image capture positions reflects or corresponds to a position on the wafer 12 of which images are to be captured. In most embodiments of the present disclosure, each of the plurality of image capture positions can be altered as required using techniques known to a person skilled in the art. The number of image capture positions can also be altered as required using techniques known to a person skilled in the art.

In several embodiments of the present disclosure, the process portions 404 to 408 are performed automatically by the system 10, more specifically by the programmable controller of the system 10. In some embodiments of the present disclosure, any one of the process portions 404 to 408 may be performed by, or with the aid of, an alternative processor.

In a fifth process portion 410, the programmable controller of the system 10 determines availability of an appropriate golden reference (hereinafter referred to as a reference image). If the reference image is not available, the reference image is created by the exemplary reference image creation process 900 as described above in a sixth process portion 412.

In most embodiments of the present disclosure, the reference image is obtained, or created, before performing an exemplary two-dimensional (2D) wafer scanning process 400 in a seventh process portion 414. A process flow diagram of the exemplary two-dimensional (2D) wafer scanning process 500 according to various embodiments of the present disclosure is shown in FIG. 19.

i. Exemplary Two-dimensional (2D) Wafer Scanning Process 500

Figure 19:
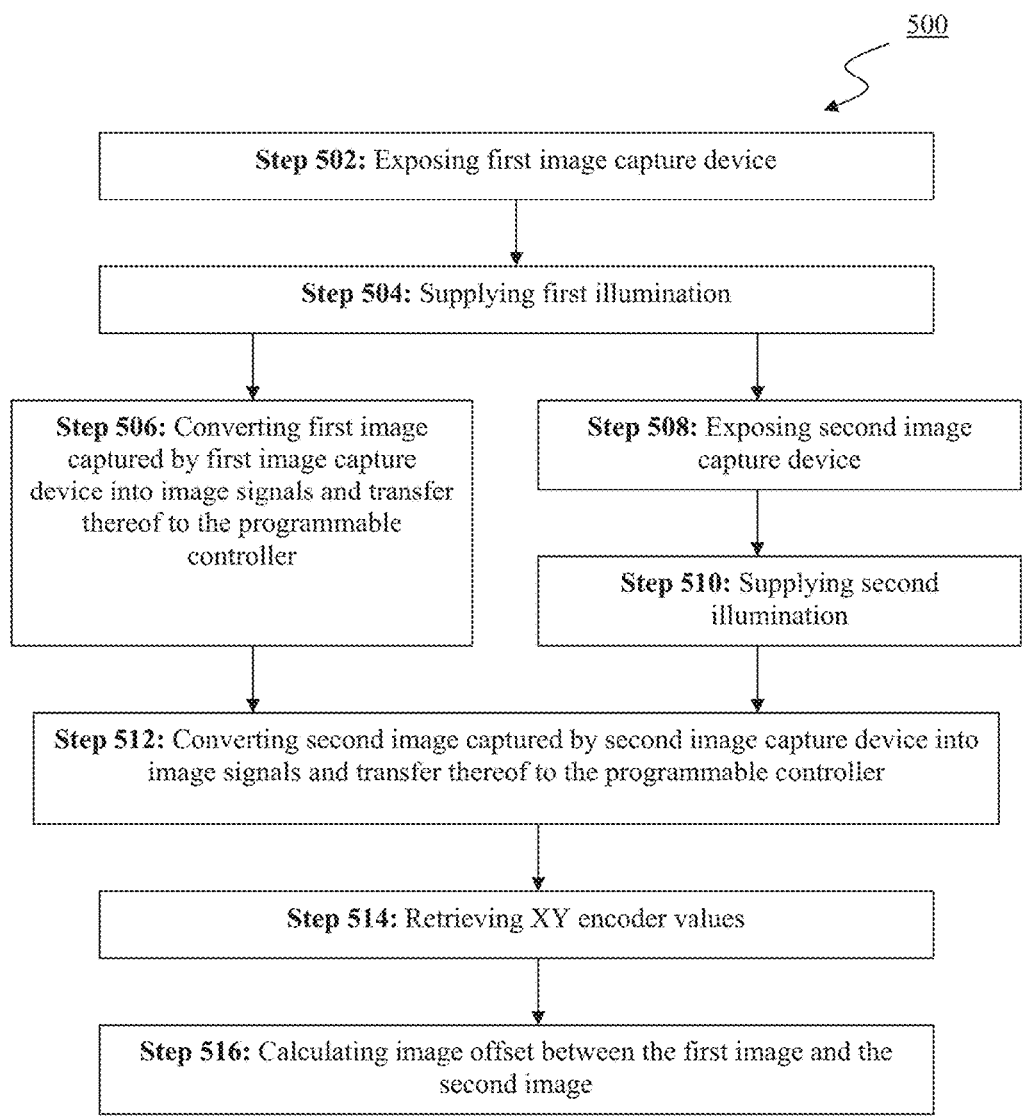
FIG. 19 is a process flow diagram of an exemplary two-dimensioned wafer scanning process with timing offset performed during the process of FIGS. 17A and 17B in accordance with an embodiment of the present disclosure.

FIG. 19 shows a process flow diagram of the exemplary two-dimensional (2D) wafer scanning process 500 according to various embodiments of the present disclosure. The 2D wafer scanning process 500 enables capture of brightfield images and darkfield images by the first image capture device 32 and the second image capture device 34.

In a first process portion 502 of 2D wafer scanning process 500, the first image capture device 32 is exposed. In a second process portion 504, a first illumination is supplied. The first illumination is for example brightfield illumination supplied by the brightfield illuminator 26, DHA illumination supplied by the high angle darkfield illuminator 30 or DLA illumination supplied by the low angle darkfield illuminator 28. In several embodiments of the present disclosure, selection of the first illumination to be supplied in the step 504 is determined by an illumination configurator (not shown). In several embodiments of the present disclosure, the illumination configurator is a component of the system 10 and electronically coupled to the illuminators (28, 30, 52, 64 and 66) of the system 10. In several embodiments of the present disclosure, the illumination configurator is a component of the CPU.

The image capture devices 32 and 34 can use any combination of illuminations provided by brightfield illuminator 26, DHA illuminator 30 and DLA illuminator 28. Examples of the possible combinations for the first illumination used by the image capture device 32 and the second illumination used by the image capture device 34 are shown in the table of FIG. 19. In most embodiments of the present disclosure, if the first image capture device 32 and the second image capture device 34 both use a substantially similar illumination, then the throughput of such a configuration would be the highest of all the possible configurations.

For purposes of the following description, configuration 1 as shown in the table of FIG. 20 is selected by the illumination configurator. Accordingly, the first illumination is the brightfield illumination supplied by the brightfield illuminator 26.

In most embodiments of the present disclosure, the process portions 502 and 504 are performed simultaneously. Performance of the process portions 502 and 504 enables capture of a first image, as shown in FIG. 22a, by the first image capture device 32. In a third process portion 506, the first image captured by the first image capture device 32 is converted into image signals and transmitted to the CPU via the data transfer process and stored in the database or storage memory.

In a fourth process portion 508, the second image capture device 34 is exposed. In a fifth process portion 510, a second illumination is supplied. As with the first illumination, selection of the second illumination is determined by the illumination configurator in most embodiments of the present disclosure. For purposes of the present description, configuration 1 as shown in the table of FIG. 20 is selected by the illumination configurator. Accordingly, the second illumination is the DHA illumination supplied by the high angle darkfield illuminator 30. It will however be appreciated by a person skilled in the art that the first illumination and the second illumination may be alternative illuminations as required, for example those of the different configurations shown in the table of FIG. 20.

In most embodiments of the present disclosure, the process portions 508 and 510 are performed simultaneously. In several embodiments of the present disclosure, the process portion 506 occurs in tandem with the performance of the process portions 508 and 510. In many embodiments, performance of the process portions 508 and 510 facilitate or enable capture of a second image, as shown in FIG. 22b, by the second image capture device 34.

In a sixth process portion 512, the second image captured by the second image capture device 34 is converted into image signals and transmitted to the programmable controller via the data transfer process and preferably stored in the database or storage memory.

Figure 21:
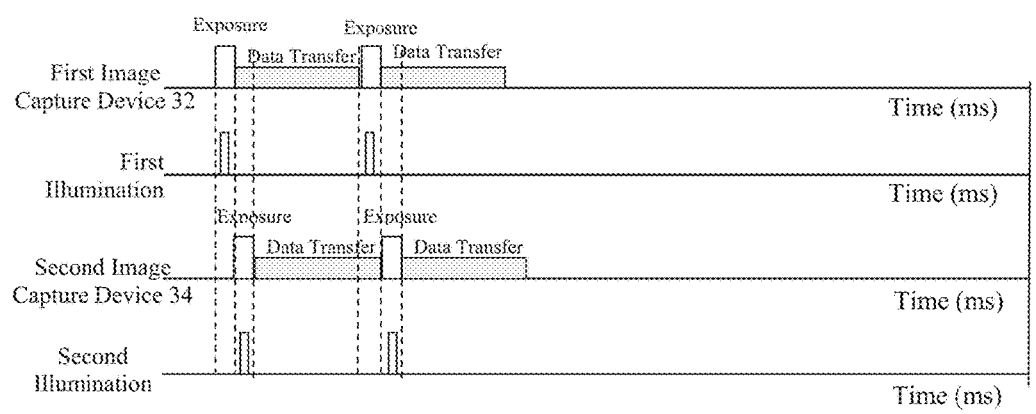
FIG. 21 shows a timing chart for capturing of a first image by the first image capture device and capturing of a second image by the second image capture device.

FIG. 21 shows a diagram of an exposure of the first image capture device 32, supply of the first illumination, exposure of the second image capture device 34, supply of the second illumination, and data transfer processes in accordance with several embodiments of the present disclosure.

In many embodiments, the process portions 502 to 512 can be repeated any number of times for capturing a corresponding number of sets of first images and second images of the wafer 12. In several embodiments of the present disclosure, the process portions 502 to 512 are preferably repeated for capturing images with the first illumination and the second illumination of the wafer 12 at each of the plurality of image capture positions along the wafer scan motion path as calculated in the process portion 408.

As previously described, each of the first image (or first response) and the second image (or second response) can be converted into image signals and transmitted to the programmable controller and subsequently stored in the database or storage memory.

In several embodiments of the present disclosure, each of the process portions 502 to 512 is performed while the wafer 12 is in motion. This is to say, the capture of the first image and the second image is performed while the wafer 12 is in motion along the wafer scan motion path. Accordingly, a person skilled in the art will appreciate that the wafer 12 will be displaced by a predetermined distance along the wafer scan motion path between the process portions 502, 504 (which in several embodiments occur simultaneously) and the process portions 508, 510 (which in several embodiments also occur simultaneously). The predetermined distance depends on several factors including, but not limited to, speed of displacement of the wafer 12 along the wafer scan motion path and time required for any one of the process portions 502 to 512. The predetermined distance may be controlled and varied as required, for example by the CPU. The control and variation of the predetermined distance may be at least one of software or manually facilitated.

In many embodiments, the displacement of the wafer 12 as described above results in creation of a predetermined image offset when the first image is superimposed onto, or compared with, the second image.

FIG. 22c shows a combined image of the first image and the second image demonstrating resulting image offset due to the capture of the first image and the second image while the wafer 12 is in motion. The predetermined image offset depends on several factors including, but not limited to, speed of displacement of the wafer 12 along the wafer scan motion path and time required for any one of the process portions 502 to 512. Control and variation of the predetermined image offset may be at least one of software or manually facilitated.

In a process portion 514, XY encoder values are retrieved. In most embodiments of the present disclosure, the XY encoder values are obtained during each of the process portions 504 and 510. In most embodiments of the present disclosure, the XY encoder values represent positions (XY-displacement) of the wafer 12 along the wafer scan motion path. The XY encoder values obtained are used for calculating the image offset (coarse offset) between the first image and the second image (i.e. relative offset of the second image from the first image) in a process portion 516. The fine image offset is calculated by performing sub pixel image alignment using pattern matching techniques. The final offset is obtained by applying a predetermined mathematical formula on the coarse and fine image offsets. The predetermined mathematical formula may be adjusted as required using techniques known to a person skilled in the art.

The 2D wafer scanning process 500 performed in the process portion 414 of the process 400 results in the capture of multiple images of the wafer 12, in most embodiments of the present disclosure, at the calculated image capture positions along the wafer scan motion path.

In an eighth process portion 416 of the process 400, an exemplary two-dimensional (2D) image processing process 600 is performed for at least one of identifying or detecting, classifying, consolidating and storing defects on the wafer 12.

i. Exemplary 2D Image Processing Process 600

Figure 23:
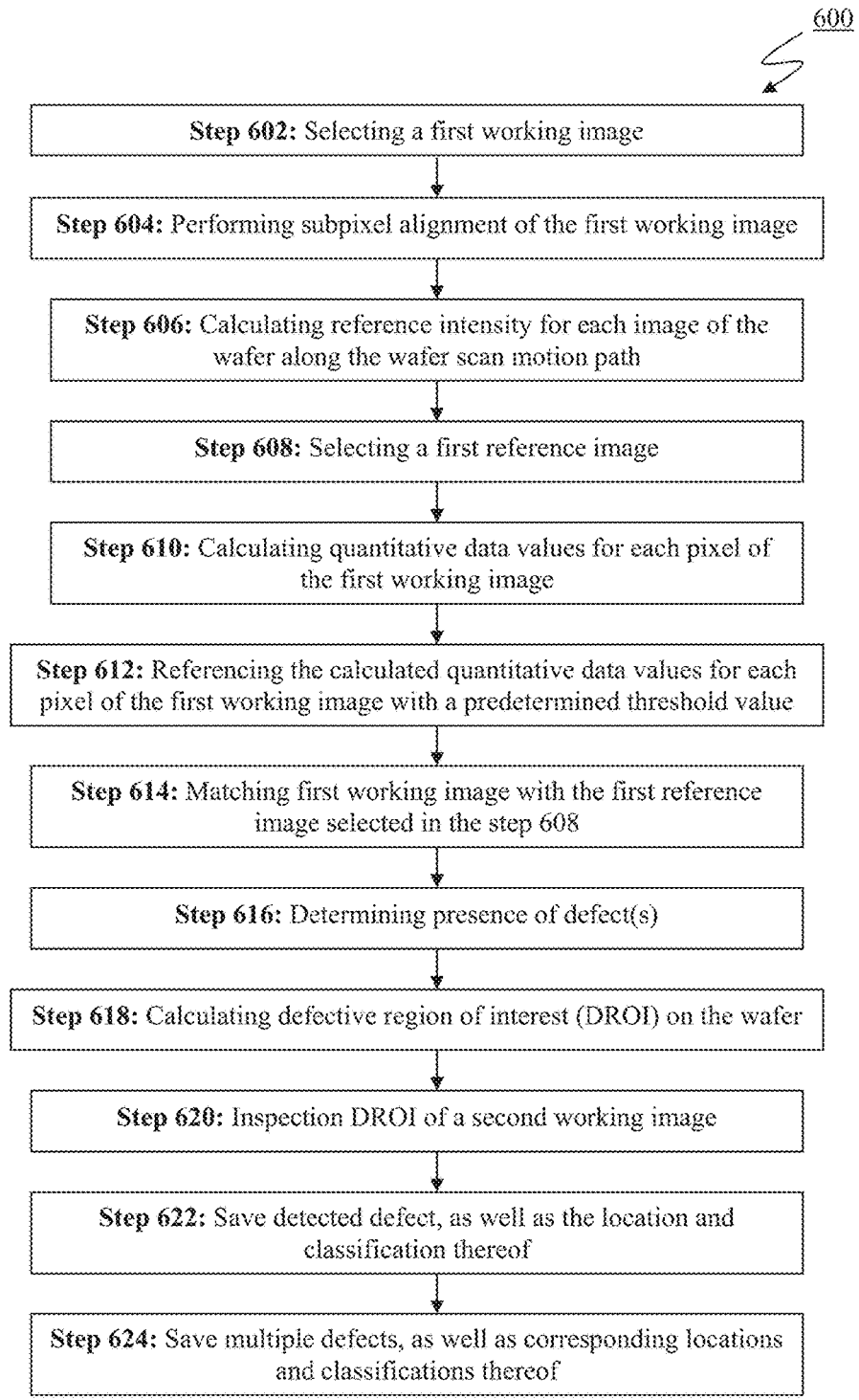
FIG. 23 is a process flow diagram of a two-dimensional image processing process performed in the process of FIGS. 17A and 17B in accordance with an embodiment of the present disclosure.

FIG. 23 shows a process flow diagram of the exemplary 2D image processing process 600 according to an embodiment of the present disclosure.

In many embodiments, the 2D image processing process 600 according to an embodiment of the present disclosure facilitates processing of the images captured in the 2D wafer scanning process 500. In addition, the 2D image processing process 600 facilitates at least one of identifying or detecting, classifying, consolidating and storing defects on the wafer 12.

In a first process portion 602 of 2D image processing process 600, a first working image is selected and loaded in a memory workspace. The first working image is selected from the number of first images and second images captured and saved during the 2D wafer scanning process. For purposes of the present description, the first working image represents the first image captured by the first image capture device 32 during the 2D wafer scanning process 500.

In a second process portion 604, sub-pixel alignment of the first working image is performed. In several embodiments of the present disclosure, sub-pixel alignment is performed using pattern-matching techniques using one or more templates. Such sub-pixel alignment is performed using one of binary or gray scale or geometrical pattern matching methods. Once aligned, reference intensity for each image is calculated from one or more predefined region of interests in the image as shown in a third process portion 606. The process portions 604 and 606 may be collectively referred to as a preprocessing of the first working image. It can be readily appreciated that the preprocessing is not limited to above process portions. Additional process portions or steps can be incorporated for the preprocessing if necessary.

In a subsequent process portion 608, a first golden reference or reference image is selected. The first reference image selected in the process portion 608 corresponds or matches with the first working image. In most embodiments of the present disclosure, the first reference image is selected from a database or collection of golden references or reference images created by the exemplary reference creation process 900 in the process portion 412 of the process 400. The exemplary reference creation process 900 is described in detail above, and is shown in FIGS. 18A and 18B.

In a fifth process portion 610, quantitative data values for each pixel of the first working image are calculated. In a subsequent process portion 612, the calculated quantitative data values for each pixel of the first working image are referenced with a predetermined threshold value together with multiplicative or additive factors.

In a seventh process portion 614, the first working image is then matched or evaluated against the first reference image selected in the process fourth portion 608. The matching or evaluation of the first working image with the first reference image facilitates detection or identification of defects on the wafer 12. In several embodiments of the present disclosure, the CPU is programmed for effecting automated matching between the first working image and the first reference image. The programmable controller carries out a series of computing instructions or algorithms for matching the first working image with the first reference image to thereby enable the detection or identification of defects on the wafer 12.

Determination of presence of one or more defects occurs in an eighth process portion 616 of the 2D image processing process 600. If more than one defects are detected or identified in the process portion 616, the algorithm would sort the defects from the largest to the shortest based on either one or all of area, length, width, contrast, compactness, fill factor, edge strength among others. Further the algorithm selects only those defects which meets user defined criteria to calculate defective region of interest (DROI). If a defect (or more than one defects) is detected or identified in the process portion 616, DROI on the wafer 12 is then calculated in a ninth process portion 618.

In several embodiments of the present disclosure, the DROI is calculated dynamically by the CPU in the process portion 618. In several embodiments of the present disclosure, the CPU is programmed (i.e. includes or embodies a series of computing instructions or software) for enabling the calculation of the DROI.

In a tenth process portion 620, a corresponding DROI of a second working image is inspected. More specifically, the second working image is the second image captured by the second image capture device 34 during the 2D wafer scanning process 400. The DROI of the second image (which is a corresponding image of the first image), is inspected in the process portion 620 after performing sub-pixel alignment of second working image. In several embodiments of the present disclosure, the inspection of the DROI of the second working image facilitates confirmation of defect detected in the process portion 616. In several embodiments of the present disclosure, the process portion 620 facilitates classification of defect detected in the process portion 606.

The system 10 processes the DROIs of the second working image instead of the entire image. In addition, in the process portion 616, if no defect is found, the process or method 600 would skip the process portions 618 and onwards. This will further reduce the amount of resources or processing bandwidth needed for processing the second working image. It can be readily appreciated that such intelligent processing sequence is dynamically decided based on the results of preceding steps. This will facilitate improved system 10 throughput or wafers inspected per hour.

In a process portion 622, the detected defect, more specifically the location or position of defect as well as the classification thereof, is saved. In several embodiments of the present disclosure, the detected defect, and the location and classification thereof, is saved in the database of the CPU. In other embodiments of the present disclosure, the detected defect, and the location and classification thereof, is saved in an alternative database or memory space.

The process portions 602 to 622 can be repeated or looped any number of times for processing the images captured during the 2D wafer scanning process 500. In several embodiments of the present disclosure, each of the images captured during the 2D wafer scanning process 500 is sequentially loaded in the memory workspace and processed for facilitating the detection of defects, which may be present on the wafer 12. The process portions 602 to 622, and the repetition thereof, facilitates at least one of detection, confirmation, and classification of defects, which may be present on the wafer 12 at any of the multiple image capture positions along the wafer scan motion path.

In a process portion 624, each of multiple defects, and the locations and classifications thereof, detected by the 2D image processing process 600 are consolidated and saved, in several embodiments of the present disclosure, in the database of the CPU. In other embodiments of the present disclosure, the defects, and the locations and classifications thereof, are consolidated and saved in an alternative database or memory space.

In most embodiments of the present disclosure, the 2D image processing process is an automated process. In several embodiments of the present disclosure, the CPU is programmed for, or includes a series of computing instructions or software program, for automatically performing the 2D image processing process. In some embodiments of the present disclosure, the 2D image processing process may be facilitated by an at least one manual input where required.

Completion of the 2D image processing process 600 of the step 416 of the method 400 results in consolidation and storage of defects, and the locations and classifications thereof, detected using the brightfield illumination, the DHA illumination and DLA illumination.

In a subsequent process portion 418 of the process 400, an exemplary three-dimensional (3D) wafer scanning process, for example a first 3D wafer scanning process 700, a second wafer scanning process 750, or a third wafer scanning process 950, is performed in accordance with particular embodiments of the present disclosure.

In several embodiments of the present disclosure, the 3D wafer scanning process 700, 750, 950 enables capture of 3D profile images (or 3D images) of the wafer 12, for facilitating consequent formation of a 3D profile of the wafer 12 (or for obtaining information on the 3D characteristics or topology of the wafer 12). The wafer 12 is displaced along the calculated wafer scan motion path for capturing 3D images of the wafer 12 at any one or more of the multiple image capture positions, for instance, along the wafer scan motion path as calculated in the process portion 408.

In many embodiments of the present disclosure, selection and use of either the first 3D wafer scanning process 700, the second 3D wafer scanning process 750, or the third 3D wafer scanning process 950, in the process portion 418 of the process 400 can be dependent upon a number of factors, for example the presence and/or number of sets of optical elements or devices that can direct illumination (e.g., mirrors 54 and/or reflectors 84) of the system 10, inspection requirement(s), and/or wafer characteristics, properties and/or topographical features.

i. First 3D Wafer Scanning Process 700

Figure 24:
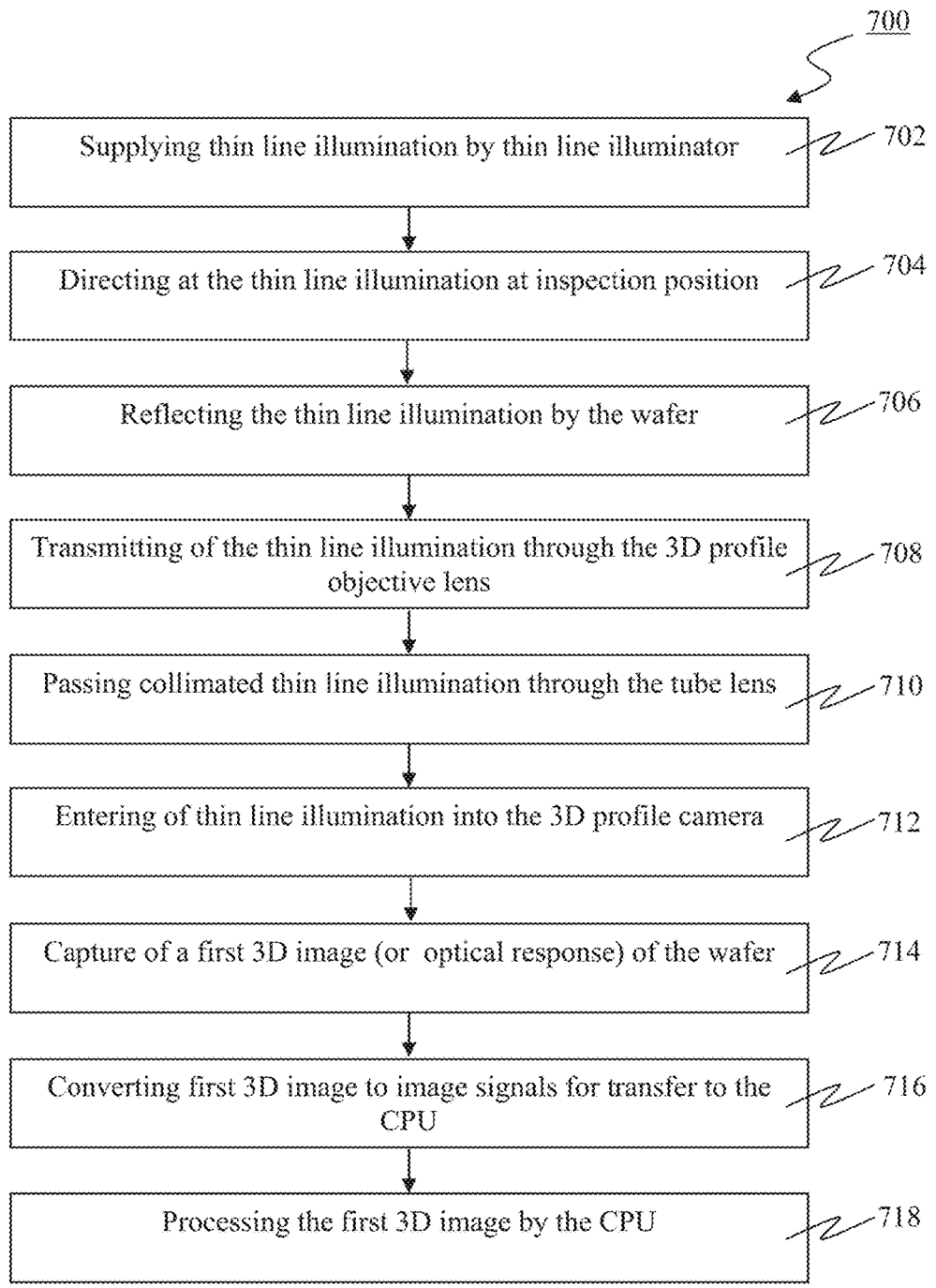
FIG. 24 is a process flow diagram of a first exemplary three-dimensional wafer scanning process performed in the process of FIGS. 17A and 17B in accordance with an embodiment of the present disclosure.

FIG. 24 shows a process flow diagram of the first 3D wafer scanning process 700 according to various embodiments of the present disclosure.

In a first process portion 702 of the first 3D wafer scanning process 700, thin line illumination is supplied by or emitted from the thin line illuminator 52. Thin line illumination can be supplied by one or more thin line illuminators 52. In particular embodiments, for example with the system 10 shown in FIG. 27a, thin line illumination is supplied or emitted by one thin line illuminator 52.

In a second process portion 704, the thin line illumination is directed at the inspection position by the set(s) of mirrors 54. As above described, the set of mirrors 54 can be configured and disposed for directing thin line illumination supplied by one thin line illuminator 52 to or towards the inspection position. In particular embodiments, the set of mirrors 54 can be configured and disposed for controlling, for example, establishing, selecting, and/or varying, an angle at which thin line illumination is directed towards the inspection position. In a representative implementation (e.g., corresponding to FIG. 27a), the thin line illumination can be directed to the surface of the wafer 12 by a set of mirrors 54 such that the thin line illumination is perpendicularly or otherwise incident upon the wafer's surface in accordance with an intended angle of incidence.

The number of sets of mirrors 54 can be dependent upon the number of thin line illuminators 52 used to supply thin line illumination, a manner in which thin line illumination is directed to or toward the inspection position, and/or an intended angle of incidence of the thin line illumination upon the wafer's surface.

In a subsequent process portion 706, the thin line illumination is reflected by a wafer 12, or a portion of the wafer 12, that is positioned at the inspection position. More specifically, the thin line illumination is reflected by a surface of the wafer 12, or portion of the wafer 12, positioned at the inspection position. Thin line illumination reflected off the wafer 12 can be directed towards the 3D profile objective lens 58 using a number of reflectors 84.

In a fourth process portion 708 of the first 3D wafer scanning process, thin line illumination reflected off the wafer 12 is transmitted through the 3D profile objective lens 58, which has aberration corrected in infinity. Accordingly, the transmission of the thin line illumination through the 3D profile objective lens 58 in the process portion 708 collimates the thin line illumination.

In a fifth process portion 710, the collimated thin line illumination then passes through the tube lens 60 before entering the 3D profile camera 56 in a sixth process portion 712. The tube lens 60 focuses the collimated thin line illumination onto the image capture plane of the 3D profile camera 56. Thin line illumination focused on the 3D image capture plane enables capture of a first 3D profile image of the wafer 12 (also known as a first response) in a step 714.

For purposes of the present disclosure, a 3D profile image or a 3D image can refer to an image that includes, provides, or conveys information or signals that correspond to three dimensional (3D) characteristics of a surface or structure (e.g., the topography of a surface or structure). In addition, a 3D profile image can also be referred to as a response, or optical response, captured by the 3D profile camera 56.

In several embodiments, the collimation of the thin line illumination between the 3D profile objective lens 58 and the tube lens 60 facilitates ease of introduction of optical components or accessories therebetween, and enables flexible positioning and reconfiguration of the 3D profile camera 56.

In several embodiments of the present disclosure, the thin line illumination is supplied by a laser or broadband fiber optic illumination source. In addition, the thin line illumination is preferably directed at the inspection position at a specified angle, for instance, with reference to a normal axis defined relative to a horizontal plane of the wafer 12 positioned thereat, and/or a horizontal plane of the wafer table 16. In several embodiments of the present disclosure, the angle at which the thin line illumination is directed to or toward the inspection position can be varied as required using techniques known to a person skilled in the art.

It will also be appreciated by a person skilled in the art that the wavelength of the thin line illumination may be selected and varied, for instance depending upon wafer inspection requirements. For instance, in several embodiments of the present disclosure, the wavelength of the thin line illumination is selected for enhancing accuracy of at least one of defect detection, verification, and classification.

The first 3D image is converted to image signals and transmitted to the CPU in a process portion 716. In a subsequent process portion 718, the first 3D image, or image signals thereof, is processed by the CPU for at least one of 3D height measuring, co-planarity measuring, and detecting and/or classifying a defect on a wafer 12.

In several embodiments of the present disclosure, the process portions 702 to 718 can be repeated any number of times for capturing a corresponding number of 3D images, and for transmitting the captured 3D images to the CPU. The process portions 702 to 718 can be performed either at selected image capture positions along the wafer scan motion path or the whole wafer.

In several embodiments of the present disclosure, the first 3D wafer scanning process 700 enhances accuracy with which the exemplary method 300 inspects a semiconductor wafer. In numerous embodiments of the present disclosure, the first 3D wafer scanning process 700 enhances accuracy of defect detection by the method 300. The use of the 3D wafer scanning process 700 can facilitate or enable determination of 3D metrological details such as co-planarity and height of three-dimensional structures, for example solder balls, gold bumps, and warpage, of individual die as well as whole wafers 12.

In several embodiments of the present disclosure, results of the process portions 702 to 718, and repetitions thereof, (e.g., results obtained from processing of 3D images) are saved in the database of the CPU. In other embodiments of the present disclosure, results of the process portions 702 to 718, and repetitions thereof, (e.g., results obtained from processing of 3D images) are saved in an alternative database or memory space as required.

(1) Second 3D Wafer Scanning Process 750

Figure 25:
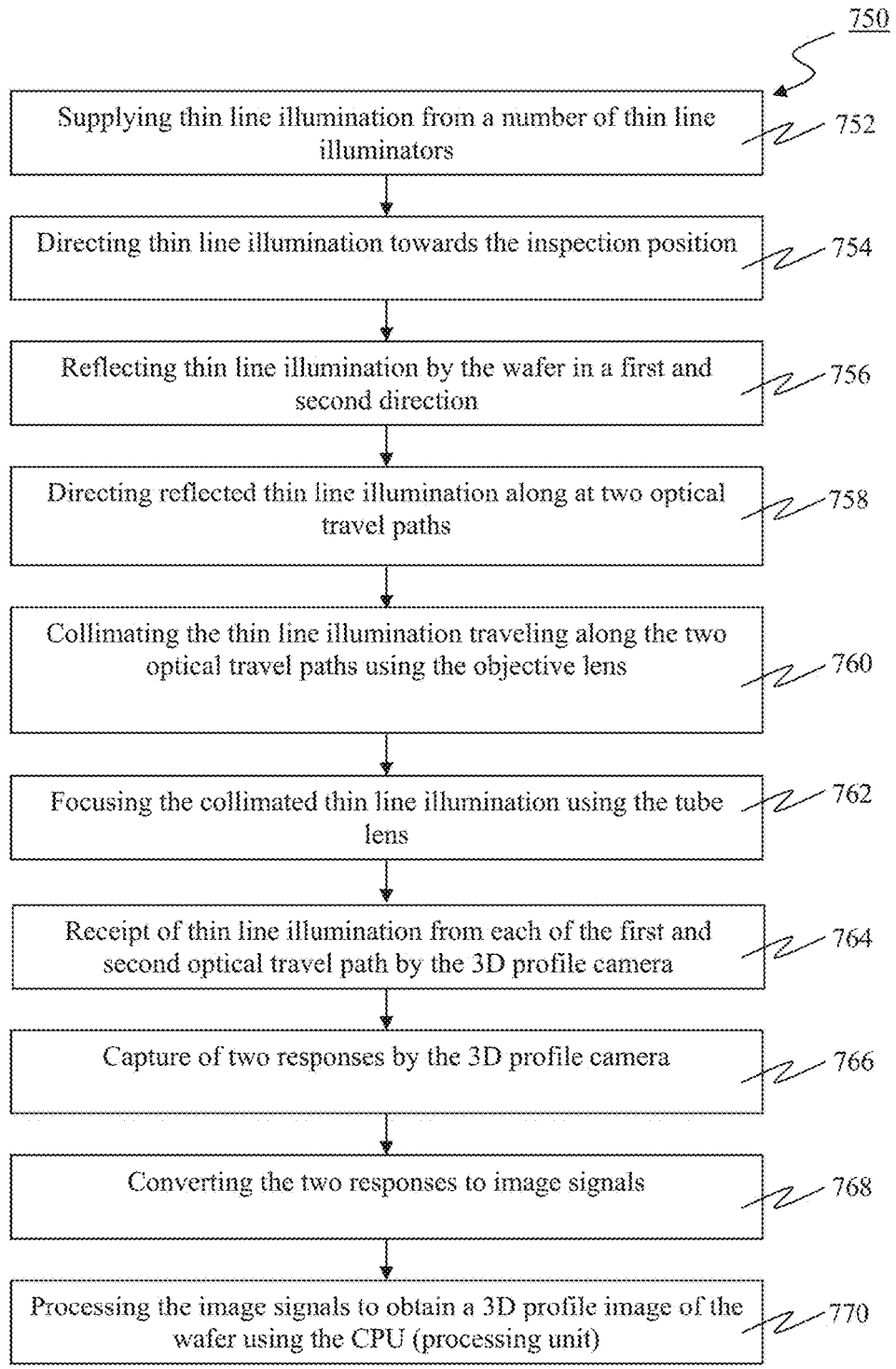
FIG. 25 is a process flow diagram of a second exemplary three-dimensional wafer scanning process performed in the process of FIGS. 17A and 17B in accordance with an embodiment of the present disclosure.

FIG. 25 shows a flowchart of a second three-dimensional (3D) wafer scanning process 750 in accordance with particular embodiments of the present disclosure.

In many embodiments, the second three-dimensional (3D) wafer scanning process 750 facilitates or enables simultaneous capture, by the 3D profile camera 56, of thin line illumination that has been reflected off the surface of the wafer 12 in at least two different directions, where each different direction defines at least a portion of a distinct reflected illumination travel path. A reflected illumination travel path can be defined as a path or route along which illumination propagates and/or is directed away from the inspection position as a result of interaction with the wafer's surface topology (e.g., by way of reflection or scattering) toward or to an image capture device (e.g., the 3D profile camera) 56. In several embodiments, the second three-dimensional (3D) wafer scanning process 750 can be selected and used where the system 10 includes a number of sets of reflectors 84 (i.e., at least one set of reflectors 84 or reflector assemblies). For purposes of brevity and clarity, the second three-dimensional (3D) wafer scanning process 750 described hereinafter is performed with a system 10 that includes two sets of reflectors or reflector assemblies 84a, 84b. Accordingly, the second three-dimensional (3D) wafer scanning process 750 described below is associated with a simultaneous capture of thin line illumination reflected off the wafer 12 in two different directions to thereby facilitate or enable an at least substantially simultaneous capture of two responses (or optical responses), or two views, of a 3D characteristic (e.g., a 3D feature) of the wafer 12.

In a first process portion 752 of the second 3D wafer scanning process 750, thin line illumination is provided, supplied, or emitted by one or more thin line illuminators 52 (or thin line illumination emitter). In some embodiments, for example as shown in FIG. 27a, thin line illumination is supplied by one thin line illuminator 52. In other embodiments, thin line illumination is supplied by at least two thin line illuminators 52, for example by at least the first thin line illuminator 52a and the second thin line illuminator 52b as shown in FIG. 27b.

In particular embodiments, multiple beams of thin line illumination can be directed to the surface of the wafer 12, for instance, a first beam of thin line illumination and a second beam of thin line illumination can be directed to the wafer's surface. In an embodiment such as that shown in FIG. 27b, the first thin line illuminator 52a can emit, output, or provide the first beam of thin line illumination the second thin line illuminator 52b can emit, output, or provide the second beam of thin line illumination.

In a second process portion 754, thin line illumination supplied by the thin line illuminator(s) 52 is directed towards the inspection position. In several embodiments, a number of sets of mirrors 54 (or mirror assemblies) are used for directing thin line illumination supplied by the thin line illuminator(s) 52 towards the inspection position.

In the embodiment shown in FIG. 27a, thin line illumination is directed to the inspection position along a single incident illumination travel path. An incident illumination travel path can be defined as a path or route along which illumination propagates and/or is directed from the thin line illuminator 52 to the inspection position. In a representative implementation such as that indicated FIG. 27a, a single set of mirrors 54 can facilitate direction of thin line illumination toward or to the wafer, such that the thin line illumination arrives at the wafer surface at an intended angle of incidence (e.g., approximately 0° with respect to an axis that is normal or perpendicular to the wafer surface).

In the embodiment shown in FIG. 27b, thin line illumination is directed to the inspection position along two different or distinct incident illumination travel paths. More particularly, a first beam of thin line illumination provided by the first thin line illuminator 52a travels along a first incident illumination travel path to the inspection position, and a second beam of thin line illumination provided by the second thin line illuminator 52b travels along a second incident illumination travel path to the inspection position. In general, at the inspection position, the first beam of thin line illumination and the second beam of thin line illumination are coincident or overlapping. A first set of mirrors 54a can direct the first beam of thin line illumination along the first incident illumination travel path, and a second set of mirrors 54b can direct the second beam of thin line illumination along the second incident illumination travel path. By way of the first set of mirrors 54a, the first beam of thin line illumination can arrive at the wafer surface at a first angle of incidence (e.g., approximately 0° with respect to an axis that is normal to the wafer surface); similarly, by way of the second set of mirrors 54b, the second beam of thin line illumination can arrive at the wafer surface at a second angle of incidence (e.g., approximately 45° with respect to the aforementioned normal axis) that is different than the first angle of incidence.

In a number of embodiments, the number of sets of mirrors 54 corresponds to the number of thin line illuminators 52. Accordingly, in various embodiments, the first set of mirrors 54*a* is used for directing the first beam of thin line illumination that is supplied by the first thin line illuminator 52*a* towards the inspection position along the first incident illumination travel path, and the second set of mirrors 54*b* is used for directing the second beam of thin line illumination that is supplied by the second thin line illuminator 52*b* towards the inspection position along the second incident illumination travel path.

In a third process portion 756, thin line illumination is reflected off the surface topology of the wafer 12 at the inspection position. Thin line illumination incident onto the surface of the wafer 12 can be reflected in a number of directions, more specifically a number of different directions.

The direction(s) in which thin line illumination is reflected off the surface of a wafer 12 is often dependent, or at least partially dependent, upon the topological features (e.g., the 3D characteristics) of the surface of the wafer 12 at the inspection position. For example, structural, geometrical, or topological variation on the surface of the wafer 12 can cause thin line illumination incident on the wafer 12 to be reflected in different directions.

Generally, depending upon surface profile, for example 3D or topological characteristics of a wafer 12, thin line illumination reflected off the surface of the wafer 12 can scatter or disperse in multiple different directions. In prior systems in which illumination reflected off of a wafer's surface is captured only from a single reflection direction, dispersion of thin line illumination in multiple directions can make it difficult to obtain an accurate measurement, analysis, or determination of the surface profile of the wafer 12. This is generally because the dispersion of thin line illumination reflected off the surface of the wafer 12 can result in an inappropriately reduced amount of reflected thin line illumination entering the 3D profile camera 56, thereby resulting in the capture of dimmer images (or poorer responses) by the 3D profile camera 56. It is generally difficult to derive accurate measurements or analysis from images that are too dim. Sometimes, the dispersion of thin line illumination reflected off the surface of the wafer 12 can result in an inappropriately increased amount of reflected thin line illumination entering the 3D profile camera 56, thereby resulting in the capture of overly bright images by the 3D profile camera 56. It is also difficult to derive accurate measurements or analysis from images that are too bright. In accordance with aspects of the present disclosure, illumination reflected from the surface of the wafer in multiple different directions is directed to the 3D profile camera 56 along multiple corresponding (e.g., predetermined or selectable) reflected illumination travel paths, such that the 3D profile camera 56 can simultaneously capture multiple reflected illumination responses corresponding to the inspection position under consideration.

In a fourth process portion, thin line illumination reflected from the surface of the wafer 12 in at least two different directions is directed towards the 3D profile camera 56 along at least two different, distinct, or distinguishable reflected illumination travel paths, where each reflected illumination travel path corresponds to a distinct set of reflectors 84*a*, 84*b*. In several embodiments of the present disclosure, the system 10 includes at least two sets of reflectors or at least two reflector assemblies 84*a*, 84*b*, configured and disposed to receive thin line illumination reflected off a wafer 12. Each set of reflectors or each reflector assembly 84*a*, 84*b* is configured and disposed to receive and/or (re)direct thin line illumination that has been reflected off a wafer 12 in a particular distinct direction.

More specifically, in various embodiments, thin line illumination reflected off the surface of a Wafer 12 in a first direction is received and (re)directed along a first reflected illumination travel path that leads toward or to the 3D profile camera 56 by the first set of reflectors 84*a*, and thin line illumination reflected off the surface of the wafer 12 in a second direction is received by the second set of reflectors 84*b* and (re)directed along a second reflected illumination travel path that leads toward or to the 3D profile camera 56.

Thus, the first set of reflectors 84*a* is configured and disposed to direct thin line illumination received thereby along a first reflected illumination travel path, and the second set of reflectors 84*b* is configured and disposed to direct thin line illumination received thereby along a second reflected illumination travel path. The first and second reflected illumination travel paths (or optical reflection travel paths) include portions (e.g., spatial segments) that are separate and different from each other.

Although particular embodiments of the present disclosure are associated with two sets of reflectors 84 or two sets of reflector assemblies 84*a*, 84*b* for receiving thin line illumination reflected off a surface of a wafer 12 in two different directions, alternative numbers of sets of reflectors 84, for example three, four, or more sets of reflectors 84, can be used with the system 10 for receiving thin line illumination reflected off a surface of a wafer 12 in a corresponding number of directions.

In many embodiments, at least portions of the first and second incident and/or reflected illumination travel paths are non-parallel (e.g., divergent or convergent) in relation to each other. In numerous embodiments, the first set of reflectors 84*a* and the second set of reflectors 84*b* are configured or disposed in a substantially symmetrical manner relative to each other.

In numerous embodiments, a fifth process portion 760 involves transmission of thin line illumination traveling along each of the first and second reflected illumination travel paths through the objective lens 58 or objective lens assembly 58. The objective lens 58 collimates the thin line illumination transmitted therethrough.

In a sixth process portion 762, collimated thin line illumination is transmitted through the tube lens 60. In a seventh process portion 764, thin line illumination corresponding to each of the first and second reflected illumination travel paths enters the 3D profile camera 56. As above described, the tube lens 60 facilitates or effectuates focusing of the collimated thin line illumination onto the image capture plane of the 3D profile camera 56. In many embodiments, the focusing of thin line illumination onto the image capture plane of the 3D profile camera 56 enables capture of two responses, or two views of a 3D profile image, associated with the wafer 12.

This capture of two responses (or optical responses), or two views of a 3D profile image, associated with the wafer surface topology at the inspection position under consideration occurs in an eighth process portion 766. For purposes of the present disclosure, the two responses can be referred to as a first response and a second response, and the two views of the 3D profile image can be referred to a first view and a second view of the 3D profile image. In various embodiments, the first and second response can be focused on the image capture plane of the 3D profile camera 56 and captured such that they are spatially adjacent to each other. The first response, or the first view of the 3D profile image, associated with the wafer surface topology at the current inspection position is produced from, or using, thin line illumination traveling along the first reflected illumination travel path. The second response, or the second view of the 3D profile image, associated with the wafer surface topology at the current inspection position is produced from, or using, thin line illumination traveling along the second optical travel path.

The first response and the second response can be captured as a single set of image data that includes image data corresponding to a manner in which illumination was reflected from the surface topology of the wafer 12 in each of the first and second directions. In the event that the illumination incident upon the surface of the wafer 12 included a first beam of thin line illumination and a second beam of thin line illumination, the composite response can include image data corresponding to a manner in which the first beam of thin line illumination was reflected from the surface topology of the wafer 12 in the first direction, and image data corresponding to a manner in which the second beam of thin line illumination was reflected from the surface topology of the wafer 12 in the second direction. In some embodiments, the first beam of thin line illumination can be provided at a first optical wavelength, and the second beam of thin line illumination can be provided at a second optical wavelength (e.g., the first thin line illuminator 52a can output illumination having a different wavelength than that output by the second thin line illuminator 52b). In such embodiments, the 3D profile camera 56 can be a color camera in order to facilitate the capture and differentiation and/or analysis of the first and second responses.

Other embodiments in which the system 10 includes more than two sets of reflectors can enable capture of more than two responses, or views of the 3D profile image, associated with the wafer 12.

In a subsequent process portion 768, the responses, for example the first response and the second response, are transmitted to the CPU or processing unit (e.g., as a single set of image data). In a next process portion 770, the responses, for example the first response and the second response, are processed by the CPU for determining or obtaining information corresponding to the 3D characteristic(s) or topology of the wafer 12. The CPU can generate or determine a composite response using the first and second responses, where the composite response corresponds to a single response or image that indicates particular 3D characteristics of the wafer surface topology at the inspection position corresponding to the first and second responses. In some embodiments, the processing of the responses in the process portion 770 facilitates or enables at least one of 3D height measuring, co-planarity measuring, 3D feature analyzing, and/or detecting and/or classifying a defect on a wafer 12.

In several embodiments of the present disclosure, the process portions 752 to 770 can be repeated any number of times for capturing a corresponding number of sets of first and second responses and transmitting said sets of responses to the CPU for obtaining information on the 3D characteristic(s) or topology of the wafer 12. For instance, the process portions 752-770 can be repeated for each inspection position along a wafer scan motion path that is defined to include multiple inspection positions at which image data corresponding to wafer surface topology is to be captured and analyzed.

(1) Third 3D Wafer Scanning Process 950

Figure 30:
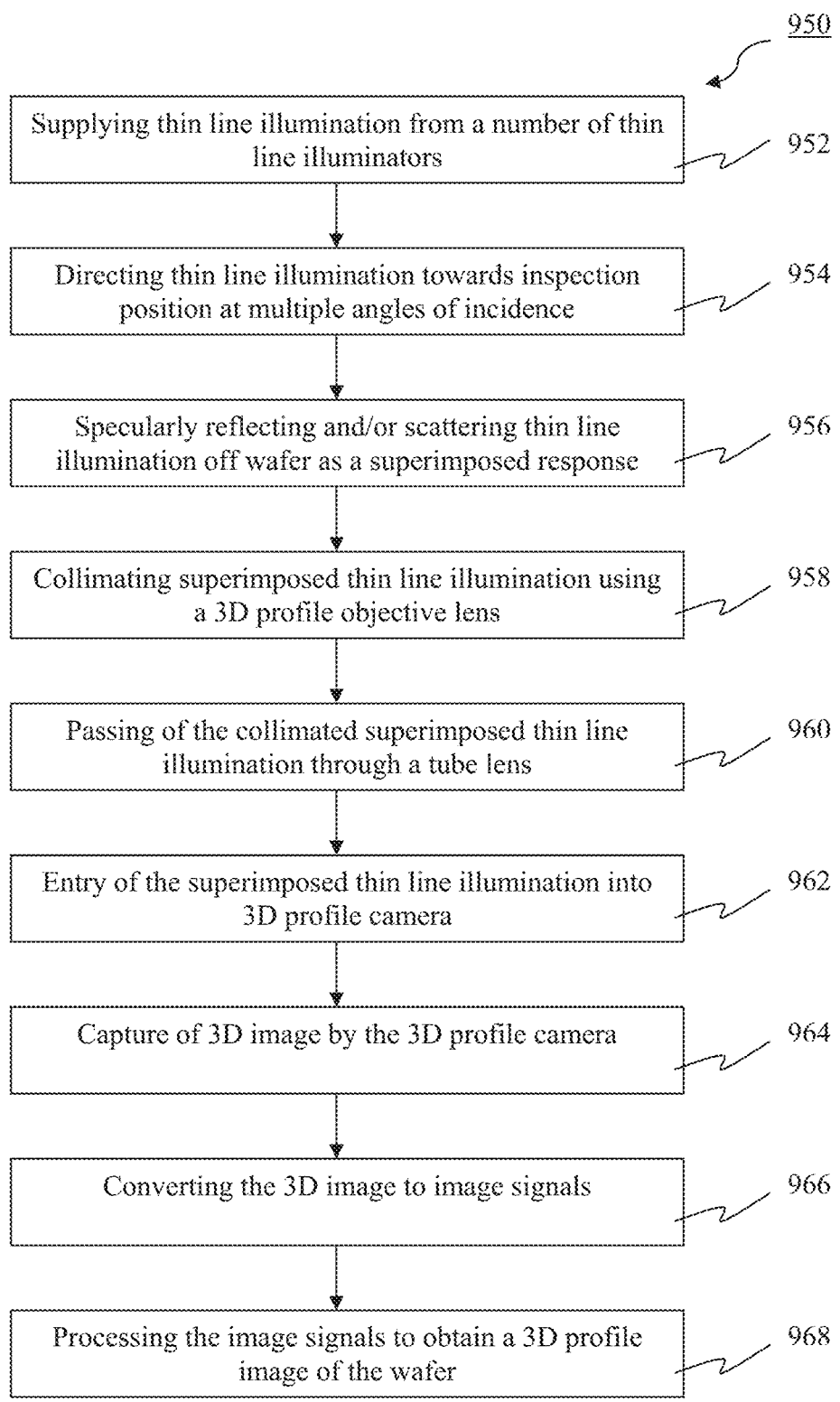
FIG. 30 is a process flow diagram of a third three-dimensional (3D) wafer scanning process in accordance with particular embodiments of the present disclosure.

FIG. 30 shows a flowchart of the third three-dimensional (3D) wafer scanning process 950 in accordance with particular embodiments of the present disclosure.

The process 950 can be used, applied, or selected when the system 10 omits or excludes (e.g., inherently as a result of system design, or selectively as a result of a selectable system configuration) reflector(s), for instance the set of reflectors 84a, 84b, for reflecting and/or redirecting illumination that is reflected off a surface of the wafer 12. For example, in various embodiments, the process 950 can be used, applied, or selected with the system 10 of FIG. 27c.

A first process portion 952 involves directing multiple beams of thin line illumination to or toward a target location or region of a surface of the wafer 12. The first process portion 952 can involve supplying or emitting thin line illumination from a number of thin line illuminators 52, for example, at least one thin line illuminator 52, and in several embodiments at least two thin line illuminators 52 (i.e., a first thin line illuminator 52a and a second thin line illuminator 52b) as shown in FIG. 27c.

In a second process portion 954, the thin line illumination emitted from each of the first and second thin line illuminators 52a and 52b is directed towards the inspection position, more specifically a wafer 12, or a portion of the wafer 12 (e.g., a target location or region on the wafer 12), that is positioned at the inspection position.

In some embodiments, a number of sets of mirrors 54 (e.g., one or more mirrors 54) can be used to direct the thin line illumination emitted from one or more of the thin line illuminator(s) 52 to or towards the wafer 12 that is positioned at the inspection position. The number of sets of mirrors 54 used can be dependent, or at least partially dependent, upon the number of thin line illuminators 52 used to supply or emit thin line illumination towards the wafer 12, and/or a particular angular configuration between a given thin line illuminator 52, the surface or plane of the wafer 12, and the image capture device 56 (e.g., an optical axis of the image capture device 56).

In several embodiments, the thin line illuminators 52a and 52b and/or one or more sets of mirrors 54 are positioned and/or configured such that the thin line illumination is directed towards the wafer 12 at particular angles relative to a plane of the wafer 12 and/or an optical axis of the image capture device 56. In particular embodiments, the thin line illuminators 52a and 52b and/or at least one mirror 54 can be positioned and/or configured for controlling, for instance selecting and/or varying, a set of angles at which beams of thin line illumination are directed to or towards the wafer 12, and a set of angles at which beams of reflected and/or scattered thin line illumination travel away from the wafer 12 to or toward the image capture device's optical axis.

Optical Inspection in View of Aspects of Specular Reflection and Scattering

Specular reflection (also referred to herein as complete, full, essentially full, or substantially full reflection) occurs when substantially or approximately all thin line illumination incident upon a highly reflective, mirror-type, or shiny surface (e.g., a portion or target region of a wafer 12 having a mirror-type finish) at a particular angle of incidence is reflected from the surface at a reflection angle having a magnitude equal to the angle of incidence. More particularly, when thin line illumination provided at an intensity $I_1$ and an angle $\alpha_1$ relative to a normal axis of a planar mirror-type surface or surface feature strikes the mirror-type surface, the reflected thin line illumination exhibits an intensity $I_2$ that is equal or approximately equal to $I_1$, and substantially all or the majority of the reflected thin line illumination travels away from the planar mirror-type surface along an optical path at an angle $\alpha_2$ relative to the normal axis, where $\alpha_1$ and $\alpha_2$ are on opposite sides of the normal axis and the magnitudes of $\alpha_1$ and $\alpha_2$ are equal or approximately equal (that is, with respect to the normal axis and angular magnitude, $\alpha_1$ and $\alpha_2$ are congruent, i.e., $\alpha_2$ equals $\alpha_1$). Thus, for a wafer surface, surface feature, or structure that fully reflects thin line illumination incident an intensity of $I_1$ along an angle $\alpha_1$, a reflected thin line illumination intensity $I_2$ at least approximately equals $I_1$ along an reflection angle $\alpha_2$ that equals $\alpha_1$.

Scattering, non-specular, or diffuse reflection (also referred to herein as partial or incomplete reflection) occurs when thin line illumination incident upon a non mirror-type surface (e.g., a textured, rough, matte, or non-smooth surface and/or a topographically variable or non-uniform surface that includes a set of scattering centers such as solder bumps) is scattered, diffusely reflected, or redirected away from the surface along one or more optical travel paths that differ from the thin line illumination's angle of incidence upon the non mirror-type surface. That is, a given scattered illumination travel path can exhibit a reflection or redirection angle having a magnitude that is not equal or approximately equal to the thin line illumination's angle of incidence. Thus, when thin line illumination provided at an intensity $I_1$ and an angle $\alpha_1$ relative to a normal axis of a non mirror-type surface or surface feature strikes the non mirror-type surface, thin line illumination that is reflected along an optical travel path defined by a reflection angle $\alpha_2$ that is on the opposite side of the normal axis and which has a magnitude that is equal or approximately equal to $\alpha_1$ (i.e., $\alpha_2$ equals $-\alpha_1$) exhibits an intensity $I_2$ that is less than or substantially less than $I_1$ because the non mirror-type surface scatters or diffuses the incident thin line illumination along one or more angles that differ from $\alpha_1$.

In accordance with aspects of the present disclosure, multiple beams of thin line illumination can be simultaneously directed to or toward a target location or region of a wafer 12, such that (a) a full reflection response corresponding to full reflection of incident thin line illumination by the target wafer location; and (b) a scattering response corresponding to scattering, diffusion, or partial reflection by the target wafer location can be simultaneously generated at the target wafer location, and simultaneously detected or captured as a superimposed response by a single image capture device 56. Such simultaneous generation and simultaneous capture of multiple distinct types of responses (e.g., a superimposed response that includes a full reflection response and a scattering response) to incident thin line illumination can facilitate or enable a more complete, more accurate, and/or more efficient characterization or analysis of 3D aspects of the target wafer location.

In most embodiments, the image capture device 56 can be positioned at a given (e.g., predetermined or adjustable) illumination response angle relative to a normal axis that is defined with respect to the plane or surface of the wafer 12 (or the horizontal plane of the wafer table 16). The normal axis, for instance, can be defined relative to the plane of the wafer 12 at an approximate midpoint within a cross sectional area within which the first and second beams of thin line illumination are incident upon the wafer plane. The illumination response angle corresponds to an angle at which illumination that is reflected or scattered from a wafer location or surface under consideration leaves or propagates away from the wafer location or surface as a result of such reflection or scattering. An angle at which a given beam of thin line illumination is directed to or towards the wafer 12, more specifically the plane of the wafer 12, depends upon whether the beam of thin line illumination is to be used to generate a full reflection response or a scattering response relative to the illumination response angle.

In various embodiments, at least a first beam of thin line illumination (e.g., provided by the first thin line illuminator 52a) is directed to or toward the plane of the wafer 12 at a first angle of incidence relative to the wafer plane's normal axis, where the magnitude of the first angle of incidence matches or equals the illumination response angle. Depending upon the reflection or scattering properties of a wafer location or position currently under consideration, if the first beam of thin line illumination is incident upon a wafer location having mirror-type finish, the first beam of thin line illumination will be fully reflected along an optical path defined by the illumination response angle, and the image capture device 56 can capture the fully reflected first beam of thin line illumination as a first response. If the first beam of thin line illumination is incident upon a wafer location having a non mirror-type surface, the first beam of illumination will not be fully reflected along the illumination response angle (i.e., it would instead be scattered), and the image capture device 56 can capture only a portion (which may be a negligible fraction) of the diffusely reflected first beam of thin line illumination as the first response.

In some embodiments, at least one mirror 54 can be used to direct the first beam of thin line illumination to or toward the wafer surface, for instance, in the event that the first thin line illuminator 52a is spatially oriented or positioned to emit the first beam of thin line illumination at an angle other than the first angle of incidence (e.g., in the event that the first thin line illuminator 52a is positioned to emit the first beam of thin line illumination along the normal axis, as shown in FIG. 27c).

In addition to the foregoing, simultaneous with the provision of the first beam of thin line illumination to or toward the wafer surface, at least a second beam of thin line illumination (e.g., provided by the second thin line illuminator 52b) can be directed to or toward the plane of the wafer 12 at a second angle of incidence relative to the normal axis, where the magnitude of the second angle of incidence is significantly different from the illumination response angle. Depending upon the reflection or scattering properties of the wafer location currently under consideration, if the second beam of thin line illumination is incident upon a wafer location having a mirror-type finish, the second beam of thin line illumination will be fully reflected along an angle other than the illumination response angle, and the image capture device 56 would capture negligible portion or essentially none of the fully reflected second beam of thin line illumination as a second response. If the second beam of thin line illumination is incident upon a wafer location having a non mirror-type finish, the second beam of thin line illumination will be scattered or diffusely reflected, and the image capture device 56 can capture a portion of the reflected second beam of thin line illumination that is scattered or diffusely reflected along an optical path defined by the illumination response angle as the second response.

In a representative implementation, the illumination response angle can be approximately 45°, and the first angle of incidence can therefore also be approximately 45°. In such an implementation, a first angular separation $\theta_1$ between the illumination response angle and the first angle of incidence can equal or approximately equal 90°. Additionally, the second angle of incidence can be approximately 0° with respect to the normal axis, that is, the second beam of thin line illumination can be directed to the plane of the wafer 12 along the normal axis. In such an implementation, a second angular separation $\theta_2$ between the illumination response angle and the second angle of incidence can equal or approximately equal 45°. When the second beam of thin line illumination is incident upon a wafer location having a mirror-type surface, the second beam of thin line illumination is fully reflected back along the normal axis. When the second beam of thin line illumination is incident upon a wafer location having a non mirror-type surface, the image capture device 56 can capture the portion of the second beam of thin line illumination that is scattered or diffusely reflected along an angle of 45°.

As indicated above, the surface characteristics or properties, and/or topographical features of a particular location, portion, or region of a wafer 12 to which illumination is directed (or semiconductor component), will influence or determine the relative likelihood that such illumination is fully reflected or scattered from the location, portion, or region of the wafer 12 under consideration. Generally, certain locations, regions or topographical features of a particular wafer 12 (or other semiconductor component) are better, or more appropriately, inspected as a result of detecting fully reflected illumination, while other locations, regions, or topographical features are better, or more appropriately, inspected as a result of detecting scattered or diffusely reflected illumination.

For instance, a solder ball on a wafer's surface can be more accurately inspected by way of the capture of thin line illumination that is scattered by the solder ball. In contrast, a reflective or highly reflective flat or smooth portion, region, or surface of the wafer 12 can be more accurately inspected by way of the capture of thin line illumination that is fully reflected off the wafer's surface. In accordance with aspects of the present disclosure, simultaneously directing thin line illumination at different angles (e.g., by way of a first angular separation $\theta_1$ between a first beam of thin line illumination and an illumination response angle of 90° and a second angular separation $\theta_2$ of 45° between a second beam of thin line illumination and the illumination response angle) to a particular target location or region of the wafer 12 can result in the simultaneous capture of a fully reflected response and a scattered response corresponding to the target location. The fully reflected response and the scattered response can be simultaneously captured by the image capture device 56 as a single superimposed response that includes the fully reflected response and the scattered response.

For purposes of brevity and clarity, the following description of additional portions of the process 950 is provided in association with the first and second angles of incidence and/or the first and second angular separations $\theta_1$ and $\theta_2$ defined above. It will, however, be appreciated that thin line illumination can be directed towards the wafer 12 at other angles, for example 25°, 30°, 50°, 60°, or 75°, within the scope of the present disclosure, such that a fully reflected response and a scattered response can be simultaneously generated as a superimposed response, and the image capture device 56 can capture the superimposed response.

In various embodiments of the present disclosure, thin line illumination supplied or emitted by the first thin line illuminator 52*a* is directed towards the wafer 12 (or a plane of the wafer 12) at approximately 45° relative to the normal axis, and is hereinafter referable to as a 45° thin line illumination. The thin line illumination supplied or emitted by the second thin line illuminator 52*b* is directed towards the wafer 12 (or a plane of the wafer 12) at approximately 0° relative to the normal axis, and is hereinafter referable to as a 0° thin line illumination.

In a third process portion 956, the thin line illumination emitted from each of the first and second thin line illuminators 52*a* and 52*b* are reflected off the wafer 12 (e.g., as a result of full reflection and/or scattering), or a portion of the wafer 12, positioned at the inspection position.

In many embodiments, the 45° thin line illumination and the 0° thin line illumination that are scattered or reflected the wafer 12 can be superimposed to provide or produce a superimposed thin line illumination. The superimposed thin line illumination can include or embody one or more properties, characteristics, and/or associated benefits or advantages of each of the 45° thin line illumination and the 0° thin line illumination. Accordingly, the superimposed thin line illumination can facilitate or enable inspection of the wafer 12 in a manner that indicates whether a wafer location under consideration corresponds to a highly reflective or mirror-type surface, or a non mirror-type surface.

In a fourth process portion 958, the superimposed thin line illumination reflected off the wafer 12 is transmitted through the 3D profile objective lens 58, which has an aberration corrected at or to infinity. Accordingly, the transmission of the superimposed thin line illumination through the 3D profile objective lens 58 collimates the superimposed thin line illumination.

In a fifth process portion 960, the collimated superimposed thin line illumination passes through the tube lens 60. As described above, the tube lens 60 facilitates or effectuates focusing of the collimated superimposed thin line illumination onto the image capture plane of the 3D profile camera 56.

In a sixth process portion 962, the superimposed thin line illumination enters the 3D profile camera 56. In some embodiments, the 3D profile camera 56 is a monochromatic camera. In other embodiments, the 3D profile camera 56 is a color camera that is capable of receiving, capturing, distinguishing, identifying, and/or separating thin line illumination of different wavelengths.

A seventh process portion 964 involves capture of a first 3D profile image. For purposes of the present disclosure, a 3D profile image or a 3D image can refer to an image that includes, provides, or conveys information or signals that correspond to three-dimensional characteristics of a surface or structure (e.g., the topography of a surface or structure). In addition, a 3D profile image can also be referred to as a response, or optical response, captured by the 3D profile camera 56.

In an eighth process portion 966, the first 3D profile image is converted to image signals and transmitted to the CPU. In a ninth process portion 968, the first 3D profile image, or image signals thereof, is processed by the CPU for at least one of 3D height measuring, co-planarity measuring, and detecting and/or classifying a defect on the wafer 12.

In several embodiments of the present disclosure, the process portions 952 to 968 can be repeated any number of times for capturing a corresponding number of 3D images, and for transmitting the captured 3D images to the CPU. The process portions 952 to 968 can be performed either at selected image capture positions along the wafer scan motion path or along the entire wafer scan motion path the whole wafer 12.

The process 950 according to particular embodiments of the present disclosure enables inspection of wafers 12 (and/or other semiconductor components) using thin line illumination that is directed at the wafers 12 at both 45° and 0° simultaneously. The 45° thin line illumination and the 0° thin line illumination can be superimposed as a result of reflection along the illumination response angle and hence captured by the image capture device 56 simultaneously. Therefore, in various embodiments, the process 900 enables inspection and/or analysis of different types of wafer topographical features or characteristics simultaneously, or substantially simultaneously.

Optical Inspection in View of Aspects of the Relative Intensities of Thin Line Illumination Emitted from Different Thin Line Illuminators In particular embodiments of the present disclosure, the relative intensity of the 45° thin line illumination and the 0° thin line illumination can be controlled, for instance selected and/or varied, as desired, for instance depending upon the characteristics, properties, and/or topographical features of the wafer 12.

More particularly, the relative intensities of 45° thin line illumination and the 0° thin line illumination can be independently controlled based upon a captured or detected intensity of a fully reflected beam of thin line illumination relative to a captured or detected intensity of a scattered or diffusely reflected beam of thin line illumination. In general, for first and second beams of thin line illumination having approximately equal intensities, a fully reflected first beam of thin line illumination exhibits a higher or much higher intensity than a scattered second beam of thin line illumination. Thus, the fully reflected first beam of thin line illumination can give rise to a captured or detected response signal having a much larger magnitude than that of the scattered second beam of thin line illumination.

In particular embodiments, in order to approximately balance or adjust the captured intensity of a response signal arising from fully reflected thin line illumination relative to the captured intensity of a response signal arising from scattered thin line illumination, the intensity of thin line illumination emitted from the first thin line illuminator 52a (i.e., the 45° thin line illumination) can be decreased relative to the intensity of thin line illumination emitted from the second thin line illuminator 52b (i.e., the 0° thin line illumination). For example an approximately 20% or 30% intensity of thin line illumination emitted from the first thin line illuminator 52a (i.e., the 45° thin line illumination) can be used relative an approximately 70% or 80% intensity of thin line illumination emitted from the second thin line illuminator 52b (i.e., the 0° thin line illumination).

The relative intensities of thin line illumination supplied or emitted by the thin line illuminators 52a, 52b can be controlled, for example by the CPU. In particular embodiments, the relative intensities of thin line illumination supplied or emitted by the thin line illuminators 52a, 52b can be controlled for correspondingly controlling, for instance selecting and/or varying, a maximum and/or minimum magnitude of the response captured by the image capture device 56.

Although examples of relative thin line illumination intensity values are provided in the present disclosure, it will be understood that other relative thin line illumination intensity values corresponding to the first and second thin line illuminators 52a and 52b can also be selected, applied, or used as desired, for instance depending upon particular properties, characteristics, and/or topographical features or the wafer 12.

Aspects, and Effects, of Using Different Wavelengths of Thin Line Illumination

In several embodiments, the wavelengths of the thin line illumination supplied or emitted by different thin line illuminators 52 of a particular system 10 are identical, or substantially identical. However, in other embodiments, the wavelengths of thin line illumination supplied or emitted by different thin line illuminators 52 of a system 10 are different, or substantially different.

In particular embodiments of the present disclosure associated with the system 10 of FIG. 27c, the wavelength of the thin line illumination that is emitted by the first thin line illuminator 52a (e.g., the first beam of thin line illumination) is different from the wavelength of the thin line illumination that is emitted by the second thin line illuminator 52b (e.g., the second beam of thin line illumination). In other words, in particular embodiments, the wavelength of the 45° thin line illumination is different from the wavelength of the 0° thin line illumination.

The thin line illumination of different wavelengths can be superimposed after reflection and/or scattering off the wafer 12 and simultaneously captured by the image capture device 56. In many embodiments wherein the wavelengths of the thin line illumination emitted from the thin line illuminators 52 are different, the image capture device 56 is a color camera. A color camera can facilitate or enable receipt, capture, distinguishing, separation, and/or identification of the thin line illumination of different wavelengths.

When the different beams of thin line illumination emitted from different thin line illuminators 52 are of the same wavelength, they may not be readily differentiated, individually identified, or separated, after superimposition. Therefore, in some cases wherein the different beams of thin line illumination emitted from different thin line illuminators 52 are of the same wavelength, there can be cross-talk, interference, or interaction between the different beams of thin line illumination. Accordingly, the response captured by the image capture device 56 can be adversely affected.

However, where the thin line illumination supplied or emitted from different thin line illuminators 52 (e.g., the first and second thin line illuminators 52a and 52b) are of different wavelengths, the cross-talk can be alleviated or eliminated, and the thin line illumination emitted from one thin line illuminator (e.g., the first thin line illuminator 52a) can be readily differentiated, individually identified, or separated from the thin line illumination emitted by a different thin line illuminator (e.g., the second thin line illuminator 52b).

In most embodiments, the difference between the wavelengths of different beams of thin line illumination emitted from different thin line illuminators is at least approximately 30 nm to reduce or eliminate cross-talk and thereby enable enhanced accuracy differentiation, identification, and/or separation of said different beams of thin line illumination.

In a particular embodiments, the wavelength of the 45° thin line illumination of the first thin line illuminator 52a is between approximately 200 nm and 750 nm, for example 300 nm, 350 nm, 400 nm, 450 nm, 500 nm, 550 nm, or 600 nm, and the wavelength of the 0° thin line illumination is least approximately 30 nm, for example approximately 50 nm, 75 nm, 100 nm, 150 nm, or 200 nm, different from the wavelength of the 45° thin line illumination.

In other embodiments, the first thin line illuminator 52a can output illumination having a center wavelength corresponding to the color red, while the second thin line illuminator 52b can output illumination having a center wavelength corresponding to the color blue or green. Alternatively, the first thin line illuminator 52a can output illumination having a center wavelength corresponding to blue or green, and the second thing line illuminator can output illumination having a center wavelength corresponding to green or blue, respectively.

In embodiments wherein the different beams of thin line illumination captured by the image capture device 56 can be identified and/or individually processed, information made available by, or associated with, each beam of thin line illumination can be obtained, used, and/or stored individually.

For instance, where the wavelength of 45° thin line illumination is different from the wavelength of 0° thin line illumination, the response captured by the image capture device (i.e., the capture of superimposed 45° thin line illumination and 0° thin line illumination) can be processed to extract information that is particularly or uniquely associated with each of the 45° thin line illumination and the 0° thin line illumination respectively.

In several embodiments of the present disclosure, intermediate and/or final results of the process portions 952 to 968, and repetitions thereof, (e.g., results obtained from processing of 3D images) are saved in the database of the CPU. In other embodiments of the present disclosure, results of the process portions 952 to 968, and repetitions thereof, (e.g., results obtained from processing of 3D images) are saved in an alternative database or memory space as required.

Figure 28A:
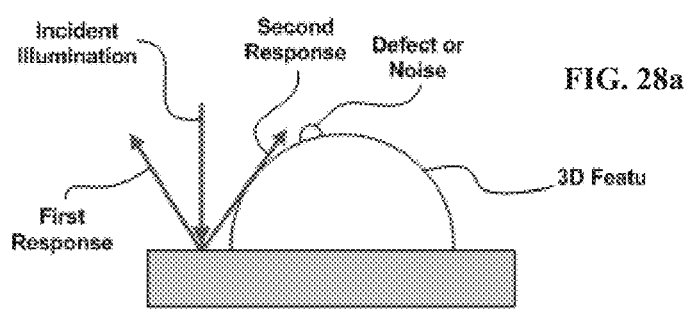
FIG. 28a illustrates reflection of illumination off a surface of a semiconductor wafer, the reflected illumination for producing a first response and a second response.
Figure 28B:
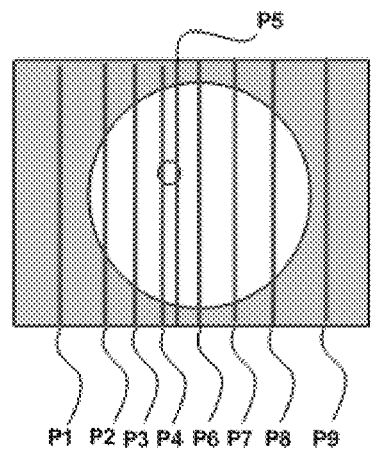
FIG. 28b illustrates multiple positions P1 to P9 along the surface of the semiconductor wafer of FIG. 28a at which illumination is reflected and subsequently received by an image capture device.

FIG. 28*a* and FIG. 28*b* illustrate representative ways in which thin line illumination that is reflected in different directions (hence different optical travel paths) from the surface of a wafer 12 can give rise to reflected thin line illumination of different, or unequal, intensities. FIG. 28*b* shows the positions along the wafer 12, i.e., positions P1 to P9, at which thin line illumination is reflected off the wafer 12, wherein positions P2 to P8 are associated with a 3D feature on the wafer 12. In some embodiments, the 3D feature at positions P2 to P8 includes or carries a defect or a source of optical noise.

Upon reflection from the surface of the wafer 12, reflected thin line illumination (or reflected beams of thin line illumination) travel away from the surface of the wafer 12 along multiple optical travel paths.

Figure 29:
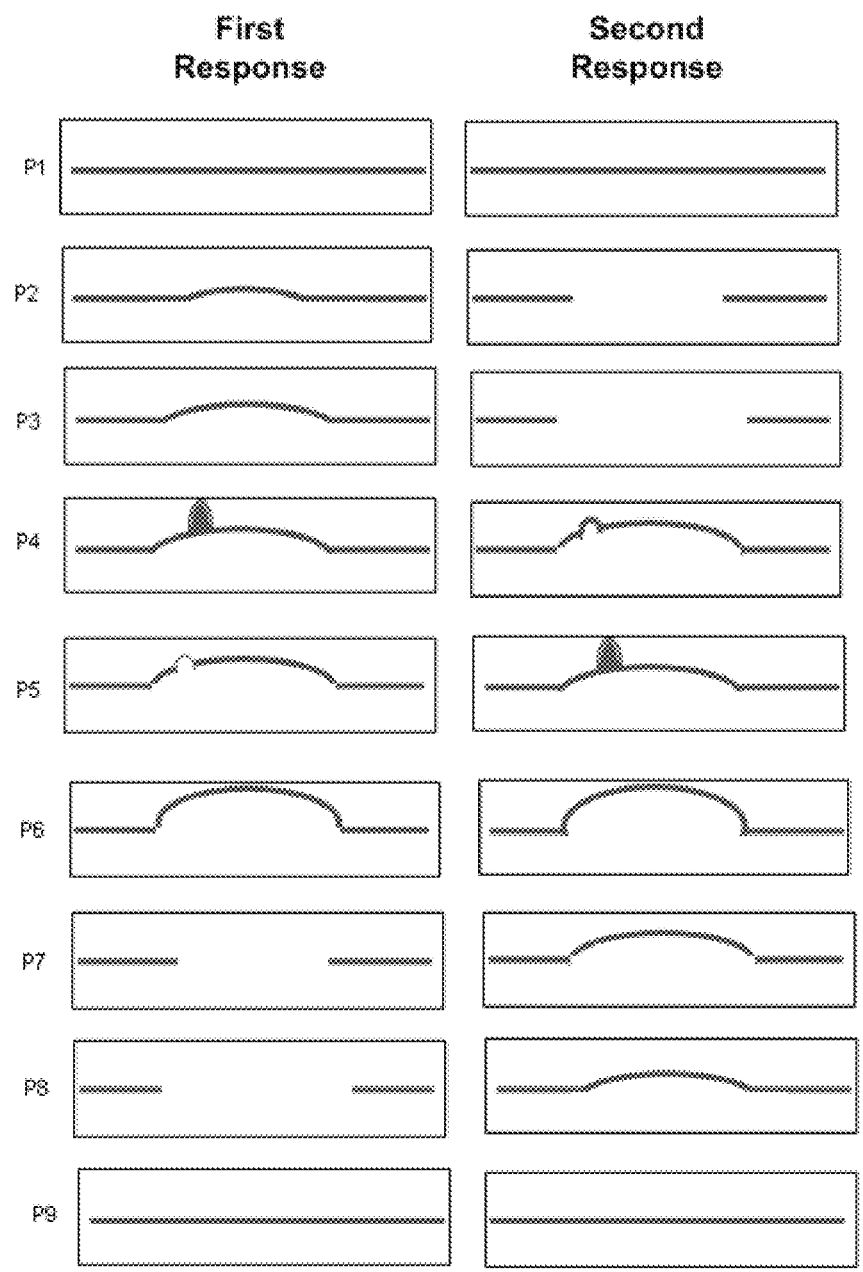
FIG. 29 shows exemplary first responses and second responses associated with each of positions P1 to P9 of FIG. 28b.

FIG. 29 depicts first and second responses, corresponding to illumination traveling along the first and second optical travel paths respectively, produced by the 3D profile camera 56 at each of positions P1 to P9. Each response (or optical response) corresponds to a particular thin line illumination intensity, distribution, pattern, and/or level, which is correspondingly associated with the surface profile, or the 3D characteristics or topology, of the wafer 12 at each of the positions P1 to P9.

As previously mentioned, the reflection of thin line illumination off the surface of the wafer 12 is dependent upon the 3D characteristics or topology of the wafer 12, for instance the presence and/or characteristics of structures, features, defects, and/or optical noise or scattering sources that are carried on the surface the wafer 12.

Accordingly, in many embodiments, the relative profiles of the first response and the second response at a given position (e.g., positions P1 to P9) along the surface of a wafer 12 are dependent upon the 3D characteristics or topology at said given position along the surface of the wafer 12.

As shown in FIG. 29, at the first wafer position P1, the thin line illumination reflected along each of the first and second optical travel paths is unaffected by 3D characteristics or topology of the surface of the wafer 12. This is due to the absence of a 3D feature on the surface of the wafer 12 at position 1. As a result, intensities of thin line illumination reflected in the first and second directions, and accordingly traveling along the first and second optical travel paths, respectively, are similar or essentially the same. Therefore, the reflection of thin line illumination off the surface of the wafer 12 at position 1 gives rise to similar first and the second responses.

However, at each of positions P2 to P8 along the surface of the wafer 12, the reflection of thin line illumination off the surface of the wafer 12 is affected by the presence of a 3D feature.

For instance, at position P2 along the surface of the wafer 12, the 3D characteristics or topology of the 3D feature results in no effect upon reflection of thin line illumination in the first direction, and hence travel of thin line illumination along the first optical travel path, but prevents thin line illumination from traveling along the second optical path (i.e., the 3D feature blocks the second optical path). This gives rise to the first response, or first optical response, having higher intensity as compared to the second response, or second optical response. As shown in FIG. 29, at position P2, the second response is at a minimum or zero intensity level. Analogous considerations apply at position P3, at which a lateral extent or span (e.g., width) of the 3D feature present is larger than at position P2.

At position P4, the thin line illumination is reflected along each of the first and second optical travel paths, but said reflection is affected by a defect carried by the 3D feature at position P4. More specifically, the defect causes greater reflection of thin line illumination in the first direction as compared to the second direction, thereby resulting in the first response, or first optical response, having a higher intensity than the second response. In various embodiments, the comparison and analysis of the first and second responses facilitates identification and/or classification of defects present on, or carried by, the surface of a wafer 12.

At position P5, thin line illumination is less strongly reflected in the first direction, hence along the first optical travel path, as compared to the second direction, hence along the second optical travel path. This results in the first response having a lower intensity as compared to the second response. The comparison and analysis of relative intensities of the first and second responses at a given position (e.g., at P5) can facilitate identification and/or classification of defects present on, or carried by, the surface of a wafer 12.

As position P6, which approximately corresponds to the top or crest of the 3D feature, thin line illumination is reflected approximately equally in each of the first and second directions, and hence along the first and second optical travel paths. Accordingly, the first and second responses are approximately equal or identical.

At each of positions 7 and 8, the 3D characteristics or topology of the 3D feature result in reflection of the thin line illumination in the second direction, and hence along the second optical travel path, but prevents reflection of thin line illumination in the first direction, and hence along the first optical travel path. As a result, at positions P7 and P8, the second response or second optical response is present, while the first response or first optical response is of a minimal or zero intensity.

Finally, at position P9, in a manner analogous to that described in relation to position P1, the reflection of thin line illumination in each of the first and second directions, hence along each of the first and second optical travel paths, is unaffected. Hence, the first and second responses at position P9 are approximately identical (e.g., of equal intensities).

In several embodiments, the second 3D wafer scanning process 750 and/or the third wafer scanning process 950 facilitate or enable capture of at least two responses, and hence at least two views, associated with 3D characteristic(s) (e.g., a 3D feature) of a wafer 12 using a single image capture device, for instance the 3D profile camera 56. In addition, in numerous embodiments, the capture of the at least two responses, and hence at least two views, associated with 3D characteristic(s) (e.g., a 3D feature) of a wafer 12 is performed simultaneously by the 3D profile camera 56.

In various embodiments, the at least two responses, or at least two views, can be combined, composed, or used together (e.g., composed) for producing a single representation, view, or image of the 3D characteristic(s) (e.g., a 3D feature) of the wafer 12. In several embodiments, the combination or composition of the at least two responses can enable production of an enhanced, for instance more accurate, image of the 3D characteristic(s) (e.g., a 3D feature) of the wafer 12.

The capture of at least two responses can improve the accuracy of 3D profiling or inspection of the wafer. For instance, in various embodiments, the capture of at least two responses can enhance accuracy of identifying defects that may be present on the surface of a wafer 12.

With existing or conventional wafer inspection methods, expensive, bulky, and/or complicated system or device set-ups involving the use of multiple image capture devices for capturing multiple responses, or views, associated with a 3D feature are generally required. It is also not possible with existing wafer inspection systems and methods to synchronize image capture by, or exposure timings of, image capture device(s) consistently. Generally, a slight non-synchronization between consecutive image captures would result in capture of undesirable or inappropriate reflection(s), hence capture of inadequate or inaccurate images. In addition, due to commonly inconsistent 3D profiles of wafers, illumination is not consistently or uniformly reflected off the surfaces of said wafers for transmission to, and capture by, image capture devices. The dispersion of illumination due to structural and geometrical variations on the surface of wafers typically results in inaccuracies in wafer inspection when using only a single view or optical response.

In many embodiments of the present disclosure, the system 10 enables illumination reflected off the surface of the wafer 12 in multiple different directions to be simultaneously captured by the 3D profile camera 56 or 3D image capture device 56. For instance, in various embodiments, the system 10 enables illumination reflected off the surface of the wafer 12 in at least a first direction and a second direction, the first and second directions being at least one of divergent and non-parallel, to be simultaneously captured by the 3D profile camera 56 or 3D image capture device 56. This facilitates or enables capture or production of multiple optical responses or images (also known as views) at each position along the surface of a wafer 12. Accordingly, numerous embodiments of the present disclosure provide for improved accuracy of 3D profiling of the wafer 12, and hence enhanced inspection of the wafer 12, for instance an increased accuracy of defect detection.

The use of a single image capture device, more specifically the 3D image capture device 56, also facilitates or effectuates an enhanced cost and/or space efficiency of the system 10. Furthermore, in various embodiments, the use of a single objective lens 58 and a single tube lens 60 helps to increase ease, speed, and accuracy of calibration associated with inspection, or image capture, of wafers 12.

In a manner similar or analogous to that described above with reference to the 2D wafer scanning or inspection processes, the collimation of illumination between the objective lens 58 and the tube lens 60 can increase the ease of introducing additional optical components into the system 10, for instance between the objective lens 58 and the tube lens 60, without having to substantially reconfigure or rearrange existing components of the system 10.

After completion of the first, second, or third 3D wafer scanning process 700, 750, 950, the detected defects, and the locations and classifications thereof, on the wafer 12 obtained by performing the process portions 416 and 418 can be consolidated. The consolidation of the defects, and the locations and classifications thereof, facilitates calculation of a review scan motion path in a process portion 420. In several embodiments of the present disclosure, the review scan motion path is calculated based on the locations of defects detected on the wafer 12 along the wafer scan motion path. In addition, defect image capture positions along the review scan motion path are calculated or determined in the process portion 420. In most embodiments of the present disclosure, the defect image capture positions correspond with the locations on the wafer 12 at which defects were detected (i.e. the DROI of the wafer 12) during the process portions 416 and 418.

In a process portion 422 of the exemplary method 400, an exemplary review process 800 according to an embodiment of the present disclosure is performed. The review process 800 enables review of defects detected in the process portions 416 and 418. In most embodiments of the present disclosure, the review process 800 occurs via at least one of a first mode 800a, a second mode 800b and a third mode 800c.

Exemplary Review Process 800

Figure 26:
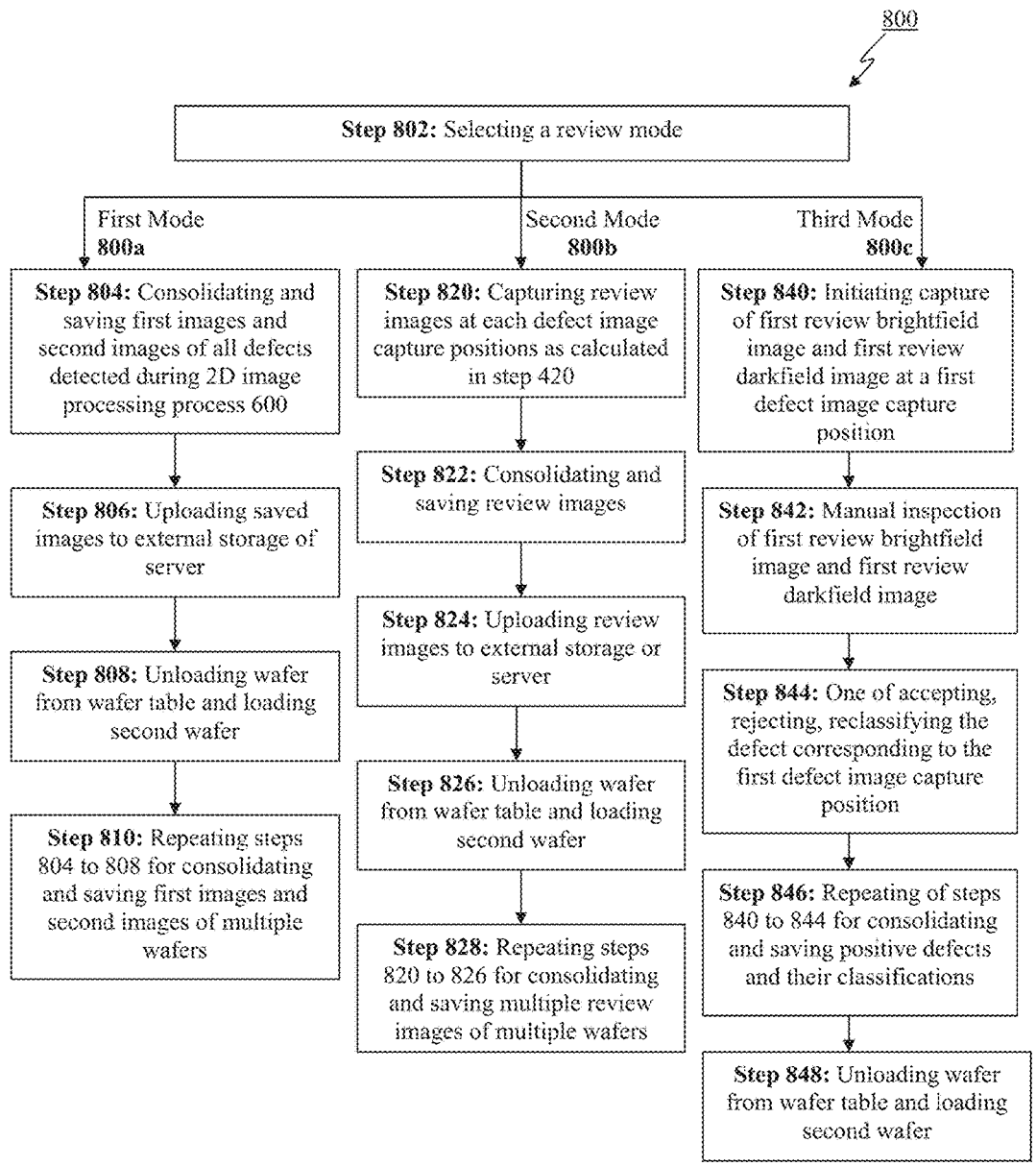
FIG. 26 is a process flow diagram of an exemplary review process performed in the process of FIGS. 17A and 17B in accordance with an embodiment of the present disclosure.

FIG. 26 shows a process flow chart of the exemplary review process 800 according to an embodiment of the present disclosure.

In most embodiments of the present disclosure, the review process 800 includes three review modes, namely the first mode 800a, the second mode 800b and the third mode 800c. In a step 802, a review mode (i.e. one the first mode 800a, the second mode 800b and the third mode 800c) is selected.

First Mode 800a of the Review Process 800

In a step 804 of the first mode 800a of the review process 800, the first images and the second images of all the defects detected during the 2D image processing process 600 performed in the step 416 of the method 400 are consolidated and saved.

In a step 806, the consolidated and saved first images and second images of the defects detected on the wafer 12 are uploaded or transferred to an external storage or server for an offline review.

In a step 808, the wafer 12 (i.e. the current wafer 12 on the wafer table 16) is unloaded and a second wafer is loaded from the wafer stack 20 onto the wafer table 16 by the robotic arm. In a step 810, each of the steps 804 to 808 is repeated for the second wafer.

The steps 804 to 810 are sequentially repeated any number of times, depending on the number of wafers of the wafer stack 20. Repetition of the step 804 to 810 results in consolidation and saving of the first images and second images obtained for each wafer of the wafer stack 20, and the uploading of the first images and the second images, to the external storage or server for an offline review. It will be appreciated by a person skilled in the art that the first mode 800a enables automated performance of the steps 804 to 810 without need for user intervention and without affecting production. This method allows continuing production while user can perform offline review of saved images. This method increases system 10 utilization as well as productivity.

Second Mode 800b of the Review Process 800

In a step 820 of the second mode 800b of the review process 800, a number of review images is captured at each of the defect image capture positions as calculated in the step 420. In several embodiments of the present disclosure, a review brightfield image and a review darkfield image are captured at each of the defect image capture positions as calculated in the step 420 using review image capture device 62 shown in FIG. 14. This is to say, a review brightfield image using brightfield illuminator 64 and a review darkfield image using darkfield illuminator 66 are captured of each defect detected by the 2D image processing process 600 of the step 416. Each of the number of review images is captured by the review image capture device 62. In several embodiments of the present disclosure, each of the number of review images is a colored image.

It will be understood by a person skilled in the art, provided with the disclosure of the present description that intensities of the brightfield illumination and darkfield illumination used for capturing the brightfield review images and darkfield review images respectively may be determined and varied as required. For example, the intensities of illumination used for capturing the number of review images may be selected based on type of wafer defect the user of the system 10 wishes to review or based on the material of wafer 12. It is also possible to capture multiple review images using various combinations and various intensity levels of brightfield and darkfield illumination set by the user.

In a step 822, the number of review images captured at each of the defect image capture positions as calculated in the step 420 are consolidated and saved. The consolidated and saved review images captured at each of the defect image capture positions are then uploaded to the external storage or server for offline review in a step 824.

In a step 826, the wafer 12 (i.e. the current wafer 12 on the wafer table 16) is unloaded and a second wafer is loaded from the wafer stack 20 onto the wafer table 16 by the robotic wafer handler 18. In a step 828, each of the steps 402 to 422 is repeated for the second wafer. Consolidated and saved first images and second images of defects detected on the second wafer are uploaded to the external storage or server.

In the second mode 800b of the review process 800, the steps 820 to 828 can be repeated any number of times, depending on the number of wafers of the wafer stack 20. Repetition of the steps 820 to 828 results in consolidation and saving of the captured brightfield review images and darkfield review images obtained for each wafer of the wafer stack 20, and the uploading of the first images and the second images, to the external storage or server for an offline review.

This method allows continuing production while user can perform offline review of saved images. This method allows capturing multiple images of each defect at various combinations of illuminations for offline review without affecting machine utilization and improves productivity.

Third Mode 800c of the Review Process 800

In most embodiments of the present disclosure, the third mode 800c of the review process 800 is initialized by a manual input, more specifically an input or a command by the user. In a step 840, the user captures a first review brightfield image and a first review darkfield image at a first defect image capture position. In a step 842, the user manually inspects or reviews the first review brightfield image and the first review darkfield image captured. In several embodiments of the present disclosure, the first review brightfield image and the first review darkfield image are displayed on a screen or monitor for facilitating visual inspection thereof by the user. The user is able to view the defect at different illumination combination using the brightfield and the darkfield illuminator.

In a step 844, the user either accepts or rejects or reclassifies the defect corresponding to the first defect image capture position. The steps 840 to 844 are then sequentially repeated for each and every defect image capture positions as calculated in the step 420.

After the steps 840 to 844 are sequentially repeated for each and every defect image capture positions, positive defects and their classifications are then consolidated and saved in a step 846. The consolidated and saved positive defects and their classifications are then uploaded or transferred to the external storage or server in a step 848. In the third mode 800c of the review process 800, the wafer 12 (i.e. the current wafer 12 on the wafer table 16) is only unloaded after the completion of the step 846. Accordingly, it will be appreciated by a person skilled in the art that the third mode 800c of the review process requires continuous user presence for effecting the visual inspection or review of each wafer.

In a step 848 of the review process 800, the wafer 12 (i.e. the current wafer 12 on the wafer table 16) is unloaded and the robotic wafer handler 18 then loads a second wafer onto the wafer table 16 from the wafer stack 20. The steps 840 to 848 are repeated any number of times depending on the number of wafers to be inspected (or number of wafers in the wafer stack 20).

It will be understood by a person skilled in the art with the disclosure provided by the description above that the first mode 800a and the second mode 800b of the review process effects a relatively indiscriminate consolidation, storage and uploading of captured images to the external storage or server. The first mode 800a and the second mode 800b represent automated review processes. The user is able to access the external storage or server for offline review of the captured images as and when required. The first mode 800a and the second mode 800b enable continuous review of each of the wafers of the wafer stack 20, or the continuous image capture, consolidation, upload and storage.

It will be appreciated by a person skilled in the art that while only three review modes, namely the first mode 800a, the second mode 800b and the third mode 800c are described in the present description, a person skilled in the art may employ alternative review processes or different permutations or combinations of the steps of each of the three review modes 800a, 800b and 800c. In addition, it will be appreciated by a person skilled in the art that each of the three review modes 800a, 800b and 800c may be modified or altered as required using methods known in the art without departing from the scope of the present disclosure.

After the performance of the review process 800, verified defects, and the locations and classifications thereof, are consolidated and saved in a step 426. The verified defects, and the locations and classifications thereof, are consolidated and saved either in the database or in an external database or memory space. The wafer map is also updated in the step 426.

As previously described, each of the captured brightfield images, DHA images and DLA images is compared with a corresponding golden reference or reference image for identifying or detecting defects on the wafer 12. The exemplary reference image creation process 900 provided by the present disclosure (as shown in FIGS. 18A and 18B) facilitates creation or derivation of such reference images. It will be understood by a person skilled in the art that the reference image creation process 900 can also be referred to as a training process.

As previously described, each of the 2D brightfield images, 2D DHA images, 2D DLA images captured during the 2D wafer scanning process 500 are preferably matched with their corresponding reference images created by the reference image creation process 900.

An exemplary comparison process is already described with the 2D image processing process 600. However, for increased clarity, a summary of matching between working images and reference images is provided below. Firstly in several embodiments of the present disclosure, the subpixel alignment of the selected working image is performed using known references including, but not limited to, templates, trace, bumps, pads and other unique patterns.

Secondly, the reference intensity of the wafer 12 at the image capture position at which the working image was captured is calculated. An appropriate reference image for matching with the working image is then selected. In several embodiments of the present disclosure, the appropriate reference image is selected from the multiple reference images created by the reference image creation process 900.

The CPU can be programmed for enabling selection and extraction of the appropriate reference image to which the working image will be matched. In most embodiments of the present disclosure, the calculation, and storage, of the normalized average or geometric mean, standard deviation, maximum and minimum intensity of each pixel of the reference images by the reference image creation process 900 enhances speed and accuracy of extracting the appropriate reference image to which the working image will be compared.

Corresponding quantitative data for each pixel of the working image is then calculated. The quantitative data is for example normalized average or geometric mean, standard deviation, maximum and minimum intensities of each pixel of the working image. The quantitative data values for each pixel of the working image is then referenced or checked against corresponding data values of each pixel of the selected reference image.

Comparison of quantitative data values between pixels of the working image and pixels of the reference image enables identification or detection of defects. In most embodiments of the present disclosure, predetermined threshold values are set by the user. Difference between the quantitative data values of pixels of the working image and pixels of the reference image is matched against the predetermined threshold values with one of multiplicative, additive and a constant value. If the difference between the quantitative data values of pixels of the working image and pixels of the reference image is greater than the predetermined threshold values, a defect (or defects) is flagged.

The predetermined threshold value can be varied as required. In several embodiments of the present disclosure, the predetermined threshold value can be varied for adjusting stringency of the process 400. In addition, the predetermined threshold value can be varied as required depending on type of defect to be detected, material of wafer 12 presented for inspection, or illumination conditions. Furthermore, the predetermined threshold value may be altered depending on a customer's, or more generally, the semiconductor industry's, requirements.

A system 10 and a process 400 for inspecting semiconductor wafers according to embodiments of the present disclosure are described above. A person skilled in the art provided with the disclosure above will understand that the modifications to the system 10 and the process 400 may be done without departing from the scope of the present disclosure. For example, sequence of process portions of the process 400, and the sequence of steps of processes 500, 600, 700, 750, 800, 900, and 950 may be modified without departing from the scope of the present disclosure.

It is an objective of the system 10 and process 400 of various embodiments of the present disclosure to enable accurate and cost-effective inspection of wafers. The ability for an automated inspection of wafers by the system 10 and the process 400 while the wafer is in motion enhances efficiency of the inspection of wafers. This is because time is not wasted for decelerating and stopping of individual wafers at an inspection position for image capture thereof, and for subsequent acceleration and transport of the wafer from the inspection position after the images have been captured, as with several existing semiconductor wafer inspection systems. Known image offsets between multiple image captures facilitate processing of the captured images to thereby detect defects that may be present therein. The offset relative to the particular set of images for the same wafer enables the software to accurately determine the co-ordinates of the defect in the wafer and, subsequently, the position of the wafer in the entire frame. The offset is preferably determined by reading the encoder values in both the X and Y displacement motors and is used to calculate the co-ordinates of a defect or defects. In addition, the use of two images at every inspect locations combines advantages of two different imaging techniques for facilitating more accurate wafer inspection.

It will also be understood by a person skilled in the art that the time-synchronization of image captures can be altered as required. More specifically, the time-synchronization may be adjusted for enhancing the ability of the programmable controller to compensate for image offset between the captured images. The system 10 and process 400 of the present disclosure facilitates accurate synchronization between supply of illumination and exposure of corresponding image capture devices for capturing of images to minimize degradation of inspection quality.

Illuminations used with the system 10 can be in the full visible spectrum of light for capture of enhanced quality images. Intensities of illumination and their combinations supplied for capture of images by the system 10 can be easily selected and varied as required depending on factors including, but not limited to, type of defects to be detected, material of the wafer and stringency of wafer inspection. The system 10 and process 400 provided by the present disclosure also enables measurement of height of 3D elements on the wafer, and analysis of 3D profile images while the wafer is moving.

The system 10 of the present disclosure has an optical setup (i.e. optical inspection head 14), which does not require frequent spatial reconfigurations to cater to changes in wafer structure or characteristics. In addition, the use of tube lenses with the system 10 enables ease of reconfiguration and design of the system 10, more specifically of the optical inspection head 14. The use of tube lenses enhances ease of introduction of optical components and accessories into the system, more specifically between objective lenses and the tube lenses.

The system 10 of the present disclosure comprises vibration isolators 24 (collectively known as a stabilizer mechanism) for buffering unwanted vibrations to the system 10. The vibration isolators 24 helps to enhance quality of images captured by the first image capture device 32, the second image capture device 34, the 3D profile camera and the review image capture device 62, and thus the accuracy of defect detection. In addition, the XY table of the system 10 enables accurate displacement and alignment of the wafer relative the inspection position.

As described in the background, existing reference image derivation or creation processes require manual selection of "good" wafers, resulting in relative inaccuracies and inconsistencies of derived reference images. Accordingly, quality of wafer inspection is adversely affected. The system 10 and process 400 according to embodiments of the present disclosure achieves enhanced quality of inspection by creating reference images without manual selection (i.e. subjective selection) of "good" wafers. The reference image creation process 900 allows for application of different thresholds of intensities across different locations of the wafer, thus accommodating non-linear illumination variations across the wafer. The process 400 therefore facilitates reduction in false or unwanted detection of defects and ultimately an enhanced quality of wafer inspection.

Embodiments of the present disclosure facilitate or enable automated defect detection using an analytical model that compares reference images with captured images of unknown quality wafers. The present disclosure also enables automated defect detection, preferably by performing digital analysis on digitalized images (i.e. working images and reference images).

Embodiments of the present disclosure facilitate or enable automated review mode without affecting production and improves machine utilization, whereas the existing equipment offers only manual review mode, which requires operator to decide every defect by looking at different illumination intensities.

In the foregoing manner, systems, apparatuses, methods, processes, and techniques for inspecting semiconductor wafers and components provided by various embodiments of the present disclosure are described. The systems, apparatuses, methods, processes, and techniques addresses at least one of the issues or problems faced by existing semiconductor inspection systems and methods as mentioned in the background. It will however be understood by a person skilled in the art that the present disclosure is not limited to specific forms, arrangements or structures of the embodiments described above. It will be apparent to a person skilled in the art in view of this disclosure that numerous changes and/or modifications can be made without departing from the scope and spirit of the disclosure.

The invention claimed is:

1. A thin line illumination and inspection apparatus comprising:
an article under inspection having a surface along which a target location resides, wherein the target location is highly reflective and scattering centers reside at the target location;
a thin line illumination setup configured to:
(a) direct an incident first beam of thin line illumination to the target location along a first angle of incidence to thereby produce a specularly reflected first beam of thin line illumination that (i) propagates away from the surface of the article under inspection at the target location along an illumination response angle having a magnitude equaul to the first angle of incidence and (ii) provides a first view of a 3D profile of the surface of the article under inspection at the target location, wherein the incident first beam of thin line illumination and the specularly reflected first beam of thin line illumination exist on opposite sides of a normal axis to the surface of the article under inspection at the target location; and
(b) simultaneously direct an incident second beam of thin line illumination to the target location along a second angle of incidence having a magnitude different than the first angle of incidence to thereby produce a non-specularly reflected second beam of thin line illumination that (iii) propagates away from the surface of the article under inspection at the target location along the illumination response angle, and (iv) provides a second view of said 3D profile of the surface of the article under inspection at the target location; and
an image capture device comprising a single 3D profile camera configured to simultaneously capture the specualarly reflected first beam of thin line illumination and the non-specularly reflected second beam of thin line illumination to thereby simultaneously capture as a single view the first view of said 3D profile of the surface of the article under inspection at the target location and the second view of said 3D profile of the surface of the article under inspection at the target location,
wherein the thin line illumination setup comprises:
a first thin line illuminator configured to supply the incident first beam of thin line illumination; and
a second thin line illuminator or the first thin line illuminator in conjunction with a mirror configured to supply the incident second beam of thin line illumination.

2. The apparatus as in claim 1, wherein the incident first beam of thin line illumination and the incident second beam of thin line illumination are overlapping at a cross-sectional area of the surface of the article under inspection to which they are directed, and the normal axis is defined relative to a plane of the surface of the article under inspection at an approximate midpoint within said cross-sectional area.

3. The apparatus as in claim 1, wherein the incident first beam of thin line illumination and the incident second beam of thin line illumination have the same wavelengths.

4. The apparatus as in claim 1, wherein the incident first beam of thin line illumination and the incident second beam of thin line illumination have different wavelengths.

5. The apparatus as in claim 1, further comprising: an objective lens assembly configured to receive the first view of the 3D profile of the surface of the article under inspection at the target location and the second view of said 3D profile of the surface of the article under inspection at the target location.

6. The apparatus as in claim 1, wherein the image capture device is configured to provide information corresponding to a three-dimensional height characteristic of the surface of the article under inspection.

7. The apparatus as in claim 4, wherein the thin line illumination setup comprises:
a first thin line illuminator configured to supply the incident first beam of thin line illumination beam at a first wavelength; and
a second thin line illuminator configured to supply the incident second beam of thin line illumination beam at a second wavelength, the first and second wavelengths being at least approximately 30 nm different from each other.

8. The apparatus as in claim 6, wherein the surface of the article under inspection is a surface of a semiconductor device, and wherein reflection of the incident first and incident second beams of thin line illumination off of the surface of the semiconductor device at the target location and the simultaneous capture of the first and second views of the 3D profile of the surface of the article under inspection at the target location occur while the semiconductor device is in motion.

9. The apparatus as in claim 1, further comprising a processing unit coupled to the image capture device, the processing unit configured to determine information corresponding to a three-dimensional characteristic of the surface of the article under inspection.

10. The apparatus as in claim 9, wherein the processing unit is configured for producing a composite of the first view of the 3D profile of the article under inspection at the target location and the second view of the 3D profile of the article under inspection at the target location to facilitate identification of a defect on the surface of the article under inspection.

11. A method for thin line illumination and inspection, comprising:
   providing an article under inspection having a surface along which a target location resides, wherein the target location is highly reflective and scattering centers reside at the target location;
   providing an illumination setup comprising:
      a first thin line illuminator configured to supply an incident first beam of thin line illumination; and
      a second thin line illuminator or the first thin line illuminator in conjunction with a mirror configured to supply an incident second beam of thin line illumination;
   providing an image capture device comprising a single 3D profile camera;
   outputting the first beam of thin line illumination and the second beam of thin line illumination with the illumination setup;
   simultaneously directing:
      (a) the incident first beam of thin line illumination to the target location along a first angle of incidence to thereby produce a specularly reflected first beam of thin line illumination that (i) propagates away from the surface of the article under inspection at the target location along an illumination response angle having a magnitude equal to the first angle of incidence, and (ii) provides a first view of a 3D profile of the surface of the article under inspection at the target location, wherein the incident first beam of thin line illumination and the specularly reflected first beam of thin line illumination exist on opposite sides of a normal axis to the surface of the article under inspection at the target location; and
      (b) the incident second beam of thin line illumination to the target location along a second angle of incidence having a magnitude different than the first angle of incidence to thereby produce a non-specularly reflected second beam of thin line illumination that (iii) propagates away from the surface of the article under inspection at the target location along the illumination response angle, and (iv) provides a second view of said 3D profile of the surface of the article under inspection at the target location;
   simultaneously capturing with the single 3D profile camera the specularly reflected first beam of thin line illumination and the non-specularly reflected second beam of thin line illumination to thereby simultaneously capture as a single view the first view of said 3D profile of the surface of the article under inspection at the target location and the second view of said 3D profile of the surface of the article under inspection at the target location.

12. The method as in claim 11, wherein the incident first beam of thin line illumination and incident second beam of thin line illumination are overlapping at a cross sectional area of the surface of the article under inspection to which they are directed, and wherein the normal axis is defined relative to a plane of the surface of the article under inspection at an approximate midpoint within said cross-sectional area.

13. The method as in claim 11, wherein the incident first beam of thin line illumination and the incident second beam of thin line illumination have the same wavelengths.

14. The method as in claim 11, wherein the incident first beam of thin line illumination and the incident second beam of thin line illumination have different wavelengths.

15. The method as in claim 11, wherein the image capture device is configured to provide information corresponding to a three-dimensional height characteristic of the surface of the article under inspection.

16. The method as in claim 14, wherein the illumination setup comprises:
   a first thin line illuminator configured to supply the incident first beam of thin line illumination beam at a first wavelength; and
   a second thin line illuminator configured to supply the incident second beam of thin line illumination beam at a second wavelength, the first and second wavelengths being at least approximately 30 nm different from each other.

17. The method as in claim 15, wherein the surface of the article under inspection is a surface of a semiconductor device, and wherein reflection of the incident first and incident second beams of thin line illumination off of the surface of the semiconductor device at the target location and the simultaneous capture of the first and second views of the 3D profile of the surface of the article under inspection at the target location occur while the semiconductor device is in motion.

18. The method as in claim 11, further comprising:
   processing the first and second views of the 3D profile of the surface of the article under inspection with a processing unit to determine information corresponding to a three-dimensional characteristic of the surface of the article under inspection.

19. The method as in claim 18, further comprising producing a composite of the first and second views of the 3D profile of the surface of the article under inspection at the target location to facilitate identification of a defect on the surface of the article under inspection.

20. The method as in claim 11, further comprising providing an objective lens assembly, and directing the specularly reflected first beam of thin line illumination and the non-specularly reflected second beam of thin line illumination towards the image capture device.

21. The method as in claim 11, further comprising establishing or adjusting an intensity of the incident first beam of thin line illumination relative to the incident second beam of thin line illumination.

22. The system as in claim 1, further comprising a processing unit configured to establish or adjust a relative intensity of the incident first beam of thin line illumination relative to the incident second beam of thin line illumination.

* * * * *